(12) United States Patent
Boyer et al.

(10) Patent No.: US 7,553,826 B2
(45) Date of Patent: *Jun. 30, 2009

(54) CYTARABINE MONOPHOSPHATE PRODRUGS

(75) Inventors: Serge Boyer, San Diego, CA (US); Mark D. Erion, Del Mar, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/582,383

(22) Filed: Oct. 18, 2006

(65) Prior Publication Data

US 2007/0037774 A1 Feb. 15, 2007

Related U.S. Application Data

(63) Continuation of application No. 10/698,928, filed on Oct. 31, 2003, now Pat. No. 7,151,092.

(60) Provisional application No. 60/423,259, filed on Oct. 31, 2002, provisional application No. 60/423,211, filed on Oct. 31, 2002.

(51) Int. Cl.
*A61K 31/661* (2006.01)
*C07D 239/20* (2006.01)
*C07F 9/6558* (2006.01)

(52) U.S. Cl. .................. 514/110; 544/243; 544/317

(58) Field of Classification Search .............. 514/110; 544/243, 317

See application file for complete search history.

(56) References Cited

U.S. PATENT DOCUMENTS

| | | |
|---|---|---|
| 3,018,302 A | 1/1962 | Bielefeld et al. |
| 3,116,282 A | 12/1963 | Hunter |
| 3,328,388 A | 6/1967 | Shen et al. |
| 4,440,740 A | 4/1984 | Fix et al. |
| 4,692,441 A | 9/1987 | Alexander et al. |
| 4,729,989 A | 3/1988 | Alexander et al. |
| 4,731,360 A | 3/1988 | Alexander et al. |
| 4,749,694 A | 6/1988 | Fix et al. |
| 4,822,773 A | 4/1989 | Alexander et al. |
| 4,835,138 A | 5/1989 | Alexander et al. |
| 4,847,298 A | 7/1989 | Alexander et al. |
| 4,952,740 A | 8/1990 | Juge et al. |
| 4,963,525 A | 10/1990 | Alexander et al. |
| 4,963,556 A | 10/1990 | Alexander et al. |
| 4,973,579 A | 11/1990 | Alexander et al. |
| 5,077,280 A | 12/1991 | Sommadossi et al. |
| 5,118,672 A | 6/1992 | Schinazi et al. |
| 5,159,067 A | 10/1992 | Schinazi et al. |
| 5,437,772 A | 8/1995 | De Castro et al. |
| 5,464,748 A | 11/1995 | Sommadossi et al. |
| 5,567,689 A | 10/1996 | Sommadossi et al. |
| 5,599,686 A | 2/1997 | DeFeo-Jones et al. |
| 5,658,889 A | 8/1997 | Gruber et al. |
| 5,663,159 A | 9/1997 | Starrett, Jr. et al. |
| 5,723,449 A | 3/1998 | Sommadossi et al. |
| 5,750,493 A | 5/1998 | Sommadossi et al. |
| 5,854,231 A | 12/1998 | Camden |
| 5,866,679 A | 2/1999 | DeFeo-Jones et al. |
| 5,948,750 A | 9/1999 | Garsky et al. |
| 5,990,093 A | 11/1999 | Schinazi et al. |
| 6,037,335 A | 3/2000 | Takashima et al. |
| 6,054,587 A | 4/2000 | Reddy et al. |
| 6,110,903 A | 8/2000 | Kasibhatla et al. |
| 6,130,504 A | 10/2000 | Nakayama et al. |
| 6,143,864 A | 11/2000 | DeFeo-Jones et al. |
| 6,177,404 B1 | 1/2001 | DeFeo-Jones et al. |
| 6,194,391 B1 | 2/2001 | Schinazi et al. |
| 6,245,749 B1 | 6/2001 | Schinazi et al. |
| 6,284,748 B1 | 9/2001 | Dang et al. |
| 6,294,672 B1 | 9/2001 | Reddy et al. |
| 6,312,662 B1 | 11/2001 | Erion et al. |
| 6,391,305 B1 | 5/2002 | Feng et al. |
| 6,395,716 B1 | 5/2002 | Gosselin et al. |
| 6,399,782 B1 | 6/2002 | Kasibhatla et al. |
| 6,407,077 B1 | 6/2002 | Gosselin et al. |
| 6,444,652 B1 | 9/2002 | Gosselin et al. |
| 6,458,773 B1 | 10/2002 | Gosselin et al. |
| 6,486,204 B2 | 11/2002 | Waldstreicher et al. |
| 6,489,476 B1 | 12/2002 | Dang et al. |
| 6,525,033 B1 | 2/2003 | Schinazi et al. |
| 6,545,007 B2 | 4/2003 | Sommadossi et al. |
| 6,566,344 B1 | 5/2003 | Gosselin et al. |

(Continued)

FOREIGN PATENT DOCUMENTS

EP 0161955 A1 11/1985

(Continued)

OTHER PUBLICATIONS

Aleksiuk et al., *J. Chem. Soc. Chem. Comm.* (1)11, (1993).

(Continued)

*Primary Examiner*—Taofiq A Solola
(74) *Attorney, Agent, or Firm*—Arnold & Porter LLP

(57) ABSTRACT

Compounds of Formula I, their preparation and uses are described:

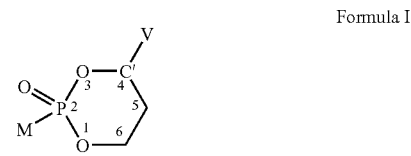

Formula I wherein:
M and V are cis to one another and MH is cytarabine;
the 5' oxygen of said cytarabine is attached to the phosphorus;
V is 4-pyridyl;
and pharmaceutically acceptable prodrugs and salts thereof.

29 Claims, 11 Drawing Sheets

U.S. PATENT DOCUMENTS

| | | | |
|---|---|---|---|
| 6,569,837 | B1 | 5/2003 | Gosselin et al. |
| 6,596,700 | B2 | 7/2003 | Sommadossi et al. |
| 6,602,664 | B2 | 8/2003 | Schinazi et al. |
| 6,635,636 | B1 | 10/2003 | Artico et al. |
| 6,752,981 | B1 | 6/2004 | Erion et al. |
| 6,946,115 | B2 | 9/2005 | Erion et al. |
| 2001/0041713 | A1 | 11/2001 | Waldstreicher et al. |
| 2002/0115596 | A1 | 8/2002 | Garsky et al. |
| 2002/0120130 | A1 | 8/2002 | Gosselin et al. |
| 2002/0147160 | A1 | 10/2002 | Bhat et al. |
| 2002/0193415 | A1 | 12/2002 | LaColla et al. |
| 2003/0050229 | A1 | 3/2003 | Sommadossi et al. |
| 2003/0060400 | A1 | 3/2003 | LaColla et al. |
| 2003/0083306 | A1 | 5/2003 | Imbach et al. |
| 2003/0225277 | A1 | 12/2003 | Kopcho et al. |
| 2003/0229225 | A1 | 12/2003 | Reddy et al. |
| 2003/0232760 | A1 | 12/2003 | Garsky et al. |
| 2004/0006002 | A1 | 1/2004 | Sommadossi et al. |
| 2004/0006007 | A1 | 1/2004 | Gosselin et al. |
| 2004/0192651 | A1 | 9/2004 | Reddy et al. |
| 2005/0101776 | A1 | 5/2005 | Gosselin et al. |
| 2005/0288240 | A1 | 12/2005 | Erion et al. |

FOREIGN PATENT DOCUMENTS

| | | |
|---|---|---|
| EP | 0180276 A1 | 5/1986 |
| EP | 0338372 A2 | 10/1989 |
| EP | 0353692 B1 | 10/1995 |
| EP | 0481214 B1 | 6/1998 |
| GB | 2266525 A | 11/1993 |
| GB | 2266527 A | 3/1999 |
| NL | 6511420 | 3/1966 |
| WO | WO 91/19721 A1 | 12/1991 |
| WO | WO 95/07287 A1 | 3/1995 |
| WO | WO 95/07920 | 3/1995 |
| WO | WO 96/01267 A1 | 1/1996 |
| WO | WO 97/03679 A1 | 2/1997 |
| WO | WO 97/49717 A1 | 12/1997 |
| WO | WO 99/45016 | 9/1999 |
| WO | WO 00/03998 A1 | 1/2000 |
| WO | WO 00/09531 A2 | 2/2000 |
| WO | WO 00/52015 A2 | 9/2000 |
| WO | WO 01/90121 A2 | 11/2001 |
| WO | WO 01/92282 A2 | 12/2001 |
| WO | WO 02/083126 A1 | 10/2002 |
| WO | WO 03/026589 A2 | 4/2003 |
| WO | WO 03/026675 A1 | 4/2003 |
| WO | WO 2004/002422 A2 | 1/2004 |
| WO | WO 2004/002999 A2 | 1/2004 |
| WO | WO 2004/003000 A2 | 1/2004 |

OTHER PUBLICATIONS

Arner et al., *Pharmacol. Ther.* 67(2):155-86, (1995).
Attansi et al., *Phosphorus Sulfur* 35(1-2), 63 (1988).
Ayral-Kaloustian et al., *Carbohydr. Res.* 187 (1991).
Bhatia et al., *Tetrahedron Lett.* 28(3), 271 (1987).
Chu et al., *J. Het. Chem.* 22:1033 (1985).
Coppi et al. *J. Org. Chem.* 53:911 (1988).
DeWaziers et al., *J. Pharm. Exp. Ther.*, 253, 387-394 (1990).
Dyatkina et al., *Tetrahedron Lett.* 35(13), 1961 (1994).
Ferroni et al., *J. Org. Chem.* 64(13), 4943 (1999).
Fuji et al., *J. Am. Chem. Soc.* 118(10):2521-2 (1996).
Gao, et al., *J. Org. Chem.* 53:4081 (1980).
Greene, T.W., *Protective Groups in Organic Chemistry*, John Wiley & Sons, New York (1999), (Outline only).
Gorenstein et al., *J. Am. Chem. Soc.* 5077 (1980).
Gish et al., *J.Med. Chem.* 14, 1159 (1971).
Hadvary et al., *Helv. Chim. Acta* 69(8), 1862 (1986).
Hanaoka et al., *Heterocycles* 23(11), 2927 (1985).
Harada et al, *Tetrahedron Lett.* 28:4843 (1987).
Hayakawa et al., *Tetrahedron Lett.* 28(20), 2259 (1987).
Hessler, *J. Org. Chem.* 41(10):1828-1831 (1976).
Hoefler et al., *Tetrahedron* 56(11), 1485 (2000).
Hulst et al., *Tetrahedron Lett.* 1339 (1993).
Jacobsen, E.N. et al., *Comprehensive Asymmetric Catalysis* (1999), (Outline only).
Kobayashi et al., *Tetrahedron Lett.* 27:4745 (1986).
Li et al., *Tetrahedron Lett.* 6615 (2001).
March, J. *Advanced Organic Chemistry*, McGraw Hill Book Company, New York, (1977 edition) pp. 251-259.
Meek et al., *J. Am, Chem Soc.* 110(7), 2317 (1988).
Merckling et al., *Tetrahedron Lett.* 2217 (1996).
Mosbo et al., ., *J. Org. Chem.* 42, 1549 (1977).
Mukaiyama, *Org. React.* 28:203 (1982).
Noyori, R. et al., *Asymmetric Catalysis on Organic Synthesis* (1994), (lis of contents only).
Postel et al., *J. Carbohyd. Chem.* 19(2), 171 (2000).
Ramachandran et al., *Tetrahedron Lett.* 38:761 (1997).
Rathore et al., *Indian J. Chem B.* 32(10), 1066 (1993).
Roodsari et al., *J. Org. Chem.* 64(21), 7727 (1999).
Sakamoto et al., Tetrahedron Lett. 33:6845 (1992).
Shen et al., *J. Org. Chem.* 30:835-838 (1965).
Shirai, et al., *Bioorg. Med. Chem. Lett.* 88:1997-2000 (1998).
Stromberg et al., *J. Nucleot.* 6(5), 815 (1987).
Takaku et al., *Chem. Lett.* (5) 699 (1986).
Torneiro et al., *J. Org. Chem.* 62(18), 6344 (1997).
Turner et al., *J. Org. Chem.* 54:4229 (1989).
Turner et al., *J. Org. Chem.* 55:4744 (1990).
Van Haperen, Ruiz et al., *Semin Oncol.* 22 Suppl. 11(4):35-41 (1995).
Vankayalapati et al., *J. Chem. Soc. Perk T I* 14, 2187 (2000).
Wechter et al., *J. Med. Chem.*, 19(8), 1013 (1976).
Yamamoto et al., *Tetrahedron Lett.* 37:1871 (1981).
Alexander, P., et al., "Preparation of 9-(2-Phosphonomethoxyethyl) Adenine Esters as Potential Prodrugs," *Collect. Czech. Chem. Commun.* 59:1853-1869, Czech Academy of Sciences, Institute of Organic Chemistry and Biochemistry (1994).
Amin, D., et al., "1-Hydroxy-3-(methylpentylamino)-propylidene-1,1-bisphosphonic Acid as a Potent Inhibitor of Squalene Synthase," *Arzneim.-Forsch/Drug Res.* 46:759-762, Blackwell Publishing, Inc. (1996).
Atiq, O., et al., "Treatment of Unresectable Primary Liver Cancer with Intrahepatic Fluorodeoxyuridine and Mitomycin C Through an Implantable Pump," *Cancer* 69:920-924, John Wiley and Sons, Inc. (1992).
Auberson, Y., et al., "N-Phosphonoalkyl-5-Aminomethylquinoxaline-2,3-Diones: In Vivo Active AMPA and NMDA-(Glycine) Antagonists," *Bioorg. Med. Chem. Lett.* 9:249-254, Elsevier Science Ltd. (1999).
Balthazor, T. and Grabiak, R.C., "Nickel-Catalyzed Arbuzov Reaction: Mechanistic Observations," *J. Org. Chem.* 45:5425-5426, American Chemical Society (1980).
Beaucage, S.L. and Iyer, R.P., "The Synthesis of Modified Oligonucleotides by the Phosphoramidite Approach and Their Applications," *Tetrahedron* 49:6123-6194, Pergamon Press Ltd. (1993).
Bespalov, A., et al., "Prolongation of morphine analgesia by competitive NMDA receptor antagonist D-CPPene (SDZ EAA 494) in rats," *Eur. J. Pharmacol.* 351:299-305, Elsevier Science B.V. (1998).
Bijsterbosch, M., et al., "Disposition of the Acyclic Nucleoside Phosphonate (S)-9-(3-Hydroxy-2-Phosphonylmethoxyproply)Adenine," *Antimicrob. Agents Chemother.* 42:1146-1150, American Society for Microbiology (1998).
Bird, J., et al., "Synthesis of Novel N-Phosphonoalkyl Dipeptide Inhibitors of Human Collagenase," *J. Med. Chem.* 37:158-169, American Chemical Society (1994).
Borch, R.F. and Millard, J.A., "The Mechanism of Activation of 4-Hydroxycyclophosphamide," *J. Med. Chem.* 30:427-431, American Chemical Society (1987).
Brill, T. and Landon, S.J., "Arbuzov-like Dealkylation Reactions of Transition-Metal-Phosphite Complexes," *Chem. Rev.* 84:577-585, American Chemical Society (1984).
Campagne, J.-M., et al., "Synthesis of Mixed Phosphate Diester Analogues of Dipeptides using BOP or PyBOP Reagents," *Tetrehedron Lett.* 34:6743-6744, Pergamon Press Ltd. (1993).

Campbell, D.A., "The Synthesis of Phosphonate Esters, an Extension of the Mitsunobu Reation," *J. Org. Chem.* 57:6331-6335, American Chemical Society (1992).

Casara, P., et al., "Synthesis of Acid Stable 5'-O-Fluoromethyl Phosphonates of Nucleosides. Evaluation as Inhibitors of Reverse Transcriptase," *Bioorg. Med. Chem. Lett.* 2:145-148, Pergamon Press plc (1992).

Casteel, D. and Peri, S.P., "Steric and Electronic Effects in the Aryl Phosphate to Arylphosphonate Rearrangement," *Synthesis* (9):691-693, Georg Thierne Verlag KG (1991).

Chen, L. and Waxman, D.J., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," *Cancer Res.* 55:581-589, The American Association for Cancer Research (1995).

Chen, L., et al., "Sensitization of Human Breast Cancer Cells to Cyclophosphamide and Ifosfamide by Transfer of a Liver Cytochrome P450 Gene," *Cancer Res.* 56:1331-1340, The American Association for Cancer Research (1996).

Cooper, D.B., et al., "Use of Carbohydrate Derivatives for Studies of Phosphorus Stereo-chemistry. Part II. Synthesis and Configurational Assignments of 1,-3,2-Oxathiaphosphrinan-2-ones and 1,3,2-Dioxaphosphorinan-2-thiones," *J. Chem. Soc. Perkin I* 3/2422:1049-1052, Royal Society of Chemistry (1974).

Dearfield, K., et al., "Analysis of the genotoxicity of nine acrylate/methacrylate compounds in L5178Y mouse lymphoma cells," *Mutagenesis* 4:381-393, Oxford University Press (1989).

De Clercq, E., et al., "A novel selective broad-spectrum anti-DNA virus agent," *Nature* 323:464-467, Nature Publishing Group (1986).

De Lombaert, S., et al., "Pharmacological Profile of a Non-Peptidic Dual Inhibitor of Neutral Endopeptidase 24.11 and Endothelin-Converting Enzyme," *Biochem. Biophys. Res. Commun.* 204:407-412, Academic Press, Inc. (1994).

De Lombaert, S., et al., "*N*-Phosphonomethyl Dipeptides and Their Phosphonate Prodrugs, a New Generation of Neutral Endopeptidase (NEP, EC 3.4.24.11) Inhibitors," *J. Med. Chem.* 37:498-511, American Chemical Society (1994).

Desos, P., et al., "Structure-Activity Relationships in a Series of 2(1*H*)-Quinolones Bearing Different Acidic Function in the 3-Position: 6,7-Dichloro-2(1*H*)-oxoquinoline-3-phosphonic Acid, a New Potent and Selective AMPA/Kainate Antagonist with Neuroprotective Properties," *J. Med. Chem.* 39:197-206, American Chemical Society (1996).

Dickson, J.K., et al., "Orally Active Squalene Synthase Inhibitors: Bis((acyloxy)alkyl) Prodrugs of the α-Phosphonosulfonic Acid Moiety," *J. Med. Chem.* 39:661-664, American Chemical Society (1996).

Edmundson, R.S., et al., "Cyclic Organophosphorous Compounds. Part 23. Configurational Assignments in the 4-Phenyl-1,3,2λ-dioxaphosphorinane Series. X-Ray Molecular Structure of cis-2-Benzylamino-4-phenyl-1,3,2-dioxaphosphorinane 2-Oxide," *J. Chem. Research (S)*, 122-123, Science Reviews Ltd. (1989).

Enriquez, P., et al., "Conjugation of Adenine Arabinoside 5'-Monophosphate to Arabinogalactan: Synthesis, Characterization, and Antiviral Activity," *Bioconjugate Chem.* 6:195-202, American Chemical Society (1995).

Erion, M., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc.* 126:5154-5163, American Chemical Society (Apr. 2004).

Erion, M., et al., "HepDirect™ Prodrugs: A Novel Strategy for Targeting Drugs to the Liver," *Hepatology* 36:301A, AASLD Abstract No. 551, John Wiley & Sons, Inc. (Oct. 2002).

Erion, M., et al., "Liver-Targeted Drug Delivery Using HepDirect Prodrugs" *J. Pharmacol. Exper. Ther.* 312:554-560, American Society for Pharmacology and Experimental Therapeutics (Feb. 2005).

Erion, M., "Liver-Targeted Nucleoside Prodrugs," presented at the *Gordon Research Conference: Purines, Pyrimidines and Related Substances*, Newport, RI, 38 pages (Jun.-Jul. 2003).

Farquhar, D., et al., "Biologically-Cleavable Phosphate Protective Groups: 4-Acyloxy-1,3,2-Dioxaphosphorinanes as Neutral Latent Precursors of Dianionic Phosphates," *Tetrahedron Lett.* 36:655-658, Elsevier Science Ltd. (1995).

Farquhar, D., et al., "Biologically Reversible Phosphate-Protective Groups," *J. Pharm. Sci.* 72:324-325, American Chemical Society (1983).

Farquhar, D., et al., "5'-4-(Pivaloyloxy)-1,3,2-dioxaphosphorinan-2-yl]-2'-deoxy-5-fluorouridine: A Membrane-Premeating Prodrug of 5-Fluoro-2'-deoxyuridylic Acid (FdUMP)," *J. Med. Chem.* 38:488-495, American Chemical Society (1995).

Farquhar, D., et al., "Synthesis and Antitumor Evaluation of Bis[(pivaloytoxy) methyl] 2'-Deoxy-5-fluorouridine 5'-Monophosphate (FdUMP): A Strategy to Introduce Nucleotides into Cells," *J. Med. Chem.* 37:3902-3909, American Chemical Society (1994).

Farquhar, D., et al., Synthesis and Biological Evaluation of 9-[5'-(2-Oxo-1,3,2-oxazaphosphorinan-2-yl)-β-D-arabinosyl]adenine and 9-[5'-(2-Oxo-1,3,2-dioxaphosphorinan-2-yl)-β-D-arabinosyl]adenine: Potential Neutral Precursors of 9-[β-D-Arabinofuranosyl]adenine 5'-Monophosphate, *J. Med. Chem.* 28:1358-1361, American Chemical Society (1985).

Farquhar, D., et al., "Synthesis and Biological Evaluation of Neutral Derivatives of 5-Fluoro-2'-deoxyuridine 5'-Phosphate," *J. Med. Chem.* 26:1153-1158, American Chemical Society (1983).

Fiume, L., et al., "Inhibition of Hepatitis B Virus Replication by Vidarabine Monophosphate Conjugated with Lactosaminated Serum Albumin," *The Lancet* 2:13-15, The Lancet Publishing Group (1988).

Freed, J.J., et al., "Evidence for Acyloxymethyl Esters of Pyrimidine, 5'-Deoxyribonucleotides as Extracellular Sources of Active 5'-Deoxyribonucleotides in Cultured Cells," *Biochem. Pharm.* 38:3193-3198, Elsevier Inc. (1989).

Friis, G.J. and Bundgaard, H., "Prodrugs of phosphates and phosphonates: Novel lipophilic α-acyloxyalkyl ester derivatives of phosphate- or phosphonate containing drugs masking the negative charges of these groups," *Eur. J. Pharm. Sci.* 4:49-59, Elsevier Science B.V. (1996).

Guida, W.C., et al., "Structure-Based Design of Inhibitors of Purine Nucleoside Phosphorylase. 4. A Study of Phosphate Mimics," *J. Med. Chem.* 37:1109-1114, American Chemical Society (1994).

He, K., et al., "Inactivation of Cytochrome P450 3A4 by Bergamottin, a Component of Grapefruit Juice," *Chem. Res. Toxicol.* 11:252-259, American Chemical Society (1998).

Hillers, S., et al., "Analogs of pyrimidinemono-and polynucleotides. VI. Phosphates of 1-(1,4-dihydroxy-2-pentyl)thymine and 1-(1,3-dihydroxy-2-propyl) uracil," *Chemical Abstracts* 89(17), Chemical Abstracts Service (1978).

Hirayama, N., et al., "Structure and conformation of a novel inhibitor of angiotensin I converting enzyme—a tripeptide containing phosphonic acid," *Int. J. Pept. Protein Res.* 38:20-24, Blackwell Publishing (1991).

Hunston, R., et al., "Synthesis and Biological Properties of Some Cyclic Phosphotriesters Derived from 2'-Deoxy-5-fluorouridine," *J. Med. Chem.* 27:440-444, American Chemical Society (1984).

Keenan, R., et al., "Pathology Reevaluation of the Kociba et al. (1978) Bioassay of 2,3,7,8-TCDD: Implications for Risk Assessment," *J. Tox. Envir. Health* 34:279-296, Hemisphere Publishing Corporation (1991).

Kelley, J.L., et al., "[[(Guaninylalkyl)phosphinico]methyl]phosphonic Acids. Multisubstrate Analogue Inhibitors of Human Erythrocyte Purine Nucleoside Phosphorylase," *J. Med. Chem.* 38:1005-1014, American Chemical Society (1995).

Khamnei, S. and Torrence, P.F., "Neighboring Group Catalysis in the Design of Nucleotide Prodrugs," *J. Med. Chem.* 39:4109-4115, American Chemical Society (1996).

Khorana, H.G., et al., "Cyclic Phosphates. III. Some General Observations on the Formation and Properties of Five-,Six- and Seven-membered Cyclic Phosphate Esters," J. Am. Chem. Soc. 79:430-436, American Chemical Society (1957).

Korba, B.A., et al., "Liver-Targeted Antiviral Nucleosides: Enhanced Antiviral Activity of Phosphatidyl-Dideoxyguanosine Versus Dideoxyguanosine in Woodchuck Hepatitis Virus Infection In Vivo," *Hepatology* 23:958-963, John Wiley & Sons, Inc. (1996).

Kryuchkov, A.A., et al., "Influence of Solvent on the Strength of Cyclic Oxygen-Containing Phosphorus Acids," *Bull. Acad. Sci.*

*USSR, A translation of Izvestiya Akademii Nauk SSSR, Ser. Khim.* 36:1145-1148, Consultants Bureau (1987).

Lefebvre, I., et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," *J. Med. Chem.* 38:3941-3950, American Chemical Society (1995).

Lok, A.S.F., et al., "Neurotoxicity associated with adenine arabinoside monophosphate in the treatment of chronic hepatitis B virus infection," *J. Antimicrob. Chemotherap.* 14;93-99, Oxford University Press (1984).

Lu, X. and Zhu, J., "Palladium-Catalyzed Reaction of Aryl Polyfluoroalkanesulfonates with O,O-Dialkyl Phosphonates," *Synthesis* (8):726-727, Georg Thieme Verlag (1987).

Ludeman, S.M., et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide," *J. Med. Chem.* 29:716-727, American Chemical Society (1986).

MacKenna, D., et al., "MB07133: A HepDirect™ Prodrug of Cytarabine Monophosphate for Use in Hepatocellular Carcinoma," *Heptaology 38(Suppl. 1)*:411A, AASLD Abstract No. 524, John Wiley & Sons, Inc. (Oct. 2003).

McGuigan, C., et al., "Intracellular Delivery of Bioactive AZT Nucleotides by Aryl Phosphate Derivatives of AZT," *J. Med. Chem.* 36:1048-1052, American Chemical Society (1993).

McGuigan, C., et al., "Kinase Bypass: A New Strategy for Anti-HIV Drug Design," *Bioorg. Med. Chem. Lett.* 3:1207-1210, Pergamon Press Ltd. (1993).

Meier, C., et al., "Cyclic Saligenyl Phosphotriesters of 2',3'-Dideoxy-2',3'-didehydrothymidine (d4T)—A New Pro-Nucleotide Approach—" *Bioorg. Med. Chem. Lett.* 7:99-104, Elsevier Science Ltd. (1997).

Meijer, D.K.F. and van der Sluijs, P., "Covalent and Noncovalent Protein Binding of Drugs: Implications for Hepatic Clearance, Storage, and Cell-Specific Drug Delivery," *Pharm. Res.* 6:105-118, Plenum Publishing Corporation (1989).

Melvin, L.S., "An Efficient Synthesis of 2-Hydroxyphenylphosphonates" *Tetrahedron Lett.* 22:3375-3376, Pergamon Press Ltd. (1981).

Meyer, R., et al., "2'-O-Acyl-6-thioinosine Cyclic 3',5'-Phosphates as Prodrugs of Thioinosinic Acid," *J. Med. Chem.* 22:811-815, American Chemical Society (1979).

Mitchell, A., et al., "Bioreversible Protection for the Phospho Group: Bioactivation of the Di(4-acyloxybenzyl) and Mono(4-acyloxybenzyl) Phosphoesters of Methylphosphonate and Phosphonacetate," *J. Chem. Soc. Perkin Trans. 1*, 2345-2353, Royal Society of Chemistry (1992).

Mitsunobu, O., "The Use of Diethyl Azodicarboxylate and Triphenylphosphine in Synthesis and Transformation of Natural Products," *Synthesis* (1):1-28, Georg Thieme Verlag (1981).

Montag, A., et al., "The Effect of Dexamethasone Treatment on CYP3A Activity Distribution, the Liver Targeting of MB07133 and CYP3A Activity in a Highly Proliferating State in Rats," *Hepatology 40(Suppl. 1)*:649A, AASLD Abstract No. 1123, John Wiley & Sons, Inc. (2004).

Moore, M., et al., "Comparison of mutagenicity results for nine compounds evaluated at the *hgprt* locus in the standard and suspension CHO assays," *Mutagenesis* 6:77-85, Oxford University Press (1991).

Murray, G., et al., "Cytochrome P450 CYP3A in human renal cell cancer," *Brit. J. Cancer* 79:1836-1842, Nature Publishing Group (1999).

Murray, G., et al., "Cytochrome P450 Expression Is a Common Molecular Event in Soft Tissue Sarcomas," *J. Pathology* 171:49-52, John Wiley & Sons, Ltd. (1993).

Nakayama, K. and Thompson, W.J., "A Highly Enantioselective Synthesis of Phosphate Triesters," *J. Am. Chem. Soc.* 112:6936-6942, American Chemical Society (1990).

Neidlein, R., et al., "Mild Preparation of 1-Benzyloxyiminoalkylphosphonic Dichlorides: Application to the Synthesis of Cyclic Phosphonic Deisters and Cyclic Monoester Amides," *Heterocycles* 35:1185-1203, Elsevier Science (1993).

Nifantyev, E.E., et al., "Synthesis and Structure of Some Stable Phospholane-Phospholanes," *Phosphorus, Sulfur and Silicon* 113:1-13, Overseas Publishers Association (1996).

Ogg, M., et al., "A reporter gene assay to assess the molecular mechanisms of xenobiotic-dependent induction of the human CYP3A4 gene in vitro," *Xenobiotica* 29:269-279, Taylor & Francis Ltd. (1999).

Ohashi, K., et al., "Synthesis of Phosphonosphingoglycolipid Found in Marine Snail *Turbo Cornutus*." *Tetrahedron Lett.* 29:1189-1192, Pergamon Press plc (1988).

Petrakis, K. and Nagabhushan, T.L., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc.* 109:2831-2833, American Chemical Society (1987).

Pitcher, H.R., "Built-in Bypass," *Nature* 429:39, Nature Publishing Group (May 2004).

Predvoditelev, D.A., et al., "Glycero-2-Hydroxymethylene Phosphates," *J. Org. Chem. USSR, A Translation of Zhur. Org. Khim.* 13:1489-1492, Plenum Publishing Corporation (1977).

Predvoditelev, D.A., et al., "Synthesis of Lipids and Their Models on the Basis of Glycerol Alkylene Phosphites. V. Cyclic Phosphatidylglycerol and Phosphatidylhydroxyhomocholine," *J. Org. Chem. USSR, A Translation of Zhur. Org. Khim.* 17:1156-1165, Plenum Publishing Corporation (1981).

Reddy, K.R., et al., "Stereoselective synthesis of nucleoside monophosphate HepDirect™ prodrugs," *Tetrahedron Lett.* 46:4321-4324, Elsevier Ltd. (2005).

Reddy, M.R., et al., "Development of a Quantum Mechanics-Based Free-Energy Perturbation Method: Use in the Calculation of Relative Solvation Free Energies," *J. Am. Chem. Soc.* 126:6224-6225, American Chemical Society (published online Apr. 2004).

Redmore, D., "Phosphorus Derivatives of Nitrogen Heterocycles. 2. Pyridinephosphonic Acid Derivatives," *J. Org. Chem.* 35:4114-4117, American Chemical Society (1970).

Sartillo-Piscil, F., et al., "Fosfato-ésteres ciclicos diastereoisoméricos: 5-bromo-4-fenil-2-fenoxi-2-oxo-1,3,2-dioxafosforinanos, precursores de radicales libres alquilo β-fosfatoxi y generadores de radicales catiónicos en medio no oxidativo," *Revista de la Sociedad Quimica de México* 46:330-334, Sociedad Quimica de Mexico (2002).

Shaw, J.-P. and Cundy, K.C., "Biological Screens of PMEA Prodrugs," *Pharm. Res.* 10:S-294, Kluwer Academic Publishers B.V., Abstract No. PDD 7480 (1993).

Shih, Y.-E., et al., "Preparation and Structures of 2-Dimethylamino-4-phenyl-1,3,2-dioxaphosphorinane-2-oxides," *Bull. Inst. Chem., Academia Sinica* 41:9-16, Academia Sinica, Nankang, Taipei, Taiwan (1994).

Starrett, Jr., J.E., et al., "Synthesis, Oral Bioavailability Determination, and in Vitro Evaluation of Prodrugs of the Antiviral Agent 9-[2-(Phosphonomethoxy)ethyl]adenine (PMEA)," *J. Med. Chem.* 37:1857-1864, American Chemical Society (1994).

Thomson, W., et al., "Synthesis, Bioactivation and Anti-HIV Activity of the Bis(4-acyloxybenzyl) and Mono(4-acyloxybenzyl) Esters of the 5'-monophosphate of AZT," *J. Chem. Soc. Perk. Trans. 1*,1239-1245, Royal Society of Chemistry (1993).

Valentine, Jr., D., "Preparation of the Enantiomers of Compounds Containing Chiral Phosphorus Centers," *Asymmetric Synthesis* 4:263-312, Academic Press, Inc. (1984).

Venook, A., "Treatment of Hepatocellular Carcinoma: Too Many Options?," *J. Clin. Oncol.* 12:1323-1334, American Society of Clinical Oncology (1994).

Vo-Quang, Y., et al., "(1-Amino-2-propenyl)phosphonic Acid, an Inhibitor of Alanine Racemase and D-Alanine:D-Alanine Ligase," *J. Med. Chem.* 29:579-581, American Chemical Society (1986).

Wagner, A., et al., "Direct Conversion of Tetrahydropyranylated Alcohols to the Corresponding Bromides," *Tetrahedron Lett.* 30:557-558, Pergamon Press plc (1989).

Wallace, E.M., et al., "Design and Synthesis of Potent, Selective Inhibitors of Endothelin-Converting Enzyme," *J. Med. Chem.* 41:1513-1523, American Chemical Society (1998).

Walsh, E., et al., "Phenoxymethylphosphonic Acids and Phosphonic Acid Ion-exchange Resins," *Phenoxymethylphosphonic Acid Ion-Exchange Resins* 78:4455-4458, American Chemical Society (1956).

Watkins, P., "Noninvasive tests of CYP3A enzymes," *Pharmacogenetics* 4:171-184, Lippincott Williams & Wilkins (1994).

Weber, G.F. and Waxman, D.J., "Activation of the Anti-cancer Drug Ifosphamide by Rat Liver Microsomal P450 Enzymes," *Biochem. Pharm.* 45:1685-1694, Pergamon Press Ltd. (1993).

Weibel, M., et al., "Potentiating Effect of {2-[2-[(2-Amino-1,6-Dihydro-6-Oxo-9H-Purin-9-yl)Methyl]-Phenyl] Ethenyl}-Phosphonic Acid (MDL 74,428), A Potent Inhibitor of Purine Nucleoside Phosphorylase, on the Antiretroviral Activities of 2',3'-Dideoxyinosine Combined to Ribavirin in Mice," *Biochem. Pharmacol.* 48:245-252, Elsevier Science Ltd. (1994).

Wileman, T., et al., "Receptor-mediated endocytosis," *Biochem. J.* 232:1-14, Portland Press (1985).

Yu, L. J., et al., "In vivo Modulation of Alternative Pathways of P-450-Catalyzed Cyclophosphamide Metabolism: Impact on Pharmacokinetics and Antitumor Activity," *J. Pharmacol. Exp. Ther.* 288:928-937, The American Society for Pharmacology and Experimental Therapeutics (1999).

Zon, G., "Cyclophosphamide Analogues" in *Progress in Medicinal Chemistry*, Ellis, G.P., et al., eds., Elsvier Biomedical Press, Chapter 4, pp. 205-246 (1982).

Zon, G., et al., "NMR Spectroscopic Studies of Intermediary Metabolites of Cyclophosphamide. A Comprehensive Kinetic Analysis of the Interconversion of cis-and trans-4-Hydroxycyclophosphamide with Aldophosphamide and the Concomitant Partitioning of Aldophosphamide between Irreversible Fragmentation and Reversible Conjugation Pathways," *J. Med. Chem.* 27:466-485, American Chemical Society (1984).

International Search Report for related International Application No. PCT/US03/34690, European Patent Office, Netherlands, mailed Apr. 26, 2004.

Office Action for co-pending U.S. Appl. No. 10/698,924, Reddy, K.R., et al., filed Oct. 31, 2003, mailed Jun. 22, 2005.

Braess, J. et al. "Oral Cytarabine Octosfate in Acute Myeloid Leukemia and non-Hodgkin's Lymphoma—Phase I/II Studies and Pharmacokietics", *Leukemia* 12:1618-1626, Stockton Press (1998).

Chabner, B.A., "Cytidine Analogues", in *Cancer Chemotherapy: Principles and Practice*, Lippincott Williams & Wilkins (Apr. 1990).

Chabner, B.A., et al., "Purification and Properties of Cytidine Deaminase from Normal and Leukemic Granulocytes", *Journal of Clinical Investigation* 53:922-931, American Society for Clinical Investigation (Mar. 1974).

Cohen, S.S. "The Mechanisms of Lethal Action of Arabinosyl Cytosine (araC) and Arabinosyl Adenine (araA)", *Cancer* 40:509-518, Wiley (1977).

Grant, S., "Biochemical Modulation of Cytosine Arabinoside", *Pharmac. Ther.* 48:29-44, Pergamon Press plc (1990).

Leach, W.B. et al. "Toxicity Studies in Mice Treated with 1-β-D-Arabinofuranosyl-cytosine (ara-C)", *Cancer Research* 29:529-535, America Association for Cancer Research (Mar. 1969).

Plunkett, W. et al. "Pharmacologically Directed Ara-C Therapy for Refractory Leukemia", *Seminars in Oncology* 12(2) Supp. 3:20-30, W.B. Saunders (Jun. 1985).

Rustum, Y.M., et al. "1-β-Arabinofuranosylcytosine in Therapy of Leukemia: Preclinical and Clinical Overview" *Pharmac. Ther.* 56:307-321, Pergamon Press Ltd. (1992).

Shimma, N. et al., "The Design and Synthesis of a New Tumor-Selective Fluoropyrimidine Carbamate, *Capecitabine*" *Bioorganic & Medicinal Chemistry* 8:1697-1706, Elsevier Science Ltd. (2000).

Suto, T. et al., "The Effect of YNK-01 (an Oral Prodrug of Cytarabine) on Hepatocellular Carcinoma" *Seminars in Oncology* 24(2) Suppl 6:S6-122-S6-129, W.B. Saunders (Apr. 1997).

Yoshida, Y. et al., "Participation of the Peroxisomal β-Oxidation System in the Chain-Shortening of $PCA_{16}$, A Metabolite of the Cytosine Arabinoside Prodrug, YNK01, in Rat Liver" *Biochemical Pharmacology* 39(10):1505-1512, Pergamon Press plc (1990).

Sartillo-Piscil, F., et al., "Fosfato-ésteres cíclicos diastereoisoméricos: 5-bromo-4-fenil-2-fenoxi-2-oxo-1,3,2-dioxafosforinanos, precursores de radicales libres alquilo β-fosfatoxi γ generadores de radicales catiónicos en medio no oxidativo," *Rev. Soc. Quim. Mexico* 46:330-334, Journal of the Mexican Chemical Society (Dec. 2002).

English Translation of Sartillo-Piscil, F., et al., "Cyclic diastereoisomeric phosphate esters: 5-bromo-4-phenyl-2-phenoxy-2-oxo-1,3,2-dioxaphosphorinanes, free β-(phosphatoxy) alkyl radical precursors and cation radical generators in non-oxidative medium," *Rev. Soc. Quim. Mexico* 46:330-334, Journal of the Mexican Chemical Society (Dec. 2002).

Takaku, H., et al., "Synthesis of Deoxyribooligonucleotides Using Cesium Fluoride by the Phosphotriester Approach," *Nippon Kagaku Kaishi* (No. 10):1968-1973, The Chemical Society of Japan, Inc. (1985).

English translation of Takaku, H., et al., "Synthesis of Deoxyribooligonucleotides Using Cesium Fluoride by the Phosphotriester Approach," *Nippon Kagaku Kaishi* (No. 10):1968-1973, The Chemical Society of Japan, Inc. (1985).

Thuong, N.-T. and Chabrier, P., "Nouvelle méthode de préparation de la phosphorylcholine, de la phosphorylhomocholine et de leurs dérivés," *Bull. Soc. Chim. France 1-2*:667-671, Masson and Co. (1974).

English translation of Thuong, N.T. and Chabrier, P., "New Method for Preparation of Phosphoryl choline, of phosphoryl homocholine and their derivatives," *Bull. Soc. Chim. France 1-2*:667-671, Masson and Co. (1974).

Dialog File 351, Accession No. 11683821, WPI English language abstract of WO 97/49717.

Office Action for U.S. Appl. No. 11/145,194, Mark D. Erion et al., filed Jun. 3, 2005, mailed Mar. 24, 2006.

Boyer, S. et al., "The Discovery of MB07133: A HepDirect® Prodrug of Cytarabine Monophosphate for the Treatment of Hepatocellular Carcinoma," poster presentation at the American Chemical Society (ACS) Prospective, Boston, MA (May 2006).

Erion, M. et al., "HepDirect Prodrugs for Targeting Nucleotide-Based Antiviral Drugs to the Liver", *Current Opinion in Investigational Drugs* 7(2): 109-117, The Thomson Corporation (2006).

Ma, B, et al., "A Phase I/II Study to Assess the Safety, Tolerability and Pharmacokinetics (PK) of Intravenous (IV) Infusion of MB07133 in Subjects with Unresectable Hepatocellular Carcinoma (HCC) (Poster ID 2054, No. 19)," poster presentation at the American Society of Clinical Oncology (ASCO) Conference, Atlanta, Georgia (Jun. 2006).

Boyer, S.H. et al., "Synthesis and Characterization of a Novel Liver-Targeted Prodrug of Cytosine-1-β-D-arabinofuranoside Monophosphate for the Treatment of Hepatocellular Carcinoma," *J. Med. Chem.* 49:7711-7720, American Chemical Society (2006).

Figure 1a: Liver araCTP levels, when Compound A and Compound B are administered at a dose of 100 mg/kg CE to male NIH Swiss mice by a single i.p. bolus injection at time 0.

Figure 1b: Plasma prodrug levels, when Compound A and Compound B are administered at a dose of 100 mg/kg CE to male NIH Swiss mice by a single i.p. bolus injection at time 0.

Figure 1c: Plasma AraC levels, when Compound A and Compound B are administered at a dose of 100 mg/kg CE to male NIH Swiss mice by a single i.p. bolus injection at time 0.

Figure 2a: Liver ara-CTP levels in rat after prodrug administration by continuous i.v. infusion. Time course of liver araCTP levels in two independent studies evaluating activation of Compound A, B or C.

Figure 2b: Dose response of liver araCTP after treatment with Compound A or Compound B.

Figure 3a: Body weight, expressed as a percent of initial weight, as a function of time in mice treated with araC at doses of 30-1000 mg/kg CE for 5 days by daily IP injection. ). The * indicates $p<0.05$ compared with vehicle.

Figure 3b: Body weight, expressed as a percent of initial weight, as a function of time in mice treated with Compound C at doses of 30-1000 mg/kg CE for 5 days by daily IP injection.

Figure 4a: Hematology endpoints after 5-day treatment with araC (open circles) or Compound C (closed circles) relative to saline vehicle (closed squares). The * indicates $p<0.05$ compared with vehicle. Nucleated bone marrow cells.

Figure 4b: Hematology endpoints after 5-day treatment with araC (open circles) or Compound C (closed circles) relative to saline vehicle (closed squares). The * indicates $p<0.05$ compared with vehicle. Peripheral blood multinucleated cells (PMN's).

Figure 4c: Hematology endpoints after 5-day treatment with araC (open circles) or Compound C (closed circles) relative to saline vehicle (closed squares). The * indicates $p<0.05$ compared with vehicle. Peripheral blood mononuclear cells.

Figure 4d: Hematology endpoints after 5-day treatment with araC (open circles) or Compound C (closed circles) relative to saline vehicle (closed squares). The * indicates $p<0.05$ compared with vehicle. Platelets.

CYTARABINE MONOPHOSPHATE PRODRUGS

This application is a continuation application of U.S. application Ser. No. 10/698,928, filed Oct. 31, 2003, which claims the benefit of U.S. Provisional Application No. 60/423,259, filed Oct. 31, 2002, and U.S. Provisional Application No. 60/423,211, filed Oct. 31, 2002. Each of these applications is incorporated by reference herein in its entirety.

FIELD OF INVENTION

The present invention is directed toward certain novel cytarabine monophosphate (araCMP) cyclic diesters of 1,3 propane-1-aryl diols, to their preparation and to their uses More specifically, the invention relates to the area of cytarabine monophosphate (araCMP) cyclic diesters of 1,3 propane-1-(4-pyridyl) diols that have the cis stereochemistry.

BACKGROUND OF THE INVENTION

The following description of the background of the invention is provided to aid in understanding the invention, but is not admitted to be, or to describe, prior art to the invention. All publications are incorporated by reference in their entirety.

AraC is an analog of deoxycytidine, which is transported into cells via nucleoside transporters and phosphorylated to the active metabolite araC triphosphate (araCTP) by nucleoside and nucleotide kinases. It is one of the most-successful drugs used to treat acute nonlymphocytic leukemia, but it is ineffective in treatment against hepatocellular carcinoma ("HCC") because the necessary nucleoside kinase are expressed at low levels in the liver (Arner et al. *Pharmacol. Ther.* 67(2):155-86, (1995); Ruiz van Haperen et al. *Semin. Oncol.* 22 Suppl 11(4):35-41, (1995)). However, the kinase remains highly expressed in the target organs of toxicity (e.g. bone marrow) which leads to the associated dose-limiting toxicities. Cyclic prodrugs of araC offer the potential to improve effectiveness of araC in the liver by specifically delivering higher concentrations of araCTP to CYP3A4-expressing liver and HCC cells. The delivery of araC as its monophosphate, araCMP, is expected to bypass limiting deoxycytidine kinase, deoxycytidine deaminase and transport activities in both normal and resistant tumor cells. AraCMP cyclic diesters of 1,3-propane diols are therefore predicted to have increased anti-tumor activity in the liver, compared to araC, with reduced toxicity to the extra-hepatic hematopoietic system, which leads to dose-limiting myelosuppresion seen in man (See U.S. Pat. No. 6,312,662).

Hepatitis and liver cancer remain poorly treated with current therapies due to dose-limiting extrahepatic side effects or inadequate delivery of chemotherapeutic agents to the target tissue. Limitation in present approaches include drug loading capacity, complexity of the manufacture and characterization of the conjugate, and receptor down regulation. Thus, there is still a need for a way to deliver drugs such as araC to the liver.

SUMMARY OF THE INVENTION

Figure 1A:
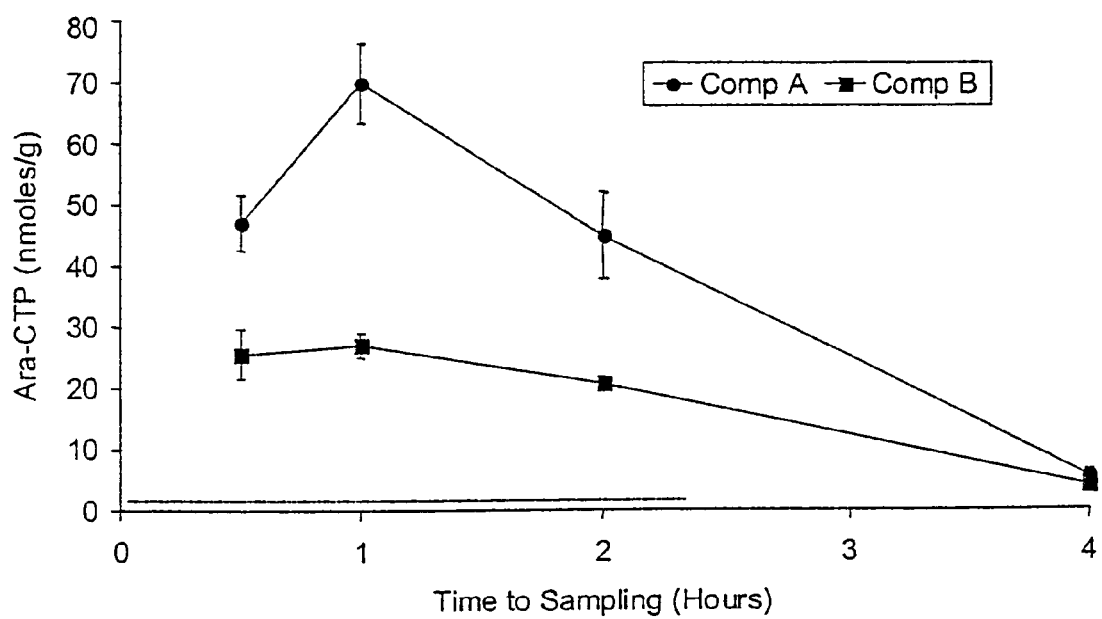
FIG. 1a. Depicts the level of araCTP in the liver when Compound A and Compound B are administered at a dose of 100 mg/kg CE to male NIH Swiss mice by a single i.p. bolus injection at time 0.

The present invention is directed toward certain novel cytarabine monophosphate (araCMP) cyclic diesters of 1,3 propane-1-aryl diols, to their preparation and to their uses More specifically, the invention relates to the area of cytarabine monophosphate (araCMP) cyclic diesters of 1,3 propane-1-(4-pyridyl) diols that have the cis stereochemistry.

One aspect of the invention relates to compounds of Formula I:

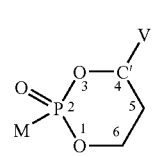

Formula I wherein:

M and V are cis to one another and MH is cytarabine;

the 5' oxygen of said cytarabine is attached to the phosphorus;

V is 4-pyridyl;

and pharmaceutically acceptable prodrugs and salts thereof.

In another aspect, the invention relates to the compound of Formula III.

Formula III

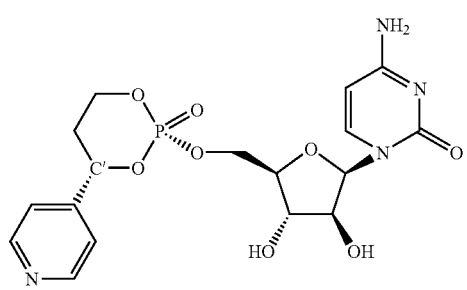

and pharmaceutically acceptable salts and prodrugs thereof.

Another aspect of the invention relates to the methods for the preparation of compounds of Formula III:

Formula III

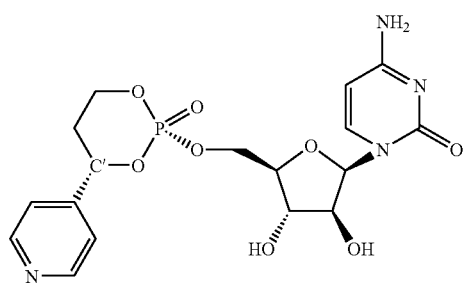

wherein:

the 5' oxygen of cytarabine is attached to the phosphorus which comprises coupling a phosphorylating reagent of Formula IV and optionally protected cytarabine;

Formula IV

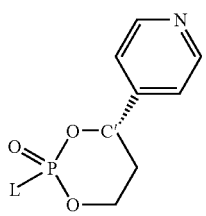

wherein L is selected from the group consisting of chloro, and 4-nitrophenoxy.

Definitions

In accordance with the present invention and as used herein, the following terms are defined with the following meanings, unless explicitly stated otherwise.

The term "cis" stereochemistry refers to the relationship of the V group and M group positions on the six-membered ring. The formula below shows a cis stereochemistry.

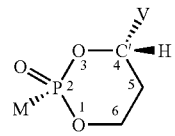

Another cis stereochemistry would have V and M pointing above the plane. The formula below shows this cis stereochemistry.

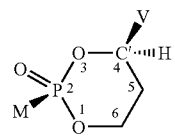

The terms "S-configuration", "S-isomer" and "S-prodrug" refers to the absolute configuration S of carbon C'. The formula below shows the S-stereochemistry.

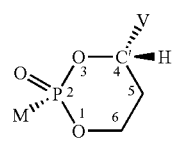

The terms "R-configuration", "R-isomer" and "R-prodrug" refers to the absolute configuration R of carbon C'. The formula below shows the R-stereochemistry.

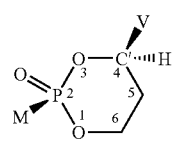

The term "percent enantiomeric excess (% ee)" refers to optical purity. It is obtained by using the following formula:

$$\frac{[R]-[S]}{[R]+[S]} \times 100 = \%R - \%S$$

where [R] is the amount of the R isomer and [S] is the amount of the S isomer. This formula provides the % ee when R is the dominant isomer.

The term "stereogenic center" refers to

The term "d.e." refers to diastereomeric excess. It is obtained by using the following formula:

$$\frac{[cis]-[trans]}{[cis]+[trans]} \times 100 = \%[cis] - \%[trans]$$

The term "diastereoisomer" refers to compounds with two or more asymmetric centers having the same substituent groups and undergoing the same types of chemical reactions wherein the diasteroismers have different physical properties, have substituent groups which occupy different relative positions in space, and have different biological properties.

The term "racemic" refers to a compound or mixture that is composed of equal amounts of enantiomeric molecular forms of the molecule is not optically active.

The term "enantiomer" refers to either of a pair of molecules whose molecular structures have a mirror-image relationship to each other.

The term "halogen" refers to chloride, bromide, iodide, or fluoride.

The term "alkyl" refers to saturated aliphatic groups including straight-chain, branched chain and cyclic groups. Suitable alkyl groups include methyl, ethyl, isopropyl, and cyclopropyl.

The term "aryl" refers to aromatic groups which have 5-6 ring atoms. Suitable aryl groups include phenyl, furanyl, pyridyl, and thienyl. Aryl groups may be substituted.

The term "aryloxy-" refers to the group aryl-O—.

The term "lower" referred to herein in connection with organic radicals or compounds respectively defines such as with up to and including 10, preferably up to and including 6, and advantageously one to four carbon atoms. Such groups may be straight chain, branched, or cyclic.

The term "optionally substituted" or "substituted" includes aryl groups substituted by one to two substituents, independently selected from lower alkyl, lower aryl, and halogens. Preferably these substituents are selected from the group consisting of halogens.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucoronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl-sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terephthalic acid, and p-toluenesulfonic acid.

The term "prodrug" as used herein refers to any M compound that when administered to a biological system generates a biologically active compound as a result of spontaneous chemical reaction(s), enzyme catalyzed chemical-reaction(s), and/or metabolic chemical reaction(s), or a combination of each. Standard prodrugs are formed using groups attached to functionality, e.g., HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl as well, as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, and antiviral agents. Certain prodrugs of cytarabine, e.g. $N^4$— acylated cytarabine (Wechter et al., *J. Med. Chem.* 19(8), 1013 (1976)) wherein the acylated group is palmitoyl or behanoyl, are known to increase lipid solubility and membrane transport as well as decrease deamination by cytidine deaminase. Other groups at $N^4$— are also envisioned such as alkylidene (i.e., an imino group). These groups are removed in vivo to generate the 4-amino group of cytarabine. Similar prodrugs are envisioned for the prodrugs of this invention.

The term "cyclic 1', 3'-propane ester", "cyclic 1, 3-propane ester", "cyclic 1', 3'-propanyl ester", and "cyclic 1, 3-propanyl ester" refers to the following:

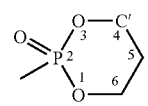

The term "4-pyridyl", "pyrid-4-yl" and "4-pyridinyl" refer to the following:

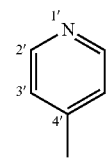

The term "5' oxygen" refers to the oxygen in the following:

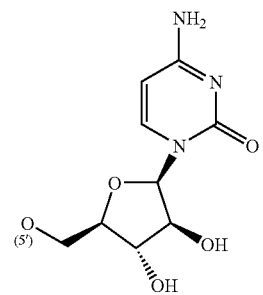

The term "N-containing heteroaryl solvent" is a heteroaryl group with 1 to 3 nitrogens as ring atoms and a 4<pka<6 and any mixture with non N-containing heteroaryl solvents.

The term "N-hydroxy-nitrogen-containing heteroaryl" refers to a N-containing heteroaryl where a hydroxy group is attached to a nitrogen atom. An example is N-hydroxy-benzotriazole.

The term "N-containing heteroaryl" refers to heteroaryl group with 1 to 3 nitrogens as ring atoms and attached via a carbon atom.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, Advanced Organic Chemistry, McGraw Hill Book Company, New York, (1977 edition) pp. 251-259. The Hammett constant values are generally negative for electron donating groups ($\sigma_p=-0.66$ for $NH_2$) and positive for electron withdrawing groups ($\sigma_p=0.78$ for a nitro group), $\sigma_p$ indicating para substitution. Exemplary electron-withdrawing groups include nitro, ketone, aldehyde, sulfonyl, trifluoromethyl, —CN, chloride, and the like.

The term "leaving group" refers to the part of the substrate molecule which when cleaved in a reaction does not contain the phosphorus that was supplied to the bond during the reaction.

The term "P450" refers to the cytochrome P-450. P450 enzymes are found in large amounts in the liver and other tissues containing these enzymes. Specific P450 isozymes are responsible for oxidizing the cyclic phosphonate of the present invention so that the free phosphonate or phosphate is ultimately produced. P 450 enzymes are found in tissues and cells of all mammals.

The term "P450-expressing tissues" refers to the liver and to like tissues and cells that contain the CYP3A4 isozyme or any other P450 isozyme found to oxidize the cyclic prodrugs of the invention. According to DeWaziers et al. (*J. Pharm. Exp. Ther.*, 253, 387-394 (1990), CYP3A4 is located in humans in the following tissues (determined by immunoblotting and/or enzyme measurements):

| Tissues | % of liver activity |
| --- | --- |
| Liver | 100 |
| Duodenum | 50 |
| jejunum | 30 |
| ileum | 10 |
| colon | <5 (only P450 isoenzyme found) |
| stomach | <5 |
| esophagus | <5 |
| kidney | not detectable |

The term "diseases of P450-expressing tissues" refer to diseases, where the function of P450-expressing tissues is compromised such that the tissues are no longer able to perform their metabolic functions. This can result in either an overproduction or decrease in biochemical end products. These diseases may include disease of the liver such as primary or metastatic liver cancer (e.g. HCC), liver fibrosis, or cirrhosis; diseases that may involve the liver, but may also involve other P450-expressing tissues may include primary or metastatic colorectal cancer, hyperlipidemia, diabetes, and viral and parasitic infections.

The term. "optionally protected cytarabine" refers to protection of the 2 ' and 3' hydroxyl groups and the 4-nitrogen group of cytarabine by standard protecting groups.

The term "enhancing" refers to increasing or improving a specific property.

The term "enriching" refers to increasing the quantity of a specific isomer produced by a reaction.

The term "administered simultaneously" refers to the administration of one drug at or near the same time in which another drug is administered. Preferably administration is within 30 minutes of one another.

The term "therapeutic index" ("TI") refers to the ratio of the dose of a drug or prodrug that produces a therapeutically beneficial response relative to the dose that produces an undesired response such as death, an elevation of markers that are indicative of toxicity, and/or pharmacological side effects.

The term "remission" refers to the abatement or lessening in severity of the symptoms of a disease.

The term "cancer-free" refers to the lack of evidence indicating the presence of malignant neoplasms (cancers) or metastases in any tissue or organ.

The following well known chemicals are referred to in the specification and the claims. Abbreviations and common names are also provided.

$CH_2Cl_2$; Dichloromethane or methylene chloride
DCM; dichloromethane or methylene chloride
(−)-DIP-Cl; (−)-β-Chlorodiisopinocampheylborane
DMAP; 4-dimethylaminopyridine
DMF; Dimethylformamide
DMPU; 1,3-dimethyl-3,4,5,6-tetrahydro-2(1H)-pyrimidinone
DMSO; dimethyl sulfoxide
HCl; hydrochloric acid
KI; potassium iodide
$MgSO_4$; magnesium sulfate
MTBE; t-butyl methyl ether
NaCl; sodium chloride
NaOH; sodium hydroxide
P450; cytochrome P-450;
PyBOP; benzotriazol-1-yloxytripyrrolidinophosphonium hexafluorophosphate
TBDMSCI; TBSCI; t-butyldimethyl chlorosilane
TBS; TBDMS; t-butyldimethylsilyl
TEA; triethylamine
THF; tetrahydrofuran
TMSCI; chlorotrimethylsilane
5'-O-cis-[4-(4-pyridyl)-1,3,2-dioxaphosphorin-2-oxo-2-yl]-cytosine-β-D-arabinofuranoside; 2(1H)-Pyrimidinone, 4-amino-1-[5-O-cis-[2-oxido-4-(4-pyridinyl)-1,3,2-dioxaphosphorinan-2-yl]-β-D-arabinofuranosyl]

The following well known drug is referred to in the specification and the claims. Abbreviations and common names are also provided.

Cytarabine; 1-(β-D-Arabinofuranosyl)cytosine; araC

DETAILED DESCRIPTION OF THE INVENTION

This invention is directed to the discovery of 5'-O-cis-[4-(4-pyridyl)-1,3,2-dioxaphosphorin-2-oxo-2-yl]-cytosine-β-D-arabinofuranoside compounds and their use in treating diseases of the liver. In one aspect, diseases of the liver are selected from the group consisting of viral infections and cancers of the liver. In another aspect, cancer of the liver is hepatocellular carcinoma. In a secondary aspect, cancer of the liver is colorectal carcinoma. In one aspect, the isomer of the 5'-O-cis-[4-(4-pyridyl)-1,3,2-dioxaphosphorin-2-oxo-2-yl]-cytosine-β-D-arabinofuranoside compounds is the isomer where carbon C' has the S configuration. In another aspect, the present invention is also directed towards the process for the synthesis of 5'-O-cis-[4-(4-pyridyl)-1,3,2-dioxaphosphorin-2-oxo-2-yl]-cytosine-β-D-arabinofuranoside compounds. The process of this invention is directed towards the synthesis of both cis-stereoisomers of the cyclic phosphate diesters of araCMP. In one aspect, the cis-isomer of the cytarabine phosphate diesters is the cis-isomer of the cytarabine phosphate diesters with the S-configuration at the C' carbon.

Very few procedures have shown to be efficacious in curing liver cancer. In a small percentage of patients, where tumors are very well defined and very few, surgical ablation, cryoablation and ethanol injections, have shown limited efficacy in curing the patients. However, the majority of the patients that do undergo these procedures end up getting recurrence of the cancer. In another aspect, this invention is also directed towards preventing recurrence of cancers in P450-expressing tumors in patients that underwent medical or surgical treatment.

In another aspect of the invention, the preferred prodrugs of the invention are used to treat metastatic cancers. In one aspect, metastatic cancers are selected from secondary cancers derived from colorectal cancers.

Method for Treating Recurrent Cancers

Hepatocellular carcinoma patients are identified and monitored using a variety of techniques, including ultrasonography, computed tomography (CT), magnetic resonance imaging, angiography, and biopsy. Alpha fetoprotein (AFP) levels are used at diagnosis and can be a good indicator of antitumor activity, especially in patients with high initial AFP levels. These techniques are often useful in determining treatment options and patient eligibility. Treatment options include, orthotopic liver transplantation (OLT), surgical resection, percutaneous injection of various agents (including alcohol), cryotherapy, intra-arterial chemotherapy, transcatheter arterial chemoembolization (TACE), systemic chemotherapy, radiotherapy, immunotherapy and hormone therapy. Tumors <1 cm usually cannot be diagnosed. Patients undergoing a surgical procedure (OLT or surgical resection) may show no observable evidence of tumors following the procedure. Similarly, patients undergoing non-surgical treatments such as ablation therapy (ethanol, microwave, radiofrequency) and TACE may also show significant decreases in tumor size and appear to be tumor free. Patients may also be treated with microspheres (radiolabeled micro glass beads with Yttrium-90), drug delivery vehicles such as microparticles composed of iron that can be positioned with external magnets to the tumor, direct injection of a chemotherapy agents, e.g. cisplatin in a gel, drugs targeting HCC tumors such as doxorubicin and the use of chemo agents (like doxorubicin) in ethanol ablation. Other chemotherapy agents are also viewed as potential initial systemic therapy treatments, including anti-angiogenesis agents, thymidylate synthase inhibitors (e.g., thymitaq), tubulin polymerization inhibitors (e.g., T67), various topoisomerase I inhibitors, e.g., drugs from the tecan class such as exatecan, various drug combination including a combination of cisplatin, interferon, adriamycinan and 5-FU.

All treatments of HCC are associated with a high incidence of cancer recurrence. Recurrent cancer may arise for one or more reasons. For example, secondary intrahepatic metastases that are present at the time of surgery are often undetected because of their size (<1 cm). Patients with portal or hepatic vein invasion have a poor prognosis since the tumor may have seeded other liver lobes. These micro metastases grow in size and proliferate and are particularly susceptible to prodrugs of this invention. A second factor that can lead to recurrent disease arises from incomplete tumor resection or ablation of the primary tumor(s). A third factor relates to the environment of the liver (cirrhotic, viral infection) which can make the liver a high risk for "new" primaries some of which may be present but undetected at the time of the treatment.

To prevent or delay recurrent cancer, prodrugs of the invention are envisioned to be used prior to, during or following one of the above treatments. The treatment entails administration of a prodrug of the invention to an HCC patient for one to 10 cycles, preferably three to six cycles over the course of one to two years. A cycle entails a course of treatment shown to be effective in slowing or preventing tumor growth. In one aspect of the invention the treatment entails the continuous infusion of a prodrug for 7-14 days followed by at least a 14 day drug free period (one cycle). Patients are monitored over time. Prodrugs result in increased cancer free time, increased survival time, and/or improved quality of life.

Method for Treating Leukemia

Cytarabine is used to treat various leukemias. Typically, cytarabine is administered at doses of 100 to 200 $mg/m^2$/day by either continuous infusion for up to 7 days followed by a several week drug free period as a result of the cytarabine-induced myelosuppression. Typically three or more cycles are used to treat leukemia patients. High dose regimens have also been employed (e.g. 3 $gm/m^2$) for various reasons. Overall higher drug levels are required due to rapid metabolism of cytarabine that principally entails deamination of araC to the inactive metabolite araU. Prolonged delivery is considered optimal for treating cancers with cell cycle-dependent oncolytics such as cytarabine. Cytarabine is at least in part effective through its ability to inhibit DNA synthesis either through its ability to inhibit DNA polymerase and/or result in chain termination of a growing DNA strand following DNA polymerase catalyzed incorporation. As an inhibitor of DNA synthesis, araC has its greatest cytotoxic effects during the S-phase of the cell cycle perhaps due to the requirement for its incorporation into DNA and the greater activity of anabolic enzymes during the S-phase. Consequently, the duration of exposure of cells to araC is directly correlated with cell kill because the longer exposure period allows araC to be incorporated into the DNA of a greater percentage of cells as they pass through S-phase.

Patients treated with higher doses or araC or for prolonged periods are at risk for various araC-associated toxicities; In addition certain patients may be particularly at risk to cytarabine toxicities, e.g. liver impaired patients, elderly. Toxicities include myelosuppression, gastrointestinal epithelial ulceration, intrahepatic cholestasis and pancreatitis, cerebellar and cerebral dysfunction, and conjunctivitis.

Prodrugs of the invention are envisioned to diminish some of these dose-limiting toxicities. In particular, araC, produced in and released from the liver following prodrug activation will provide a method for achieving antileukemic activity with fewer toxicities. Steady state levels can be achieved with prodrugs of the invention without achieving high peak levels that can give rise to toxicities such as cerebellar and cerebral dysfunction, and conjunctivitis. The prodrug also provides a means in which to administer cytarabine that diminishes injection site-associated adverse events. Sustained release of cytarabine from the prodrug can change the dosing regimen from continuous infusion to i.v. bolus or short infusion, s.c., i.m. oral, etc. Myelosuppression may still be associated with the therapy. A variety of mechanisms can be used to diminish the effects of the myelosuppressive activity of the prodrugs, including a drug holiday, bone marrow transplantation, or agents that increase the myeloid hematopoietic cell activation, e.g. IL-3, GM-CSF, G-CSF, epoetin).

Increased Therapeutic Index

Several toxicities are also associated with nearly all anti-cancer agents. In an effort to decrease these toxicities during treatment of primary or secondary liver cancers, drugs are sometimes administered directly into the portal artery in order to increase liver drug exposure. Since oncolytic drugs typically are associated with significant side effects, local administration enables greater hepatic uptake and thereby decreased extrahepatic toxicities. To further increase liver uptake, chemoembolization is sometimes used in conjunction with hepatic artery drug infusion. The high liver specificity of the prodrugs in the current invention suggest that systemic side effects will be similarly minimized by the novel prodrug approach.

Moreover, primary and secondary liver cancers are particularly resistant to both chemotherapy and radiotherapy. Although the mechanism for the resistance is not completely understood, it may arise from increased liver gene products that lead to rapid metabolism and/or export of chemotherapeutic agents. In addition, the liver, which is generally associated with xenobiotic metabolism and generation of cytotoxic intermediates, is equipped by nature with multiple protective mechanisms so that damage from these intermediates is minimized. For example, the intracellular concentration of glutathione is very high in the liver relative to other tissues presumably so that intermediates capable of alkylating proteins and DNA are detoxified through a rapid intracellular reaction. Consequently the liver may be resistant to chemotherapeutic agents because of these mechanisms and therefore require higher than normal concentrations of the oncolytic agent to achieve success. Higher liver concentrations require higher doses of the drug which commonly result in extrahepatic toxicities.

The prodrugs of this invention can significantly increase the therapeutic index ("TI") of cytarabine. In many cases, the increased TI is a result of the high liver specificity. For example, cytarabine is poorly phosphorylated in the liver due to low levels of kinases. However, the kinase remains highly expressed in the target organs of toxicity (e.g., bone marrow) which leads to the associated dose-limiting toxicities. Therefore cyclic prodrugs of araC offer the potential to improve effectiveness of araC in the liver by specifically delivering much higher concentrations of araCTP to CYP3A4-expressing liver and HCC cells.

The high liver specificity of prodrug cleavage implies that the by-product of prodrug cleavage is also primarily produced in the liver. Accordingly, toxicities associated with the by-product are minimized since the by-product frequently undergoes rapid detoxification reactions that either eliminate or minimize by-product toxicity. For example, reactions between the by-product and compounds and/or proteins present in the hepatocytes (e.g., glutathione and the $\alpha,\beta$-unsaturated olefin generated by the prodrug's breakdown). Moreover, enzymes present in the liver may also further transform the by-product into a non-toxic compound (e.g., oxidation and/or sulfation of hydroxypyridine, or reduction of the $\alpha,\beta$-unsaturated ketone, etc.). In addition, intramolecular reactions that involve cyclization reactions between a reactive group and the $\alpha,\beta$-unsaturated carbonyl-containing compound generated by the prodrug's breakdown can minimize by-product toxicity.

The cytotoxicity of the prodrugs are readily evaluated using cell lines that lack P450 activity (e.g., CYP3A4 activity).

Increased TI can also be achieved by delivery of greater amounts of the biologically active agent to the liver relative to the equivalent doses of the parent drug. Increased liver levels of the biologically active agent are achieved by administration of prodrugs together with agents that induce P450 activity, e.g., CYP3A4 activity (e.g., rifampicin, glucocorticoids, phenobarbital, erythromycin).

Method of Improving Prodrug Stability

Compound stability in biological systems is crucial for the development of a prodrug of a cytotoxic drug like cytarabine. For example, a lack of stability to the enzymes present in the plasma will lead to the breakdown of the active compound in the plasma instead of the targeted CYP3A4-expressing tissue and will consequently decrease the TI hoped to be achieved by a prodrug strategy. Similarly, a lack of intrinsic stability in aqueous medium will lead to the breakdown of the prodrug not only in plasma but in any organ the prodrug may distribute into, again leading to a decrease in TI. In addition, a lack of stability may impair drug development as it will make the final formulation of the active compound more difficult, especially if the prodrug is to be used parenterally. In one aspect, this invention is directed towards the use of 1-(4-pyridyl)-1,3-propane diol prodrugs of araCMP in order to improve the overall stability of the prodrugs of araCMP. In one aspect, prodrugs of araCMP are the cis-(4-pyridyl) prodrugs of araCMP. In another aspect, the prodrug of araCMP is the cis-(4-pyridyl) prodrug of araCMP where carbon C' has the S configuration.

The stability of the prodrugs is readily determined by monitoring the breakdown of the prodrugs in biological fluids, such as plasma, and solutions buffered at several pHs and with different buffering agents.

Improved Pharmacodynamic Half-Life

The pharmacodynamic half-life of cytarabine can be extended by the novel prodrug methodology as a result of both its ability to produce the drug over a sustained period and in some cases the longer pharmacokinetic half-life of the prodrug. Both properties can individually enable therapeutic drug levels to be maintained over an extended period resulting in an improvement in the pharmacodynamic half-life. The pharmacodynamic half-life can be extended by impeding the metabolism or elimination pathways followed by the parent drug. For some drugs, the prodrugs of the present invention are able to impede the metabolism or elimination pathways followed by the parent drug and thereby exist for extended periods in an animal. For example, cytarabine is a substrate for the metabolic enzyme cytidine deaminase, that converts cytidine to uridine, and as such, cytarabine is converted to arabinofuranosyluracil. However, the prodrugs of araCMP are not substrates for this enzyme and consequently lead to a longer pharmacodynamic half-life of cytarabine compare to the direct administration of cytarabine.

A common route of elimination of phosphate drugs is via the kidneys and a transporter that recognizes anionic compounds. Complete elimination of phosphate containing drugs from the circulation often occurs only minutes after drug administration. The prodrugs of this invention slow the elimination of the drug by removing the negative charge until after oxidation and hydrolysis in liver and like tissues.

Formulations

Compounds of the invention are administered in a total daily dose of about 0.1 mg/kg to about 100 mg/kg, preferably from about 1 mg/kg to about 30 mg/kg. The most preferred dose range is about 10 mg/kg/day. The dose may be administered in as many divided doses as is convenient.

Compounds of this invention when used in combination with other antiviral agents or oncolytic agents may be administered as a daily dose or an appropriate fraction of the daily dose (e.g., bid). Administration of the prodrug may occur at or near the time in which the other antiviral or oncolytic agent is administered or at a different time. The compounds of this invention may be used in a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

Prodrugs of the invention can be combined with various agents to further enhance efficacy and/or diminish cytarabine-associated toxicity. Various combinations can be envisioned that would increase the effectiveness of the therapy. Combination with drugs known to be effective against cancer could help treat metastases that have escaped the liver and are not responsive to the prodrug therapy. Such agents include drugs selected from the group of well known chemotherapy agents, including inhibitors of DNA synthesis (DNA polymerase inhibitors, inhibitors of de novo pyrimidine pathway (e.g. thymidylate synthase inhibitors, dihydroorotate dehydrogenase inhibitors, aspartate carbamoyltransferase inhibitors), folate antimetabolites (e.g. dihydrofolate reductase inhibitors, folypolyglutamate synthetase inhibitors), inhibitors of purine biosynthesis (inosine 5'-monophosphate dehydrogenase inhibitors, glycinamide ribonucleotide formyltranferase inhibitors, ribonucleoside diphosphate reductase inhibitors, inhibitors of polyamine biosynthesis (e.g. inhibitors of S-adenosyl-L-methionine decarboxylase, ornithine decarboxylase, spermidine/spermine N-acetyltransferase), antitumor antibiotics, plant alkaloids, farnesyl transferase inhibitors, topoisomerase inhibitors, platinum-based drugs, antiangiogenesis drugs, tubulin polymerase inhibitors, etc.

Various well known drug classes are envisioned as suitable for combination with prodrugs of this invention, including Epipodophyllotoxins, Camptothecins, Anthracyclines, Anthrapyrazoles, Combretastatin Analogs, Enediyine antibiotics, Taxanes.

In one aspect of the invention, epipodophyllotoxins are preferred including Etoposide, Teniposide, NK-611, GL-331, and azatoxin. In one aspect epipodophyllotoxins are Etoposide and Teniposide. In one aspect Camptothecins are preferred including Camptothecin, Topotecan, Irinotecan (CPT-11), Lurtotecan (GI 147211), 9-aminocamptothecin, GG-211, DX-8951F, SKF 107874, and SKF 108025. In another aspect, Camptothecins include Camptothecin, Topotecan, Irinotecan, Lurtotecan, and 9-aminocamptothecin. In another aspect, Camptothecins include Topotecan and Irinotecan. In one aspect, Taxanes include paclitaxel, docetaxel, and FCE-28161. In another aspect, Taxanes include paclitaxel. In one aspect, combretastatins include combretastain A-4 and the reported (S,S) dioxolane analog (*Bioorg. Med. Chem. Lett.* 88: 1997-2000 (1998). In one aspect, anthrapyrazoles include mitoxantrone, piroxantrone, and Losoxantrone. In one aspect, Anthracyclines include Doxorubicin, Daunorubicin, Idarubicin, Pirarubicin, plicamycin, valrubicin, dactinomycin and Epirubicin. In another aspect, Anthracyclines are Doxorubicin, Pirarubicin, Epirubicin, and Idarubicin. In another aspect, Anthracyclines include Pirarubicin and Doxorubicin. In one aspect, Enediyne Antibiotics include neocarzinostatin, calicheamicin, and esperamicin. In another aspect, Enediyne Antibiotics include Neocarzinostatin and Calicheamicin, Dynemicin. In one aspect, DNA damaging drugs such as alkylating agents (nitrogen mustards, aziridines), nitrosoureas, and metal complexes are used. In one aspect, mitomycin is preferred. In one aspect, platinum complexes include cisplatin, nedaplatin, miriplatin, and carboplatin. In one aspect alkylating agents include cyclophosphamide, ifosfamide. In one aspect, nitrosourea include carmustine (BCNU), temozolomide. In one preferred aspect of the invention, cell cycle-dependent inhibitors are preferred including 5-FU, doxifluridine, gemcitabine, cladribine, fludarabine. In one aspect, folate antimetabolites include methotrexate. In another aspect, oncolytic drugs useful in combination with prodrugs of this invention include busulfan, thiotepa, melphalane, luroteca.

In one aspect, agents that act synergistic with cytarabine are used. These agents include alkylating agents such as cyclophosphamide, ifosfamide, carmustine (BCNU), cisplatin, mercaptopurine, thioguanine, methotrexate, 6-thioguanine, and 3-deazauridine.

In another aspect, prodrugs of the invention are combined with drugs known to stimulate progression of the cell cycle to the S-phase and thereby make them more susceptible to prodrugs of the invention.

In another aspect, prodrugs of the invention are combined with drugs known to stimulate apoptosis. Such drugs include caspase-3 inhibitors.

The combined therapy entails administration to the host the agents either separately or simultaneously. In one aspect, the prodrug is administered simultaneously with the oncolytic drug. The drugs can be administered in the same vehicle or separately. Both drugs can be parenterally administered (including subcutaneous, intramuscular, intravenous and intradermal), or by other routes, including oral, rectal, nasal, topical, vaginal, and transdermal. In one aspect, both agents are administered simultaneously in either the same capsule or as separate pills. In another aspect, both agents are administered during meal time (just prior to feeding or just after feeding). In another aspect, the drug combination is administered at separate times. In one aspect, drug administration is separated in time but during the period of the cycle therapy. In another aspect, one drug is administered during the drug holiday for the partner drug.

The oncolytic agents or antiviral agents and the compounds of this invention may be administered separately or may be administered simultaneously. Suitable oncolytic agents include busulfan, carboplatin, cisplatin, miriplatin, temozolomide, thiotepa, melphalan, ifosfamide, cyclophosphamide, chlorambucil, doxorubicin, daunorubicin, epirubicin, idarubicin, plicamycin, valrubicin, dactinomycin, gemcitabine, floxuridine, fluorouracil, mercaptopurine, thioguanine, methotrexate, mitomycin, etoposide, paclitaxel, docetaxel, irinotecan, topotecan, etoposide, teniposide, nedaplatin, carmustine, doxifluridine, cladribine, fludarabine, azatoxin, camptothecin, lurtotecan, 9-aminocamptothecin, pirarubin, neocarzinostatin, calicheamicin, esperamicin, and luroteca.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Intravenous administration is generally preferred.

Pharmaceutically acceptable salts include acetate, adipate, besylate, bromide, camsylate, chloride, citrate, edisylate, estolate, fumarate, gluceptate, gluconate, glucoranate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalyicylate, tannate, tartrate, terphthalate, tosylate, and triethiodide.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-beoate, one (or more coloring agents, one or more flavoring agents and one or more sweetening agents, such as sucrose or saccharin.

Oil suspensions may be formulated by suspending the active ingredient in a vegetable oil, such as arachid oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachid oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 µmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 µmol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for parenteral administration may be administered in a continuous infusion manner via an indwelling pump or via a hospital bag. Continuous infusion includes the infusion by an external pump. The infusions may be done through a Hickman or PICC or any other suitable means of administering a formulation either parenterally or i.v.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Compounds Prepared by the Invention

The compounds and intermediates prepared by the invention are 6-membered cyclic phosphate diester prodrugs of araCMP as represented by Formula I:

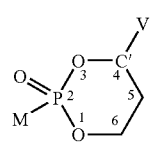

Formula I wherein:
M and V are cis to one another and MH is cytarabine;
the 5' oxygen of said cytarabine is attached to the phosphorus;
V is 4-pyridyl;
and pharmaceutically acceptable prodrugs and salts thereof.

Another aspect of the invention is the preparation of the compounds of Formula II

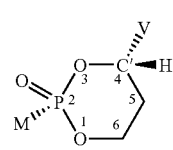

Formula II wherein:
MH is cytarabine attached to the phosphorus in Formula II via an oxygen atom at the 5' hydroxyl position;
V is 4-pyridyl;
and pharmaceutically acceptable prodrugs and salts thereof.

Another aspect of the invention is the preparation of the compound as represented by Formula III and pharmaceutically acceptable prodrugs and salts thereof.

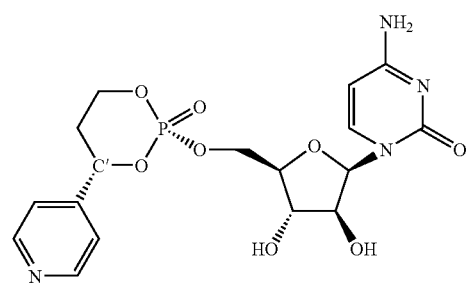

Formula III 1.0 Synthesis of Phosphorylating Reagent:

A variety of synthetic methods are known to prepare 1,3-diols. These suitable methods are divided into two types as follows: 1) synthesis of racemic 1-(aryl)-propane-1,3-diol; 2) synthesis of enantioenriched 1-(aryl)-propane-1,3-diol.

1.1 Synthesis of Racemic 1-(Aryl)-Propane-1,3-Diol:

1,3-Dihydroxy compounds can be synthesized by several well known methods from the literature. Substituted aromatic aldehydes are utilized to synthesize racemic 1-(aryl)propane-1,3-diol via addition of lithium enolate of alkyl acetate followed by ester reduction (path A) (Turner, *J. Org. Chem.* 55:4744 (1990)). Alternatively, aryl Grignard additions to 1-hydroxy propan-3-al also give 1-(arylsubstituted)propane-1,3-diols (path B). This method will enable conversion of various substituted aryl halides to 1-(arylsubstituted)-1,3-propane diols (Coppi, et al., *J. Org Chem.* 53:911 (1988)). Aryl halides can also be used to synthesize 1-substituted propane diols by Heck coupling of 1,3-diox-4-ene followed by reduction and hydrolysis (Sakamoto, et al., *Tetrahedron Lett.* 33:6845 (1992)). Pyridyl, quinoline, isoquinoline propan-3-ol derivatives can be oxygenated to 1-substituted-1,3-diols by N-oxide formation followed by rearrangement in acetic anhydride conditions (path C) (Yamamoto, et al., *Tetrahedron* 37:1871 (1981)). A variety of aromatic aldehydes can also be converted to 1-substituted-1,3-diols by vinyl Grignard addition followed by hydroboration reaction (path D).

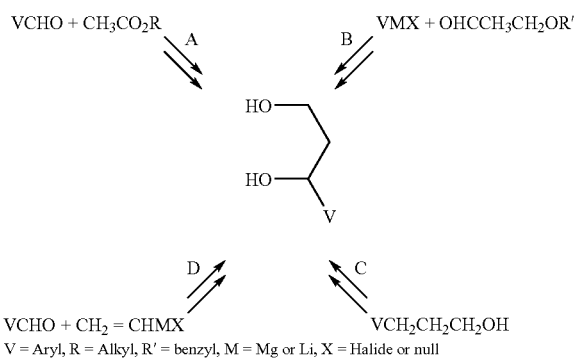

V = Aryl, R = Alkyl, R' = benzyl, M = Mg or Li, X = Halide or null 1.2 Synthesis of Enantioenriched 1-(aryl)-Propane-1,3-Diol:

A variety of known methods for separation of secondary alcohols via chemical or enzymatic agents may be utilized for preparation of diol enantiomers (Harada, et al., *Tetrahedron Lett.* 28:4843 (1987)). Transition metal catalyzed hydrogenation of substituted 3-aryl-3-oxo propionic acids or esters is an efficient method to prepare R or S-isomers of beta hydroxy acids or esters in high enantiomeric purity (*Comprehensive Asymmetric Catalysis*, Jacobsen, E. N., Pfaltz, A., Yamamoto, H. (Eds), Springer, (1999); *Asymmetric Catalysis in organic Synthesis*, Noyori, R., John Wiley, (1994)). These beta hydroxy acid or ester products can be further reduced to give required 1-(aryl)-propane-1,3-diols in high ee. (path A). The β-keto acid or ester substrates for high pressure hydrogenation or hydrogen transfer reactions may be prepared by a variety of methods such as condensation of acetophenone with dimethylcarbonate in the presence of a base (Chu; et al., *J. Het Chem.* 22:1033 (1985)), by ester condensation (Turner, et al., *J. Org. Chem.* 54:4229 (1989)) or from aryl halides (Kobayashi, et al., *Tetrahedron Lett.* 27:4745 (1986)). Alternatively, 1,3-diols of high enantiomeric purity can be obtained by enantioselective borane reduction of β-hydroxyethyl aryl ketone derivatives or β-keto acid derivatives (path B) (Ramachandran, et al., *Tetrahedron Lett.* 38:761 (1997)). In another method, commercially available cinnamyl alcohols may be converted to epoxy alcohols under catalytic asymmetric epoxidation conditions. These epoxy alcohols are reduced by Red-Al to result in 1,3-diols with high ee's (path C) (Gao, et al., *J. Org. Chem.* 53:4081 (1980)). Enantioselective aldol condensation is another well described method for synthesis of 1,3-oxygenated functionality with high ee's starting from aromatic aldehydes. (path D) (Mukaiyama, *Org. React.* 28:203 (1982)).

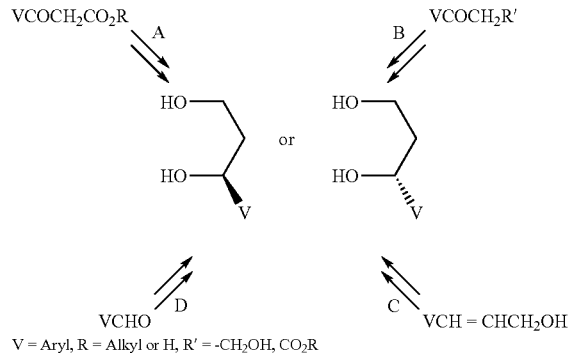

V = Aryl, R = Alkyl or H, R' = -CH₂OH, CO₂R

For the purpose of this invention the intermediate ketoester is prepared from 4-acetylpyridine of Formula A. The C' identifies the carbon that is, the methine carbon stereogenic center in the final compound prepared by this invention.

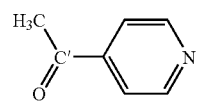

Formula A

The compound of Formula A is reacted with dimethylcarbonate to obtain the oxo-propanoic acid methyl ester. The stereogenic center is installed using the hydrogen transfer method of Noyori (Fujii et al., *J. Am. Chem. Soc.* 118(10): 2521-2 (1996)). The oxy-propanoic acid ester is reduced in the presence of a enantioenriched ruthenium catalyst (10) to the hydroxy ester intermediate which is further reduced with sodium borohydride to the enantioenriched 1,3-propane diol, shown in the following Formula B:

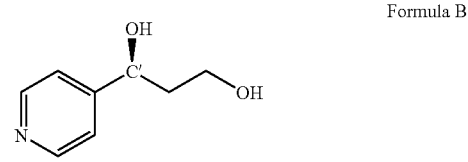

Formula B

The stereogenic center at the carbon, C' has been established in this process step and the enantiomeric excess was maintained throughout the remainder of the process.

1.3. Synthesis of Phosphorylating Reagents

Another aspect of the invention is the preparation of phosphorylating agents of Formula C:

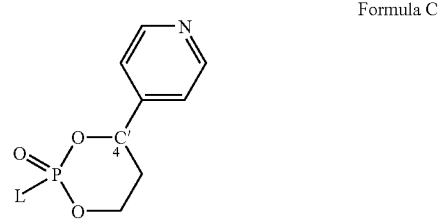

Formula C

Wherein:

L is a leaving group selected from the groups consisting of halogens, aryloxy groups substituted by 1 to 3 electron-withdrawing groups.

The groups L and 4-pyridyl are trans to one another.

Compounds of Formula C are either racemic, have the S configuration at carbon C', or have the R configuration at carbon C'.

The general synthesis of the phosphorylating reagent of Formula C is accomplished by reacting 1-(4-pyridyl)-1,3-propane diol with phosphorodichloridate of formula Cl₂P(O)-L. In one aspect, leaving groups L are selected from halogen, and aryloxy groups substituted by 1 to 3 electron-withdrawing groups. In another aspect, leaving groups are halogens such as chloro or bromo, and substituted-aryloxy groups such as chlorophenoxy, dichlorophenoxy or nitrophenoxy. In another aspect, leaving groups are chloro, 4-chlorophenoxy, 3,5-dichlorophenoxy, 2,4-dichlorophenoxy and 4-nitrophenoxy. Phosphorodichloridate where L is aryloxy are synthesized by reacting substituted-phenols with phosphorusoxychloride (Rathore et al., *Indian J. Chem B* 32(10), 1066 (1993)).

The enantioenriched activated phosphorylating agent is synthesized by phosphorylation of an enantioenriched 1-(4-pyridyl)-1,3-propane diol with phosphorodichloridates of formula L-P(O)Cl$_2$ in the presence of a base (Ferroni et al., *J. Org. Chem.* 64(13), 4943 (1999)). In one aspect, orders of addition include the addition of a solution of the diol and the base to a solution of the phosphorodichloridate in the chosen solvent. In another aspect, a solution of the diol and the base, and another solution containing the phosphorodichloridate in the same solvent or a different solvent, are added simultaneously to a chosen solvent. In another aspect, a solution of the diol is added to a solution of the phosphorus reagent followed by the addition of the base. Typical solvents for the phosphorylation of the diol are polar aprotic solvents that have low reactivity with phosphorodichloridates and solubilize the diol or the phosphorodichloridate. In one aspect, solvents to run the phosphorylation reaction are dichloromethane, THF, acetonitrile, pyridine, tetraalkylureas, trialkyl phosphates or hexaalkylphosphoramides. In another aspect, the solvents are dichloromethane, THF, acetonitrile, pyridine, DMPU, DMEU, tetramethyl urea, trimethyl phosphate, or hexamethylphosphoramide. The reaction temperature is kept low, especially during the initial phase of the reaction, which is exothermic, so as to preserve the integrity of the reagents. In one aspect, temperatures are kept below room temperature within −20° C. to 10° C. In one aspect, the exotherm is under control, the reaction temperature is brought slowly to room temperature to complete the formation of the phosphate reagent. In another aspect, the temperature is kept the same until completion of the reaction to preserve the integrity of the reagent. Due to the stereogenic nature of the phosphorus atom, reaction of the phosphorodichloridate with the diol under the reaction conditions described above gives a mixture of cis and trans isomers, slightly favoring the cis-isomer. Typical cis/trans ratios range from 50/50 to 60/40. The cis and trans isomers are separated by a combination of column chromatography and/or crystallization. In one aspect of this invention, we found that when the isolated cis-isomer of the 4-nitrophenoxy phosphorylating reagent was heated with a salt of 4-nitrophenol, >85% of the phosphorylating reagent isolated was the trans-isomer. In another aspect of this invention we found that when the isolated mixture of cis and trans isomers of the 4-nitrophenoxy phosphorylating reagent was heated with a salt of 4-nitrophenol, in the same solvent used for the phosphorylation step or another solvent, >85% of the phosphorylating agent isolated was the trans-isomer. Furthermore, it was found that no prior isolation of the mixture was necessary to achieve the enrichment. As such, addition of the salt of the phenol-leaving group to the crude reaction mixture in which the aryloxy phosphorylating reagent of the diol was generated accomplished the enrichment in the trans-isomer of Formula C, in the same ratio obtained when performing the enrichment on the isolated mixture of phosphorylating reagents. Similarly, when an equimolar mixture of cis and trans phosphorochloridate of compound of formula C (L=Cl) was heated, only the trans isomer could be isolated. The phenoxide salt is generated by reacting the corresponding phenol with a base, preferably trialkylamines, nitrogen-containing heterocycles or sodium. In one aspect, bases are triethylamine, diisopropylethylamine, pyridine, DABCO, DBU, sodium hydride or an alkali metal. In another aspect, bases are triethylamine, DBU or the sodium salt of the phenoxide. The enrichment step can be run at room temperature but is generally heated to decrease reaction times, preferably in the range of 40° C. to 70° C. While the conversion of the aryloxy phosphorylating reagent requires the addition of the salt of the corresponding phenoxide, the conversion of phosphorochloridates of the chiral diol do not necessitate the additional use of soluble chloride salts as the formation of the phosphorochloridate itself with the preferred bases generates two equivalents of chloride ion. In one aspect, upon completion of the phosphorylation of the diol, the reaction mixture is then heated, preferably in the range of 40° C. to 70° C., to completely convert the cis isomer into the trans isomer. In another aspect the temperature is kept the same as the one used for the addition of the reagents.

For the preparation of enantioenriched phosphorylating agent from enantioenriched diols, preservation of the chirality at carbon C' is critical. Partial racemization was observed with 1-(4-pyridyl)-1,3-propane diol where the initial ee of 98% for the diol was reduced to <85% in the isolated trans-phosphorylating reagent using the described conditions. In one aspect of this invention, it was discovered that the use of N-containing heteroaryl solvents maintained the optical purity of the trans-phosphorylating agent above 95% ee. In one aspect, N-containing heteroaryl solvents are optionally substituted pyridines, quinolines, and pyrazines. In another aspect, N-containing heteroaryl solvents are optionally substituted pyridines. In another aspect, the N-containing heteroaryl solvent is pyridine. In an other aspect of the invention, it was discovered that formation of the salt of the enantioenriched 1-(4-pyridyl)-1,3-propane diol prior to addition of the phosphorodichloridate or phosphorusoxychloride and subsequent addition of the base helped prevent epimerization of the C' carbon without requiring the use of a N-containing heteroaryl solvents. In one aspect, salts of 1-(4-pyridyl)-1,3-propane diol are salts made by reacting 1-(4-pyridyl)-1,3-propane diol with an organic or mineral acid with a pka <2. In another aspect, salts are mineral acids with pka<1. In another aspect, salts are the hydrochloride and hydrobromide salts. The cis and trans isomers are separated by a combination of column chromatography and/or crystallization. However, it was found that after running the enrichment step, the isolation of the trans-isomer was greatly simplified yielding phosphorylating reagents of great purity, >95% trans-isomer and ee >95%. In one aspect the trans-phosphorylating reagent is isolated. In another aspect, the phosphorylating reagent is kept in solution and used for the phosphorylation of nucleosides without purification. The relative configuration of the phosphorus atom is determined by comparison of the $^{31}$P NMR spectra. The chemical shift of the equatorial phosphoryloxy moiety (trans-isomer) is more upfield than the one of the axial isomer (cis-isomer) (Verkade, et al., *J. Org. Chem.* 42, 1549 (1977)).

2.0 Synthesis of Cis-Prodrugs of araCMP

For the synthesis of cis-prodrugs of Formula I, the prodrug moiety can be introduced at different stages of the synthesis. Most often the cyclic phosphates are introduced at a later stage, because of the general sensitivity of these groups to various reaction conditions. The synthesis can also proceed through using protected or unprotected cytarabine. Single stereoisomers of the cis-prodrugs can either be made by separation of the diastereoisomers by a combination of column chromatography and/or crystallization, or by enantiospecific synthesis using enantioenriched phosphorylating agents.

2.1. Protection of Cytarabine

Various preparations of araC (Merck Index 11th Edition, No. 2790) and its analogues are described in the literature (e.g. U.S. Pat. No. 3,116,282; Shen et al., *J. Org. Chem.* 30: 835-838 (1965); Hessler, *J. Org. Chem.* 41(10):1828-1831 (1976)) and are known to those skilled in the art.

Cytarabine is also available from commercial sources including, but not limited to, Shanghai Freeman International Trading Co., Brantford, Sigma, Fluka, and Sunray Pharmaceuticals.

The general procedure for the phosphorylation of protected cytarabine is accomplished by reacting a suitably protected cytarabine intermediate with a base and reacting the alkoxide generated with the phosphorylating reagent. The protected cytarabine can be prepared by one skilled in the art using one of the many procedures described for the protection of nucleosides (Greene T. W., Protective Groups in Organic Chemistry, John Wiley & Sons, New York (1999)). The nucleoside is protected in such a way as to expose the 5'-hydroxyl group on which to add the phosphate group while protecting all the remaining hydroxyls and other functional groups on the nucleoside that may interfere with the phosphorylation step or lead to regioisomers. In one aspect, the protecting groups selected are resistant to strong bases, e.g., ethers and silyl ethers. In another aspect, the protecting groups are optionally substituted MOM ethers, MEM ethers and trialkylsilyl ethers. In another aspect, the protecting group is t-butyldimethylsilyl ether. Further protection entails masking of the 4-nitrogen of cytarabine so as to eliminate any acidic protons. In one aspect the selected N-protecting groups are selected from the groups of dialkyl formamidines, mono and dialkyl imines, mono and diaryl imines. In one aspect, the N-protecting groups are selected from the groups of dialkyl formamidines and mono-alkyl imine and mono aryl imine. In one aspect the mono-alkyl imine is benzylimine and the mono-aryl imine is phenylimine. In another aspect, the N-protecting group is a symmetrical dialkyl formamidine selected from the group of dimethyl formamidine and diethyl formamidine.

In one aspect, the protection of cytarabine is accomplished by the following 4-step procedure. Cytarabine is treated with benzoyl chloride in DMPU to obtain the benzoate ester. The ester is heated with tert-butyldimethylsilyl chloride to give a mixture of the disilyl and monosilyl compounds. The crude mixture is treated with ethanolic hydrazine to cleave the ester. Aqueous work-up and purification as the hydrochloride salt gave the desired 2',3'-disilylcytarabine as a single entity. This is mixed with dimethylformamide dimethylacetal to yield the protected cytarabine formamidine compound as shown in Formula D:

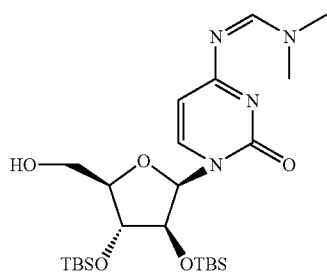

Formula D 2.2. Phosphorylation of Protected Cytarabine

Generation of the alkoxide of the exposed hydroxyl group on the suitably protected cytarabine is accomplished with a base in an aprotic solvent that is not base sensitive such as THF, dialkyl and cylic formamides, ether, toluene and mixtures of those solvents. In one aspect, the solvents are DMF, DMA, DEF, N-methylpyrrolidine, THF, and mixtures of those solvents.

Many different bases have been used for the phosphorylation of nucleosides and nonnucleoside compounds with cyclic and acyclic phosphorylating agents. For example trialkylamines such as triethylamine (Roodsari et al, *J. Org. Chem.* 64(21), 7727 (1999)) or diisopropylethylamine (Meek et al, *J. Am. Chem. Soc.* 110(7), 2317 (1988)); nitrogen containing heterocyclic amines such as pyridine (Hoefler et al., *Tetrahedron* 56(11), 1485 (2000)), N-methylimidazole (Vankayalapati et al, *J. Chem. Soc. Perk T* 1 14, 2187 (2000)), 1,2,4-triazole (Takaku et al, *Chem. Lett.* (5) 699 (1986)) or imidazole (Dyatkina et al., *Tetrahedron Lett.* 35(13), 1961 (1994)); organometallic bases such as potassium t-butoxide (Postel et al., *J Carbohyd. Chem.* 19(2), 171 (2000)), butyllithium (Torneiro et al., *J. Org. Chem.* 62(18), 6344 (1997)), t-butylmagnesium chloride (Hayakawa et al., *Tetrahedron Lett.* 28(20), 2259 (1987)) or LDA (Aleksiuk et al., *J. Chem. Soc. Chem. Comm.* (1)11 (1993)); inorganic bases such as cesium fluoride (Takaku et al., *Nippon Kagaku Kaishi* (10), 1968 (1985)), sodium hydride (Hanaoka et al., *Heterocycles* 23(11), 2927) (1985)), sodium iodide (Stromberg et al., *J. Nucleos. Nucleot.* 6(5), 815 (1987)), iodine (Stromberg et al., *J. Nucleos. Nucleot.* 6(5), 815 (1987)) or sodium hydroxide (Attanasi et al., *Phosphorus Sulfur* 35(1-2), 63 (1988)); metal such as copper (Bhatia et al., *Tetrahedron Lett.* 28(3), 271 (1987)). However, no reaction or racemization at the phosphorus chiral center was observed when coupling of phosphorylating reagent of Formula C was attempted using the previously described procedures. Especially, no reaction was observed with bases previously used with substituted cyclic phosphorylating reagent to give the corresponding cyclic phosphates in high yield such as sodium hydride (Thuong et al., *Bull. Soc. Chim. Fr.* 667 (1974)), pyridine (Ayral-Kaloustian et al., *Carbohydr. Res.* 187 (1991)), butyl-lithium (Hulst et al., *Tetrahedron Lett.* 1339 (1993)), DBU (Merckling et al., *Tetrahedron Lett.* 2217 (1996)), triethylamine (Hadvary et al., *Helv. Chim. Acta* 69(8), 1862 (1986)), N-methylimidazole (Li et al., *Tetrahedron Lett.* 6615 (2001)) or sodium methoxide (Gorenstein et al.; *J. Am. Chem. Soc.* 5077 (1980)). In one aspect of this invention, it was found that the use of Grignard reagents promoted phosphorylation with minimal epimerization of the phosphorus center. In one aspect, Grignard reagents are alkyl and aryl Grignards. In another aspect, Grignard reagents are t-butyl magnesium halides and phenyl magnesium halides. In another aspect, Grignard reagents are t-butylmagnesium chloride and phenylmagnesium chloride.

In another aspect of the invention, magnesium alkoxides are used to generate the magnesium 5'-alkoxide of cytarabine. In one aspect, magnesium alkoxides are selected from the group of $Mg(O-t-Bu)_2$ and $Mg(O-iPr)_2$.

In another aspect of this invention, Lewis acids can be added to the solution of the 5'-alkoxide, made with one of the bases previously described, to either exchange the carbocation of the alkoxide and/or modulate the reactivity of the formed alkoxide with the phosphorylating agent. Examples of Lewis acids include alkali salts, rare earth salts or transition metal salts. In one aspect, Lewis acids are magnesium salts, calcium salts, cesium salts, aluminum salts or cerium salts. In another aspect, Lewis acids are magnesium chloride, magnesium bromide and magnesium iodide.

In one aspect, reaction conditions for the synthesis of compounds of Formula I encompass first the generation of the alkoxide with a Grignard reagent or, one of the other bases followed by addition of magnesium salts, second the addition of the phosphorylating reagent of Formula C to the solution of the nucleoside, either in solution, generally in the same solvent but not necessarily, or directly as a solid. In another aspect, the solution of the alkoxide is added to the solution of the phosphorylating reagent. In one aspect, temperatures for the generation of the alkoxide with a base are chosen from the range of −78° C. to 40° C. In one aspect, temperatures are chosen from the range of −20° C. to 25° C. In another aspect, temperatures for the phosphorylation step are chosen from the range of −10° C. to 70° C. In another aspect temperatures are chosen from the range of 10° C. to 40° C.

The protected prodrugs generated as described above are then subjected to a deprotection step to remove all the protecting groups using one of the many methods known to those skilled in the art (Greene T. W., Protective Groups in Organic Chemistry, John Wiley & Sons, New York (1999)) and that are compatible with the stability of the phosphate prodrug. In one aspect, deprotection reagents include fluoride salts to remove silyl protecting groups, mineral or organic acids to remove acid labile protecting groups, such as silyl and/or ketals and N-protecting groups, if present. In another aspect, deprotection reagents are TBAF, hydrochloric acid solutions and aqueous TFA solutions. In another aspect, the deprotection reagents are hydrochloric acid solutions. Isolation and, purification of the final prodrugs, as well as all intermediates, is accomplished by a combination of column chromatography and/or crystallization to give compounds of Formula I.

In another aspect, the present invention provides methods to synthesize single isomers of compounds of Formula I. Due to the presence of a stereogenic center at C' on the cyclic phosphate reagent, this carbon atom can have two distinct orientations, namely R or S. As such the trans-phosphate reagent of Formula C can exist as either the S-trans or R-trans configuration and these two reagents are enantiomers. Therefore synthesis of the phosphorylating agent from a racemic diol generates racemic mixture of the R-trans and S-trans isomers. In addition, because cytarabine is chiral, phosphorylation of this nucleoside with a racemic trans-phosphate reagent will generate a mixture of two diastereomeric cis-prodrugs of Formula I. These compounds can be separated by a combination of column chromatography and/or crystallization. Alternatively, phosphorylation of the alkoxide of cytarabine with an enantioenriched trans-phosphate reagent generates a single cis-prodrug. As such reaction of the C'-S-trans-phosphate reagent, made from diol of Formula B, generates the C'-S-cis-prodrug of Formula III while reaction with the C'-R-trans-phosphate reagent generates the C'-R-cis-prodrug.

In another aspect, depending on the rate of epimerization of the cis-phosphate reagent to the trans-phosphate reagent compared to the rate of reaction of cytarabine with the trans-phosphate reagent, it was discovered that a cis-phosphorylating reagent still gives the cis-prodrug of cytarabine. In that aspect, the cis-phosphorylating reagent epimerizes to the trans-phosphate reagent with the traces of the leaving group generated by the formation of small amounts of the prodrug. Cytarabine then reacts with the trans-phosphate reagent being generated in-situ giving the cis-prodrug. In another aspect, cytarabine is reacted with a crude mixture of phosphorylating reagent to generate the cis-prodrug. In one aspect, the crude mixture of the phosphorylating reagent has been enriched in the trans-isomer. In another aspect the phosphorylating reagent is used without the enrichment step.

2.3. Phosphorylation of Unprotected Cytarabine

Alternatively, the prodrug of cytarabine can be synthesized without prior protection using reaction conditions that selectively phosphorylate primary hydroxyl groups. Selective 5'-acylation of nucleosides such as araC with acyl chlorides is well established (Gish et al., J. Med. Chem. 14, 1159 (1971)). However, because phosphorylating agents are considered to be more reactive, they presumably would give rise to less regioselectivity and lower yields, as well as reaction with the solvent used in the reaction (DMF). In one aspect of the invention, we found that reaction of a phosphorylating agent of Formula C with unprotected cytarabine generated the 5'-cis-phosphate prodrug of Formula I in high yield, regioselectivity and stereoselectivity. In one aspect the isolated phosphorylating is added to a solution of cytarabine. In another aspect cytarabine is added to a solution of the phosphorylating reagent. Similarly reaction of the S-trans-phosphorylating reagent, made from S-diol of Formula B, generates the R-cis-prodrug of Formula III, while the R-trans-phosphorylating reagent generates the R-cis-prodrug. Due to the poor solubility of unprotected nucleosides in common solvents and the potential reactivity of the solvent with the phosphorylating reagent, solvents with strong dielectric constant that have low reactivity with the phosphorylating reagent are necessary. Examples of such solvents are tetraalkylureas. In one aspect, solvents are DMPU, tetramethyl urea, DMEU, trimethyl phosphate or hexamethylphosphoramide.

EXAMPLES

Example 1

Synthesis of methyl-3-oxo-3-(pyrid-4-yl)-propanote
(1)

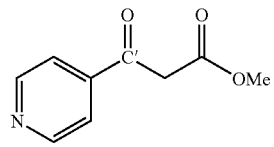

1

A 50 L, 3-neck round bottom flask was equipped with an overhead stirrer, heating mantle, and nitrogen inlet. The flask was charged with THF (8 L) and potassium t-butoxide (5 kg, 44.6 mol), followed by additional THF (18 L). 4-Acetylpyridine (2.5 kg, 20.6 mol) was added accompanied by an increase in temperature, followed by the addition of dimethylcarbonate (3.75 L, 44.5 mol). After both additions, the mixture temperature was greater than 40° C. The reaction mixture was stirred without heating for 2.5 h, during which period the temperature increased to an average temperature around 55° C. Then the mixture was heated to 57-60° C. for 3 h. The process was monitored by thin layer chromatography (TLC). The heat was turned off and the mixture allowed to cool slowly overnight (15 h). The mixture was then filtered through a 45 cm Buchner funnel. The solid, the potassium enolate of the keto ester, was returned to the 50 L flask and diluted with aqueous acetic acid (3 L acetic acid in 15 L of water). This acidic mixture was extracted with t-butyl methyl ether (MTBE) (1×16 L, 1×12 L). The organic layers were combined and washed with aqueous sodium carbonate ($Na_2CO_3$) (1750 g in 12.5 L water), saturated aqueous sodium bicarbonate ($NaHCO_3$) (8 L), and brine (8 L). Magnesium sulfate ($MgSO_4$) (500 g) was used to dry the combined organic layers overnight (15 h). The dried organic solution was filtered and the solvent removed by rotary evaporation to a mass of 6.4 kg. Material began to precipitate after the removal of approximately half the solvent. The resulting suspension was cooled in an ice bath with stirring for 2 h. The solid was collected by filtration, washed with MTBE (500 mL), and dried in a vacuum oven at 20° C. for 15 h, giving 2425 g (60% yield) of the keto ester 1 as a pale yellow solid.

The MTBE mother liquor was concentrated to approximately 1 L. The resulting suspension was cooled in an ice bath for 1 h. The solid was collected by filtration, washed with MTBE (2×150 mL), and dried in a vacuum oven to give 240 g (6%) of a second crop.

TLC Condition: The reaction mixture was monitored using Merck silica gel 60 plates, 2.5×7.5 cm, 250 micron; UV lamp: 1:2 THF/hexane solvent. Rf of Starting Material=0.25; Rf of product=0.3

Example 2

Synthesis of (S)(−)Methyl-3-hydroxy-3-(pyridin-4-yl)-propanote (2)

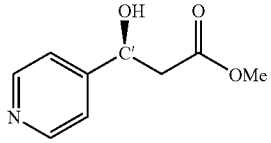

2

A 22 L, 3-neck round bottom flask was equipped with an overhead stirrer, thermowell/thermometer, addition funnel (1 L), and cooling vessel (empty). The flask was flushed with nitrogen, charged with formic acid (877 g) and cooled with an ice bath. Triethylamine (TEA) (755 g) was charged to the addition funnel and added slowly over a time span of 50 minutes to the stirred formic acid. There was an exothermic reaction with moderate fuming which dissipated towards the end of the addition. After the addition was complete, the cooling bath was removed and the reaction solution was diluted with dimethylformamide (DMF) (5.0 L). The ketoester 1 (2648 g) was added in one portion, followed by an additional 0.5 L of DMF in an endothermic reaction. There was a decrease in temperature to about 5° C. at which point the ketoester 1 was insoluble. The flask was equipped with a heating mantle and the stirred mixture was heated gradually to 16° C. to dissolve all solids. The chiral ruthenium catalyst (18.8 g) (10) was added in one portion and the stirred mixture was heated to 55° C. over 1 h. The resulting dark solution was stirred at 55° C. for 16 h. TLC was used to determine when the reaction was complete. The solvent was evaporated under reduced pressure (Buchi R152 rotary evaporator under high vacuum, bath temp=60° C.) to give 3574 g of a brown oil. The oil was dissolved in dichloromethane (10 L) and transferred to a 5 gal. stationary separatory funnel. The dark solution was washed with saturated sodium bicarbonate solution (3.0 L) and the aqueous phase was then back extracted with dichloromethane (3.0 L). The combined dichloromethane extracts were dried over MgSO$_4$ (300 g), filtered, and concentrated under reduced pressure to provide 3362 g of a brown oil (125% of theoretical, contains DMF by $^1$HNMR). The $^1$H-NMR analysis for this example and the following examples were performed on a VARIAN GEMINI-200 MHz Spectrometer. The samples were dissolved in the indicated solvent and the chemical shifts are referenced to the residual solvent.

TLC Condition: The reaction mixture was monitored using Merck silica gel 60 plates, 2.5×7.5 cm, 250 micron; UV lamp: 5% MeOH in CH$_2$Cl$_2$: Rf of Starting Material=0.44; Rf of product=0.15

$^1$H NMR (CDCl$_3$): δ 2.73 (d, 2H, J=1.5 Hz), 3.73 (s, 3H), 4.35 (s, 1H), 5.11-5.19 (m, 1H), 7.31 (d, 2H, J=6.6 Hz), 8.53 (d, 2H, J=6.0 Hz)

e.e.=87% S isomer (determined by HPLC).

HPLC conditions:

Column: Chiralpak AD, 0.46×25 cm; mobile phase=10:90, ethanol:hexane, isocratic; flow rate=1.5 mL/min; injection volume=10 μL UV detection at 254 nm; r.t.: R-hydroxy ester=19.9 min; S-hydroxy ester =21.7 min.

Example 3

Synthesis of S-(−)-1-(4-Pyridyl)-1,3-propanediol (3)

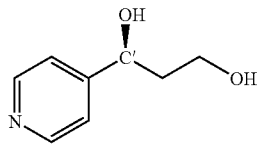

3

A 22 L, 4-neck round bottom flask was equipped with an overhead stirrer, thermowell/thermometer, addition funnel (2 L), condenser and cooling vessel (empty). The flask was flushed with nitrogen and charged sequentially with sodium borohydride (419 g) and 1-butanol (9.0 L). The crude hydroxyester (2) was dissolved in 1-butanol (1.0 L, total volume of solution=3.2 L). A quarter portion (800 mL) of the hydroxyester solution was added slowly to the stirred sodium borohydride slurry over 90 minutes. The temperature increased from 19° C. to 32° C. and moderate off-gassing occurred. The mixture was stirred for 45 minutes and the temperature peaked at 36° C. A second quarter portion of the hydroxyester solution was added slowly over 45 minutes with a temperature increase from 36 to 52° C. The mixture was stirred for 20 minutes and the temperature peaked at 57° C. The mixture was cooled to 40° C. using an ice bath and the third quarter portion of the hydroxyester solution was added over 45 minutes. Again the temperature exhibited an increase from 38 to 51° C. The mixture was stirred for 20 minutes with the temperature peaking at 57° C. The mixture was cooled to 38° C. and the final quarter portion of the hydroxyester solution was added over 25 minutes and there was no apparent exothermic reaction at this point. The mixture was stirred for 40 minutes with the temperature at 45° C., then the flask was equipped with a heating mantle and the stirred mixture was heated to 80° C. over a 2.5 h period. The mixture was stirred at 80-85° C. for 3 h. The mixture was gradually cooled to ambient temperature over a 12 h period. TLC was again used to monitor the completeness of the reaction. The reaction mixture was quenched with aqueous potassium carbonate solution (20 wt %, 5.2 L) and the mixture was stirred for 10 minutes. The layers were separated and the butanol phase layer was washed with aqueous potassium carbonate solution (20 wt %, 2.6 L) and sodium chloride solution (15 wt %, 1.3 L). The solvent was removed under reduced pressure (Buchi R152 rotary evaporator, high vacuum, bath temperature=60° C.) to provide a yellow semi-solid. Acetonitrile (3 L) was fed into the evaporator flask and the solvent was evaporated under reduced pressure. Acetonitrile (9 L) was again fed into the evaporator flask and the slurry was stirred (rotation on the rotary evaporator) at 60° C. (bath temperature=65° C., atmospheric pressure) for 15 minutes. The hot slurry was filtered through a filtering agent of $SiO_2$ (Celite 521) (250 g as a slurry in 1 L of acetonitrile was prepacked on a 24 cm Buchner funnel). The filtrate was partially concentrated under reduced pressure (4 L of distillate were collected) and the resulting slurry was heated at atmospheric pressure on the rotary evaporator to dissolve all solids (bath temp=65° C.). The heat source was turned off and the resulting solution was stirred on the rotary evaporator for 16 h, with gradual cooling to ambient temperature. The resulting mixture was filtered and the collected solid was washed with acetonitrile (2×200 mL) and dried to constant weight (−30 in Hg, 55° C., 4 h), giving (3, 436 g, 39%) as a pale yellow solid.

Melting point=98-100° C.

e.e.=98% S isomer (determined by HPLC).

HPLC conditions: Column: Chiralpak AD, 0.46×25 cm; mobile phase=10:90, ethanol:hexane, isocratic; flow rate=1.5 mL/min; injection volume=10 μL UV detection at 254 nm; r.t.: R-diol=12.7 min; S-diol=14 min.

Example 4

Synthesis of (4S)-(−)-Trans-4-(4-pyridyl)-2-(4-nitrophenoxy)-2-oxo-1,3,2-dioxaphosphorinane (4)

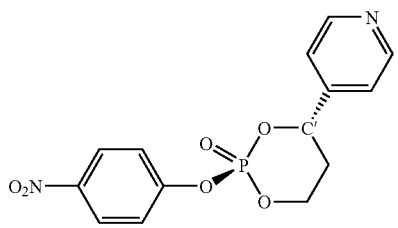

4

A 1 L round bottom flask equipped with a magnetic stirrer and nitrogen inlet was charged with diol 3 (100 g, 0.65 mol) and pyridine (500 mL). The mixture was vigorously stirred at room temperature until diol 3 had completely dissolved. The solubility of 3 is lessened by TEA. A separate 3 L, 3-neck round bottom flask was equipped with an overhead stirrer, thermocouple, 1 L addition funnel and nitrogen inlet. This vessel was charged with 4-nitrophenyl phosphorodichloridate (166.4 g, 0.65 mol), placed in an ice bath and then pyridine (500 mL) was introduced through the addition funnel. The resulting mixture was stirred at ice bath temperature for 15 minutes.

After 3 was completely dissolved (approximately 0.5 h), TEA (190 mL, 1.36 mol) was added and the slightly cloudy; yellow-brown solution was transferred to the addition funnel on the 3 L flask and added to the cold dichloridate solution over 2 hours 40 minutes. The reaction was exothermic and the addition rate was maintained such that the reaction temperature did not exceed 6° C. After the addition was complete, the ice bath was replaced with a room temperature water bath and stirring was continued for 3 h.

During this time, a separate 3 L, 3-neck round bottom flask was equipped with an overhead stirrer, thermocouple, 250 mL addition funnel and nitrogen inlet. This flask was then charged with sodium hydride (15 g, 0.38 mol) and THF (100 mL) and the addition funnel was charged with a solution of 4-nitrophenol (67.5 g, 0.49 mol) in THF (100 mL). The flask was then placed in an ice bath and the nitrophenol solution was slowly added to the cold suspension of sodium hydride. A temperature of <40° C. was maintained during the addition of the nitrophenol. The cessation of gas evolution indicated that the addition was complete. The resulting bright orange suspension was stirred at room temperature for 1 h.

After the diol (3)—dichloridate reaction was judged complete by HPLC, the dark suspension was subjected to vacuum filtration. The glassware and filter cake (TEA-HCl) were rinsed with THF (100 mL), and the combined filtrate and rinse were poured into the orange, sodium 4-nitrophenoxide suspension. The resulting mixture was then heated at 40° C. for 4 h and the cis/trans equilibration was monitored by HPLC. The heating mantle was turned off and the reaction was stirred at room temperature. The crude reaction mixture was filtered through filtering agent, $SiO_2$ (Celite 521, 0.5 inch) and the glassware and Celite were rinsed with 200 mL of dichloromethane. The combined filtrate and rinse were concentrated on a rotary evaporator at 30-35° C. at reduced pressure (oil pump). The resulting thick, black, foamy tar was dissolved in 1.0 M aq HCl (1.5 L) and ethyl acetate (800 mL), transferred to a 4 L separatory funnel and the phases were separated. The ethyl acetate layer was washed with an additional 300 mL portion of 1.0 M aq HCl. Dichloromethane (750 mL) was added to the combined aqueous layers and while vigorously stirring the mixture, it was carefully neutralized with solid sodium bicarbonate to pH between 7 and 8. The solution was again transferred to a 4 L separatory funnel and the layers were separated. The aqueous layer was extracted with dichloromethane (750 mL) and the combined organic layers were dried over magnesium sulfate, filtered, and concentrated to dryness. The resulting dry residue was stirred as a slurry in isopropanol (200 mL) and filtered to give 190 g of phosphate 4.

The crude 4 was dissolved in dichloromethane (600 mL), stirred for 10 minutes in the presence of 10 g of activated carbon (Darco), and filtered through $SiO_2$ (Celite 521, 0.5 inch). The flask and Celite were rinsed with dichloromethane (150 mL) and the combined filtrate and rinse were again concentrated to dryness. The resulting solid was powdered and stirred at 50° C. as a slurry in isopropanol (250 mL); After 1 h the slurry was cooled to room temperature and subsequently to ice bath temperature for filtering. The solid was dried for 16 hours at 55° C. in a vacuum oven to yield 154.6 g (70%) of phosphate 4 as a beige solid.

m.p.=140-142° C.

Specific Rotation=−80.350° (c=1.0, MeOH)

HPLC conditions: Column: Chiralpak AD, 0.46×25 cm; mobile phase=50:50, 2-propanol:hexane, isocratic; flow rate=1.0 mL/min; injection volume=10 μL UV detection at 254 nm.; r.t.=6.6 min., 99+% trans ee=99+%

$^1$H NMR (DMSO-$d_6$): δ 2.23-2.29 (m, 2H), 4.56-4.71 (m, 2H), 5.88-5.95 (m, 1H), 7.44 (d, 2Hh, J=5.8 Hz), 7.59 (d, 2H, J=9.2 Hz), 8.34 (d, 2H, J=9.4 Hz), 8.63 (d, 2H J=5.8 Hz)

Example 5

Synthesis of 5'-O-benzoylcytarabine (5)

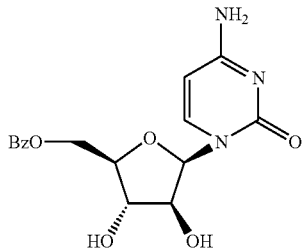

5

A 12 L, 4-neck round bottom flask was equipped with an overhead stirrer, thermocouple, and nitrogen inlet. The vessel was charged with cytarabine (500 g, 2.06 mol) and DMPU (1 L), which gave a thick but stirrable solution. A solution of HCl in dioxane (617 mL, 2.47 mol) was added in one portion with a temperature increase to 52° C. The mixture was stirred for 2 hours and cooled to 27° C. Benzoyl chloride (578 g, 4.11 mol) was added and the mixture was stirred at ambient temperature for 22 h with a temperature increase to 34° C. during first 30 minutes. After 2.5 h, the temperature had decreased to 25° C. Water (2.5 L) was added and the mixture was stirred for 30 minutes with the temperature increasing to 37° C. The resulting layers were separated and the aqueous layer was extracted with dichloromethane (2×1 L); The combined organic layers were extracted with 10% (vol/vol) aqueous HCl (2×500 mL). The combined aqueous layers were charged to the 12 L flask, diluted with water (1.5 L) and cooled in an ice bath. The pH was adjusted to 10 by adding 30% (wt/wt) aqueous NaOH (850 mL). There was a temperature increase during neutralization from 14° C. to 21° C. during the 30 minute addition period. Precipitate formation began to occur at pH 3. While remaining in the ice bath, the resulting thick suspension was stirred for 8 h. The solid was collected in a 24 cm Buchner. The cake was washed with water (2 L) and partially dried in the funnel overnight. The resulting solid material was dried in a vacuum oven at 70° C. for 18 h, giving 659 g (92% yield) of 5'-O-benzoylcytarabine (5). The water content as measured by Karl Fischer was too high and the material was recrystallized. A 12 L flask was charged with (5), methanol (5 L), and ethanol (3 L), and this mixture thickened after stirring. The mixture was heated to reflux, giving a clear, yellow solution. The mixture was distilled at atmospheric pressure until 2 L of distillate were collected. Ethanol (2 L) was added and distillation continued until 1 L more was collected. At the end of the distillation the temperature was 79° C. The heat was turned off and the mixture was cooled to 21° C. and stirred for 19 h. The solid was collected by filtration, washed with ethanol (1 L), and dried in a vacuum oven at 70° C. for 36 h to give 508 g (71%) of compound 5 as a white crystalline solid.

HPLC conditions: Column: Zorbax Eclipse XDB-C8; Solvent A=5% acetonitrile in 20 mM sodium phosphate buffer; solvent B=80% acetonitrile in water; gradient; flow rate=1.0 mL/min, injection volume=10 μL UV detection at 270 nm; r.t.=4.3 min.

Example 6

Synthesis of 5'-O-benzoyl-2',3'-di-O-TBS-cytarabine (6)

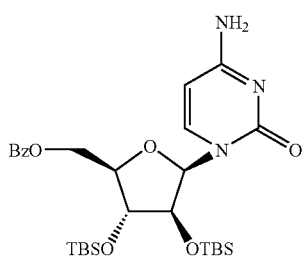

6

A 12 L, 4-neck round bottom flask was equipped with an overhead stirrer, thermocouple, condenser, and nitrogen inlet. The flask was charged with pyridine (703 mL, 8.64 mol), DMF (1 L), and (5). The mixture was stirred for 5 minutes. Addition of compound (5) to solvent facilitates dissolution. tert-Butyldimethylsilyl chloride (TBSCl) was added, followed by DMF (500 mL). The mixture was heated at 93° C.±1° C. for 44 h with occasional monitoring by HPLC. The mixture was cooled to 51° C. and methanol (250 mL) was added to quench unreacted TBSCl. The mixture was stirred for 4.5 h after which time water (2 L) was added. After stirring for 40 additional minutes, the mixture was extracted with ethyl acetate (2 L). The upper organic layer was washed with 10% aqueous HCl (2×2 L), 7% aqueous NaHCO$_3$ (2×2 L), and 10% aqueous NaCl (2 L). The organic layer was dried over MgSO$_4$ and filtered. The solvent was removed on a rotary evaporator, giving crude (6) as a thick, black oil weighing 1.3 kg. The material was used in the subsequent reaction without further purification.

HPLC conditions: Column: Zorbax Eclipse XDB-C8; Solvent A=5% acetonitrile in 20 mM sodium phosphate buffer; solvent B=80% acetonitrile in water; gradient; flow rate=1.0 mL/min; injection volume=10 μL UV detection at 270 nm; r.t. di-silyl=10.1 min; r.t. monosilyl=6.9 min

Example 7

Synthesis of 2',3'-di-O-TBS-cytarabine hydrochloride (7)

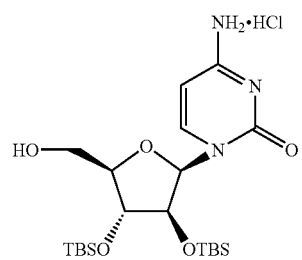

7

A 12 L, 4-neck round bottom flask was equipped with an overhead stirrer, condenser with nitrogen bubbler on top, a thermocouple, and a heating mantle. The flask was charged with a solution of the crude (6) in ethanol (2.3 L) and hydrazine (185 g, 5.76 mol). The mixture was heated at 80° C. for 15 h with monitoring by HPLC. The heating mantle was removed and the mixture cooled to 35° C. over a period of 2 h. The dark colored solution was poured into 15% aqueous NH$_4$Cl (4 L) and extracted with ethyl acetate (4 L). The organic phase was washed with 15% aqueous NH$_4$Cl (2 L) then evaporated to a thick oil on a rotary evaporator. The residue was dissolved in acetonitrile (3 L) and transferred to a large separatory funnel. A 10% solution of HCl in water (3 L) was added and the mixture stirred for 5 minutes. The resulting cloudy solution was extracted with hexanes (2×3 L). After hexane extraction the two phases were clear. The lower aqueous/acetonitrile layer containing (7) was concentrated on a rotary evaporator until 3 L of distillate were collected. Water (3 L) was added and distillation continued until approximately 500 mL additional solvent was removed. Precipitate formation began after the removal of 2 L with a thick slurry remaining after the distillation was stopped. The solid was collected by filtration in a 24 cm Buchner funnel and the cake was washed with 5% vol/vol acetonitrile in water (2×1 L). The wet solid (2.6 kg) was transferred to a 12 L flask and stirred with 5% acetonitrile/water (6 L) for 45 minutes. The solid was collected by filtration (slow), washed with water (1 L), and dried in a vacuum oven at 65° C. for 46 h, giving 644 g (88% yield). Purity was determined by HPLC and $^1$H NMR (DMSO-d$_6$): The crude material was charged to a 12 L flask. Ethyl acetate (4 L) was added and the mixture was heated to reflux over 1 h then maintained at reflux for 1 h. The mixture was cooled to 25° C. over 3 h. The resulting solid (7) was collected by filtration, washed with ethyl acetate, and dried in a vacuum oven at 65° C. for 24 h to give an off white solid (335 g, 46%).

The mother liquor was neutralized with saturated aqueous NaHCO$_3$ and the phases were separated. The organic phase was washed with brine, dried over MgSO$_4$, and evaporated on a rotary evaporator, giving 283 g of a thick, brown oil. The material was chromatographed on silica gel (1.1 kg), eluting with 2% MeOH/dichloromethane then 15% MeOH/dichloromethane. The fractions containing clean product were combined and the solvent evaporated. The resulting residue, 2',3'-di-O-TBScytarabine free base, was dried under vacuum overnight to give amber amorphous solid (171 g).

HPLC conditions: Column: Zorbax Eclipse XDB-C8; Solvent A=5% acetonitrile in 20 mM sodium phosphate buffer; solvent B=80% acetonitrile in water; gradient; flow rate=1.0 mL/min; injection volume=10 μL UV detection at 270 nm; r.t.=7.4 min Example 8

Synthesis of 2',3'-di-O-TBS-cytarabine-N,N-dimethylformamidine (8)

A 12 L, 4-neck flask equipped with an overhead stirrer was charged with (7) (333 g, 0.66 mol) and toluene (2 L). A solution of NaHCO$_3$ (110 g, 1.31 mol) in water (2 L) was added and the mixture stirred vigorously for 15 minutes. A large amount of solids was still present, so ethyl acetate (2 L) was added. Within 5 minutes, all the material was dissolved at a pH of 8. The phases were separated and the organic phase was washed with 10% aqueous NaCl solution (1.5 L), dried over MgSO$_4$, and filtered. The solvent was removed on a rotary evaporator, giving the free base as a white foam weighing 398 g (130% of theoretical).

The 2',3'-di-O-TBS-cytarabine free base (from chromatography in example 7) was added to the free base from above preparation in the rotary evaporator flask. Toluene (2 L) was added and the mixture was heated at 50° C. for 1 h, giving a clear, brown solution. The solution was transferred to a 12 L, 4-neck flask. Toluene (400 mL) was used to rinse the rotovap flask. DMF dimethyl acetal (158 g, 1.32 mol) was added and the mixture was stirred at 20° C. for 21 h and the reaction was monitored by TLC. The solvent was removed on a rotary evaporator, giving a thick oil. Hexane (1 L) was added and then removed under vacuum. The material was dried on the rotary evaporator for 2 h at 60° C., but still remained a sticky oil. Hexane (2 L) and dichloromethane (2 L) were added to the residue and the mixture stirred at 50° C., giving a clear, brown solution. The mixture was distilled at atmospheric pressure until 2 L of distillate were collected. The mixture was cooled slightly and the remaining solvent was evaporated under vacuum. The residue was dried on the rotary evaporator for 15 h, giving a hard foam. The material was scraped off the sides of the flask and the resulting free-flowing solid was dried under vacuum at 25° C. for 24 h to give 527.6 g (98%) of compound 8 as a tan solid.

TLC Conditions: The reaction mixture was monitored using Merck silica gel 60 plates, 2.5×7.5 cm, 250 micron; UV lamp: 10% MeOH in CH$_2$Cl$_2$; Rf of starting material=0.4; Rf of product=0.7.

$^1$H NMR (DMSO-d$_6$): δ −0.27 (s, 3H), −0.02 (s, 3H). 0.11 (s, 6H), 0.74 (s, 9H), 0.88 (s, 9H), 3.02 (s, 3H), 3.16 (s,3H), 3.51-3.69 (m, 2H), 3.80-3.85 (m, 1H), 4.05-4.08(m, 2H), 4.95-5.03 (m, 1H), 5.93-6.01 (m, 2H), 7.67 (d, 1H, J=7.2 Hz), 8.62 (s, 1H).

Example 9

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] (9)

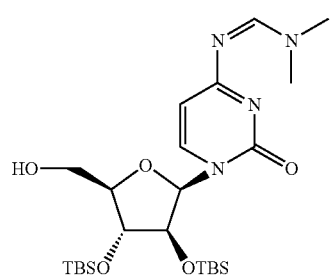

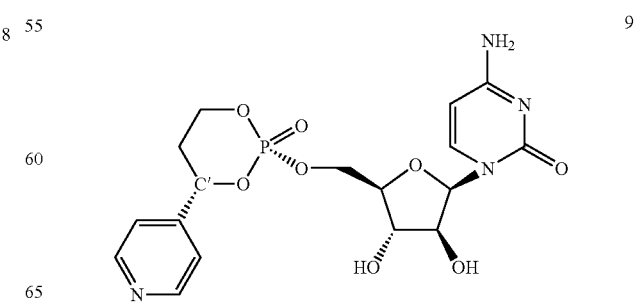

A 12 L, 3-neck round bottom flask was equipped with an overhead stirrer, thermowell/thermometer, addition funnel (1 L) and cooling bath. The flask was flushed with nitrogen and charged with the protected nucleoside 8 (250 g, 0.47 mol) and THF (2.5 L). The stirred solution was cooled to 4° C. (ice bath) and t-butylmagnesium chloride solution (617 mL, 0.62) was added slowly over 1 h, maintaining the temperature ≦8° C. After the addition was complete, the solution was stirred at ice bath temperature for 1.25 h. The phosphate reagent (4) (262 g, 0.78 mol) was added in one portion and the cooling bath was removed. The resulting mixture was stirred at ambient temperature for 16 h. The reaction was quenched with ammonium chloride solution (20 wt %, 2.5 L) and diluted with ethyl acetate (2.5 L). The mixture was stirred for 5 minutes to dissolve all residues, and the layers were separated. The aqueous phase was back-extracted with ethyl acetate (1.1 L) and the combined organic phase was washed with sodium chloride solution (15 wt %, 1.6 L), dried over $MgSO_4$ (260 g), filtered and concentrated under reduced pressure to provide 526 g of a dark orange sludge which was subjected to HPLC (see HPLC Conditions A below) analysis.

A 12 L, 3-neck round bottom flask was equipped with an overhead stirrer, thermowell/thermometer, condenser with base trap/bubbler, and heating mantle. The flask was charged with the crude sludge as a solution in methanol (2.5 L), and HCl-dioxane solution (790 mL, 3.16 mol). The stirred orange solution was heated to 50° C. and stirred at 50-55° C. for 16 h with monitoring by HPLC (see HPLC Conditions B below). The solvent was evaporated under reduced pressure to give a thick orange tar. The evaporation flask (10 L) was equipped with an overhead stirrer/bearing assembly, and the tar was partitioned between water (800 mL) and ethyl acetate (800 mL). Solid sodium bicarbonate was added in 2-5 g portions and stirred until the off-gassing subsided and the pH of the aqueous phase was 7 (wide range pH paper). The layers were separated and the aqueous phase was extracted again with ethyl acetate (800 mL). The aqueous phase was filtered and the water was evaporated via azeotropic distillation with ethanol under reduced pressure (4×400 mL ethanol carried out by sequential addition of ethanol) to provide 445 g of a brown oil/solid mixture as the water was gradually replaced with the ethanol. Ethanol (700 mL) was added and the slurry was stirred (overhead stirrer) at ambient temperature for 2 h.

9.1 The resulting mixture was filtered and the collected solid was washed with ethanol (2×50 mL) and dried to constant weight (−30 in. Hg, 55° C., 2 h) to provide 199 g of a beige solid which contained an undetermined amount of NaCl. This solid material was transferred to a 1 L round bottom flask equipped with magnetic stirring. Water (200 mL) was added and the mixture was stirred at ambient temperature for 16 h. The mixture was filtered and the collected solid (9) was washed with water (2×25 mL) and dried to constant weight (−30 in. Hg, 50° C., 16 h). Recovery=109 g of a beige powder (9) containing approximately 10% NaCl.

9.2. The ethanol filtrate from above was concentrated under reduced pressure to give a thick brown tar. The tar was dissolved in methanol (200 mL) with warming and the resulting thick solution was stirred at ambient temperature for 16 h. A precipitate had formed. The mixture was filtered and the collected solid (9) was washed with methanol (2×25 mL) and dried to constant weight (−30 in. Hg, 55° C., 16 h). Recovery=6.22 g of an off-white solid.

The product (9) from this example was isolated from the two separate work-up streams (9.1 and 9.2).

9.3. Purification of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl](9)

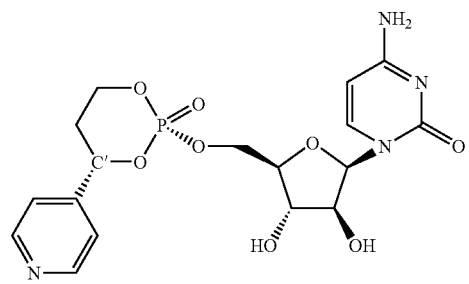

9

A 2 L, 3-neck round bottom flask was equipped with an overhead stirrer and charged with the combined crude (9) from the separate work-up streams and water (650 mL). The slurry was stirred and concentrated hydrochloric acid was added portionwise until the solids were dissolved (34 mL required, pH=3 by wide range pH paper. The initial 20 mL of HCl was added rapidly and the remaining was added in 5×2 mL and 4×1 mL portions. The orange solution was filtered and recharged to the flask. Solid sodium bicarbonate (36 g) was added portionwise in 2-3 g portions until the pH of the mixture was 6-7 (wide range pH paper). The mixture was stirred until the off-gassing subsided. The resulting mixture was stirred at ambient temperature for 2 h then filtered. The collected solid was washed with water (2×25 mL) and dried to constant weight (−30 in. Hg, 55° C., 16 h), giving 133.0 g of 2(1H)-pyrimidinone, 4-amino-1-[5-O-[(2R,4S)-2-oxido-4-(4-pyridinyl)-1,3,2-dioxaphosphorinan-2-yl]-β-D-arabinofuranosyl] as a yellow-beige granular solid (39.7%).

Elemental analysis calculated for $C_{17}H_{21}N_4O_8P$: C, 46.09; H, 4.85; N, 12.65. Found:

C, 45.88; H, 4.72; N, 12.58.

HPLC conditions: Columns: Two of the following columns in serial connection; Agilent, Zorbax Eclipse XDB-C8, 4.6× 250 mm, 5 μm; Solvent A=20 mM sodium phosphate buffer in 11% acetonitrile/water; solvent B=50% acetonitrile in deionized water; reversed phased; flow rate=1.0 mL/min; injection volume=10 μL UV detection at 210 nm, column temperature=30° C.; r.t.=13.4 min (S isomer); r.t.=14.1 min (R isomer)

$^1$H NMR (DMSO-$d_6$): δ 2.15-2.27 (m, 2H), 3.90-3.97 (m, 3H), 4.24-4.58 (m, 4H), 5.58 (d, 1H, J=7.4 Hz), 5.62-5.65 (m, 2H), 5.71-5.79 (m, 1H), 6.10 (d, 1H, J-3.6 Hz), 7.08 (s, 1H), 7.13 (s, 1H), 7.42 (d, 2H, J=5.8 Hz), 7.48 (d, 1H, J=7.4 Hz), 8.59 (d, 2H, J=6.0 Hz)

HPLC Conditions A:

Column: Chiralpak AD, 0.46×25 cm; mobile phase=10:90, ethanol:hexane, isocratic; flow rate=1.5 mL/min; injection volume=10 μL UV detection at 254 nm.

r.t.=18.9 min.

HPLC Conditions B

Column: Bondclone 10, C18, 300×3.9 mm; Solvent A 10% acetonitrile in 20 mM potassium phosphate buffer (pH 6.2), Solvent B acetonitrile; gradient; flow rate=1.4 mL/min; injection volume=10 μL UV detection at 260 nm.
r.t.=5.8 min.

Example 10

Synthesis of Chiral Ruthenium Catalyst (10)

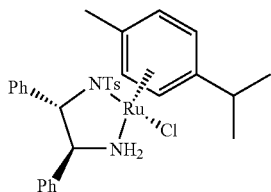

A 3 L, 3-neck round bottom flask was equipped with an overhead stirrer and thermowell/thermometer. The flask was flushed with nitrogen and charged with the ruthenium complex (32.0 g), (1S,2S)-(+)-N-p-tosyl-1,2-diphenylethylenediamine (38.24 g) and isopropanol (1.0 L). Triethylamine (30.0 mL) was added to the stirred slurry and the contents were heated to 80° C. over 1 h. The orange mixture was stirred at 80° C. for 1 h, then the heating mantle was removed and the stirred mixture was cooled to ambient temperature over 45 minutes. The solvent was evaporated under reduced pressure to give a dark orange solid. Methanol (320 mL) was added and the stirred slurry was heated to 50° C. The mixture was stirred at 50° C. for 15 minutes, and then gradually cooled to ambient temperature over 30 minutes. The mixture was stirred at ice bath temperature for an additional 30 minutes, and then filtered. The collected solid was washed with methanol (2×15 mL), then dried to constant weight (~30 in. Hg, 50° C., 1 h), giving 53.1 g of catalyst as an orange solid (80% yield).

Example 11

Synthesis of (4S)-(−)-(S)-(−)-(4-pyridyl)-2-(4-nitrophenoxy)-2-oxo-1,3,2-dioxaphosphorinane (4) using the hydrochloride salt of the diol

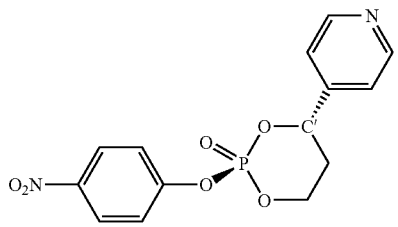

A 1 liter 3-neck round bottom flask was equipped with a mechanical stirrer, addition funnel, a thermometer and a N₂ inlet. The flask is charged with S-(−)-1-(pyrid-4-yl)-propane-1,3-diol (25 g, 163.4 mmol) and ethyl acetate (250 mL) and the resulting suspension was treated slowly with a 4 N HCl solution in dioxane (43 mL, 176 mmol) over a period of 15 min. After stirring for 30 min at room temperature, 4-nitrophenylphosphorodichloridate (41.81 g, 163.4 mmol) was added as a solid as quickly as possible under a positive flow of N₂. The internal temperature of the reaction mixture was adjusted to −10° C. with the help of a dry ice-acetone cooling bath. A solution of triethylamine (57.76 g, 79 mL, 572 mmol) in ethyl acetate (100 mL) was added maintaining the reaction temperature at <−5° C. Thirty minutes after the complete addition of the triethylamine solution, the cooling bath was removed and the reaction mixture was stirred at room temperature for 1 h. The reaction mixture was filtered to remove triethylamine-hydrochloride salt, which was washed with ethyl acetate (3×30 mL) until the filtrate showed only faint absorption. The filtrate was evaporated down to a volume of 150-175 mL under reduced pressure. 4-nitrophenol (7.5 g, 54.3 mmol) and triethylamine (9 mL) were added to the concentrated solution and the resulting orange reaction mixture was stirred at room temperature for 24 h. The solid formed in the reaction mixture was collected by filtration, washed with ethyl acetate (2×25 mL) and methyl t-butyl ether (25 mL) and dried in under vacuum at 55° C. to give 31.96 g (58.4%) of the desired product. Same analytical data as in example 4.

Example 12

Synthesis of (4S)-(−)-trans-(4-pyridyl)-2-chloro-2-oxo-1,3,2-dioxaphosphorinane (11)

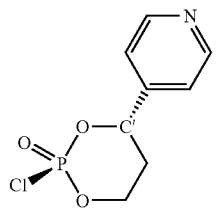

An oven-dried 250 mL round bottom flask equipped with a magnetic stir-bar was charged with 3.49 g of the S-(−) 1-(4-Pyridyl)-1,3-propanediol followed by 60 mL of acetonitrile. The heterogeneous mixture was allowed to stir at room temperature for 15 minutes and then slowly treated with 5.7 mL of 4 M HCl in dioxane solution over 5 minutes. After stirring for 1 hour at room temp the reaction mixture was treated with 2.16 mL of POCl₃ in one portion via a syringe. In a separate 25 mL flask 2.68 g of DABCO was dissolved in 15 mL of acetonitrile under nitrogen and transferred via a syringe or an addition funnel to the reaction mixture over 5 minutes. A slight exotherm was observed at the end of the addition of the DABCO solution (+10° C.). The reaction mixture was allowed to stir for 1 hour at ambient temperature during which it remained heterogeneous. A small sample of the reaction mixture was pulled out and quickly evaporated with a jet of dry N₂ and the residue was dissolved in DMSO-d₆ to run a ¹H-NMR spectrum.

¹H NMR (DMSO d₆, Varian Gemini 200 MHz): C'-proton: trans-isomer 5.85-5.75 (d, 1H).

Example 13

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] (9)

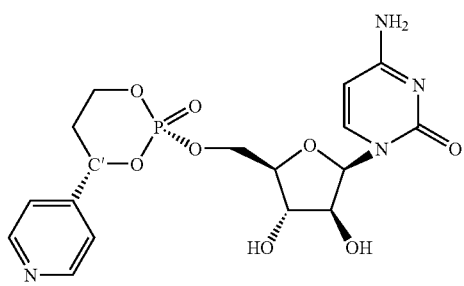

Method A:

An oven-dried 250 mL round bottom flask equipped with a magnetic stir bar was charged with 3.35 g of cytarabine-HCl and 6.0 mL of DMPU. Into this flask the reaction mixture from example 12 was filtered directly and the DABCO-HCl salt was washed quickly with acetonitrile (1×15 mL). Volatiles were removed on a rotary-evaporator under aspirator vacuum (bath temp <35° C.). The residual oil was briefly kept under high vacuum and stirred at room temperature for 48 h. The reaction mixture was treated with 100 mL of MeOH and stirred for 2 hours at room temperature. The pH of the reaction mixture was adjusted to 7.0 using 25 wt % NaOMe solution in methanol (approximately 13 mL were required). At this stage the reaction mixture was turbid. HPLC was run to insure integrity of the reaction profile. The reaction mixture was evaporated to dryness and the residue was stirred with 50 mL of dichloromethane for 30 minutes at room temperature. The precipitate was collected by filtration, washed with methylene chloride (1×20 mL) and transferred back to the flask, stirred again with 50 mL of dichloromethane for 15 minutes and filtered. The solid was stirred with 200 mL of ethanol for 1-2 hours, filtered and washed with ethanol (2×10 mL). The filtrate was evaporated to dryness to give 4.90 g of a white solid. This solid was dissolved in 10 mL of H$_2$O and stirred at room temperature overnight to give a solid which was collected by filtration, washed with water (2×3 mL) and dried in a vacuum oven to give compound 9, 1.38 g, (26%).

Method B:

Step A: Synthesis of Cytarabine Hydrochloride

A 5 L, 3-neck flask equipped with an overhead stirrer and thermocouple was charged with cytarabine (500 g, 2.06 mol) and methanol (2.0 L). The suspension was cooled to 2° C. HCl gas was bubbled in, giving a very thick mixture and an exotherm to 25° C. The suspension was diluted with methanol (0.5 L) to facilitate stirring. A total of 108 g (2.96 mol) of HCl gas was added. The mixture was stirred for 4 hours at 20° C. then filtered to collect the solid. The solid was washed with MTBE (3×250 mL) and dried in a vacuum oven at 70° C. to give 555 g (96% yield) of cytarabine hydrochloride as a flocculent, white solid.

Step B: Synthesis of 5'-O-cis-[4-(S)-(pyrid-4-yl)-1,3,2-dioxaphosphorin-2-oxo-2-yl]-cytosine-β-D-arabinofuranoside A 1 L jacketed cylindrical reactor was equipped with an overhead stirrer, thermocouple, and two addition funnels (60 mL and 125 mL). The reactor was flushed with nitrogen and charged with DMPU (188 mL, 195.8 g). The stirred liquid was cooled to −16° C. (Julabo F32 chiller/circulator).

Diol solution: A 250 mL round bottom flask was equipped with a magnetic stir bar and thermometer. The flask was charged with S-(−)-1-(pyrid-4-yl)-1,3-propanediol (50.0 g), DMPU (62.5 mL, 64.5 g) and pyridine (25.8 g) then placed under a nitrogen atmosphere. The stirred contents were heated to 40° C. (water bath) and stirred at 40-42° C. until all solids were dissolved (10 minutes). The resulting pale orange solution was cooled to 22° C. then charged to the 125 mL addition funnel (volume=127 mL).

POCl$_3$ solution: A 125 mL Erlermeyer flask was charged with acetonitrile (22.9 g) and phosphorus oxychloride (50.0 g). After mixing well, the colorless solution was transferred to the 60 mL addition funnel (volume=60 mL).

The two solutions were added simultaneously into the 1 L reactor over 2.6 h, maintaining the temperature below −11° C. After the additions were complete, the viscous pale orange solution was stirred, maintaining the temperature between −11 and −17° C. for 1 h. A sample of the reaction solution was pulled and checked for reaction completion by HPLC (aliquots were hydrolyzed to the cyclic phosphoric acid and then analyzed by HPLC). Cytarabine hydrochloride (60.9 g) was added. The resulting mixture was warmed to 5° C. over 1 h and stirred at 4-6° C. for 87 h. The resulting viscous reaction solution was sampled daily for HPLC analysis. The stirred reaction solution was slowly quenched with NaOH solution (13% wt/vol) at such a rate to maintain the temperature ≦20° C., until the pH of the solution reached 5.0 (290 mL of NaOH solution required). Dichloromethane (450 mL) was added and the biphasic mixture was stirred at 15-20° C. for 30 minutes. Stirring was stopped, and the mixture was allowed to settle for 30 minutes. The lower organic layer was separated. The upper aqueous layer was extracted twice more with dichloromethane (450 mL, 30-minute stir, 30-minute settle) (Note 5). The reactor was fitted with a pH probe and NaOH solution (13% wt/vol) was added over 10 minutes to pH 7.0 (68 mL of NaOH solution required). Cooling (5° C.) was applied to the jacket to keep the temperature below 20° C. The resulting solution was stirred at ambient temperature for 20 h then cooled to 5° C. for 5 h (Note 6). The resulting mixture was filtered and the collected solid was washed with water (2×100 mL) and dried to constant weight (−30 in. Hg, 60° C., 18 h). Recovery =46.6 g of a pale yellow, fine granular solid (48% yield).

HPLC for Phosphorochloridate Synthesis

Column: Zorbax Eclipse XDB-C8, 4.6×250 mm, 5 μm particle size; Solvent A-=20 mM sodium phosphate buffer in 11% acetonitrile/water; solvent B=50% acetonitrile in deionized water (gradient 100% A to 100% B in 15 minutes); flow rate=1.0 mL/min; injection volume=10 μL UV detection at 250 nm, column temperature=30° C.

r.t.=4.3 min

HPLC for 5'-O-cis-[4-(S)-(pyrid-4-yl)-1,3,2-dioxaphosphorin-2-oxo-2-yl]-cytosine-β-D-arabinofuranoside Columns: Inertsil ODS-3, 4.6×150 mm, 3 μm particle size; Solvent A=20 mM ammonium phosphate buffer in 5%, acetonitrile/water; solvent B=acetonitrile (gradient (time in minutes/% B in A %): 0/0, 30/10, 40/40, 40.1/0, 50/0); flow rate=1.0 mL/min; injection volume=50 μL UV detection at 210 nm, column temperature=30° C.±5° C.

r.t.=15.7 min

Step C: Purification of 5'-O-cis-[4-(S)-(pyrid-4-yl)-1,3,2-dioxaphosphorin-2-oxo-2-yl]-cytosine-β-D-arabinofuranoside Procedure 1: A 1 L, 3-neck flask equipped with an overhead stirrer, thermometer, addition funnel, and pH probe was charged with crude 5'-O-cis-[4-(S)-(pyrid-4-yl)-1,3,2-dioxaphosphorin-2-oxo-2-yl]-cytosine-β-D-arabinofuranoside (80 g, 0.18 mol) and deionized water (256 mL). The pH of the mixture was 5.16. Sulfuric acid, 3.0 M (60.6 mL, 0.18 mol) was added dropwise over 10 minutes. A 10° C. cooling bath was used to keep the temperature between 19-22° C. A slightly turbid, yellow solution resulted. The solution was filtered through a 0.45 μm nylon membrane filter (47 mm diameter). The flask and filter were rinsed with water (40 mL). The filtrate and washings were returned to the 1 L flask and the pH adjusted to 6.5 by adding 3 M NaOH (155 mL) and 3 M sulfuric acid. Precipitate formation was observed beginning at pH 5.1. The mixture was stirred 2.5 h then filtered to collect the solid. The flask and filter cake were washed with water (2×80 mL) and dried in a vacuum oven overnight (−30 in. Hg, 60° C., 18 h) to give 73.4 g of 5'-O-cis-[4-(S)-(pyrid-4-yl)-1,3,2-dioxaphosphorin-2-oxo-2-yl]-cytosine-β-D-arabinofuranoside as a coarse, pale yellow solid (92% yield).

Procedure 2: A 250 mL, 3-neck flask equipped with an overhead stirrer, thermocouple, addition funnel, and pH probe was charged with crude 5'-O-cis-[4-(S)-(pyrid-4-yl)-1,3,2-dioxaphosphorin-2-oxo-2-yl]-cytosine-β-D-arabinofuranoside (16 g, 36.3 mmol) and deionized water (50 mL). Aqueous sulfuric acid, 3.0 M was added dropwise to pH 2.5 (12 mL, 36.3 mmol), keeping the temperature below 22° C. Methanol (160 mL) was added over 20 minutes, giving a white precipitate. The suspension was stirred at 20° C. for 1.5 h then filtered to collect the solid. The solid was washed with methanol (2×25 mL) and dried in a vacuum oven (−30 in. Hg, 60° C., 1.5 h) to give 18.89 g of the sulfuric acid salt.

The solid was charged to a 250 mL, 3-neck flask equipped with an overhead stirrer and pH probe. Water (180 mL) was added and the mixture was stirred for 10 minutes to dissolve all the solids (pH=2.7). Sodium phosphate monobasic monohydrate (0.25 g, 1.81 mmol) was added and the mixture was stirred for 5 minutes. The solution was filtered through Celite. The filtrate was returned to the flask and 13% (wt/vol) aqueous NaOH was added to pH 7.1. The suspension was stirred at 20° C. for 3 hours. The solid was collected by filtration, washed with water (2×15 mL), and dried in a vacuum oven (−30 in. Hg, 60° C., 16 h) to a constant weight, giving 13.55 g (85% yield) of 5'-O-cis-[4-(S)-(pyrid-4-yl)-1,3,2-dioxaphosphorin-2-oxo-2-yl]-cytosine-β-D-arabinofuranoside as an off-white, granular solid.

Example 14

Synthesis of R-(+)-1-(4-Pyridyl)-1,3-propanediol

R-(+)-1-(4-Pyridyl)-1,3-propanediol as shown in Example 3 using the enantiomer of the catalyst 10 of example 10

Melting point=98-100° C.

e.e.=98% R isomer (determined by HPLC).

HPLC conditions: Column: Chiralpak AD, 0.46×25 cm; mobile phase=10:90, ethanol:hexane, isocratic; flow rate=1.5 mL/min; injection volume=10 μL UV detection at 254 nm; r.t.: R diol=12.7 min; S diol=14 min

Example 15

Synthesis of (4R)-(+)-(4-pyridyl)-2-(4-nitrophenoxy)-2-oxo-1,3,2-dioxaphosphorinane (12)

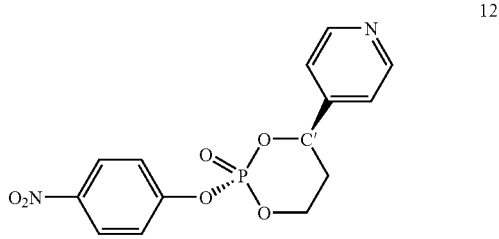

To a stirred solution of 4-nitrophenyl phosphorodichloridate (9.2 g, 36 mmol) in THF (100 mL) at 0° C. was slowly added pyridine (7.9 mL, 98 mmol) over 30 minutes. The reaction mixture was stirred for 5 minutes at 0° C. and slowly added to a solution of R-(+)-1-(4-pyridyl)-1,3-propane diol 95.8% ee, 5 g, 32.7 mmol) and triethylamine (15.6 mL, 114 mmol) in THF (300 mL) at 0° C. over 1.5 hours. The reaction mixture was allowed to warm to room temperature and stirred for 2.5 hours. Sodium 4-nitrophenoxide (18.17 g, 131 mmol) was added and the heterogeneous orange reaction mixture was heated at 40° C. for 4.5 hours. The reaction mixture was cooled to 0° C., quenched with a saturated aqueous solution of, ammonium chloride (250 mL) and the layers were separated. The organics were washed with a saturated aqueous solution of ammonium chloride (200 mL) and the combined aqueous washes were back-extracted with dichloromethane (100 mL). The combined organic extracts were washed with a 0.3 N aqueous solution of sodium hydroxide (200 mL×4) and dried over magnesium sulfate. The filtered solution was concentrated under reduced pressure to give an oil that crystallized upon standing. The yellow solid was recrystallized from 100 mL of 2-propanol to afford the desired trans-phosphate (12) as a white solid (95% ee, $[\alpha]_D^{20}$+74.2 (c 1.0, MeOH)).

TLC conditions: Uniplate silica gel, 250 microns; mobile phase=3/2 acetone/hexanes; diol: rf=0.2, trans-phosphate: rf=0.6, cis-phosphate: rf=0.5.

HPLC conditions for cis/trans-isomerization: Column=Zorbax Rx-C18 (4.6×250 mm); mobile phase=35% Acetonitrile/65% 20 mM phosphate buffer pH 7.95; flow rate=0.5 mL/min; detection=UV @250 nm; retention times: cis-isomer=9.39 min, trans-isomer=10.11 min.

HPLC conditions for ee determination: Column=Chiral Pak AD; mobile phase=1:1 2-propanol-hexanes; flow rate=1.0 mL/min; detection=UV @ 254 mm; retention times in min: trans-phosphate=7.02.

Example 16

Synthesis of 2(1H)-Pyrimidinone, 4-amino-1-[5-O-[(2S,4R)-2-oxido-4-(4-pyridinyl)-1,3,2-dioxaphosphorinan-2-yl]-β-D-arabinofuranosyl] (13)

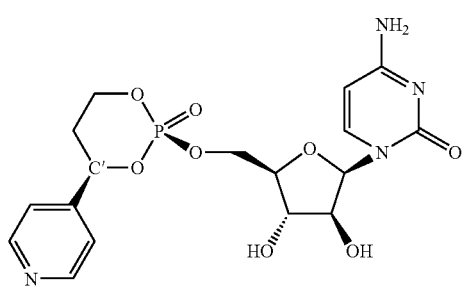

16.1. Phosphorylation Step

To a stirred solution of compound 8 (2.4 g, 4.55 mmol) in THF (40 mL) at room temperature was slowly added a solution of t-BuMgCl (1 M in THF, 6 mL, 6 mmol). After 30 minutes, the R-trans-phosphate 12 (1.84 g, 5.5 mmol) was added and the reaction mixture was stirred at room temperature for 16 hours. The reaction was cooled to 0° C., quenched with a saturated aqueous solution of ammonium chloride and extracted with ethyl acetate (50 mL×2). The combined organic layers were dried over magnesium sulfate, filtered and concentrated under reduced pressure. The crude product was purified by column chromatography on silica gel, eluting with acetone to afford the desired protected prodrug as an off-white solid (2.19 g, 66%, mp: 142.0-145.0° C.).

TLC conditions: Uniplate silica gel 250 microns; mobile phase=acetone, trans-phosphate: rf=0.6, protected ara-C: rf=0.2.

16.2. Deprotection Step

A stirred solution of the protected prodrug from above in 70% TFA (20 mL) was heated at 60° C. for 16 hours and the solvent was removed under reduced pressure. To the residue was added methanol (30 mL) and the mixture was made slightly basic with sodium carbonate. The cloudy solution was dried over magnesium sulfate and filtered. The solvent was removed under reduced pressure and the crude product was purified by column chromatography on silica gel, eluting with methanol-acetone (1:1) to afford the desired prodrug (13) as an off-white solid (1.06 g, 80%, 98% de, mp: 178.0-180.0° C.).

TLC conditions: Uniplate silica gel, 250 microns; mobile phase=acetone-methanol (1:1), protected ara-C: rf=0.7, product: rf=0.3.

HPLC conditions: Column=Zorbax Eclipse×DB-C8 4.6× 150 mm; mobile phase=20 mM phosphate buffer in 5% acetonitrile-water; flow rate=1.0 mL/min; detection=UV @ 210 nm; retention times in min: product =10.60.

Example 17

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl](+)-Camphorsulfonate Salt (+)-Camphorsulfonic acid (232 mg, 1 mmol) was added to a suspension of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] (9, 400 mg, 0.91 mmol) in methanol (8 mL). The resulting clear colorless solution was stirred at room temperature for 2 h then concentrated under reduced pressure. The residual white foam was triturated with ethyl acetate and concentrated under reduced pressure. The residue was suspended in ethyl acetate and heated to reflux. After cooling for 1 hour, the solid was collected by filtration, rinsed with ethyl acetate and dried under vacuum overnight at 50° C. to give the title compound as a white solid (562 mg). m.p. 193 dec. Elemental analysis (Robertson Microlit) calculated for $C_{17}H_{21}N_4O_8P.C_{10}H_{16}O_4S.H_2O$: C, 46.95; H, 5.69; N, 8.11. Found: C, 47.22; H, 5.51; N, 7.81.

Example 18

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] Maleate Salt Same procedure as for Example 17 using maleic acid (1.1 eq).

m.p. 140 dec. Elemental analysis (Robertson Microlit) calculated for $C_{17}H_{21}N_4O_8P.C_4H_4O_4.H_2O.0.5\ C_4H_8O_2$: C, 44.67; H, 5.05; N, 9.06. Found: C, 44.58; H, 4.61; N, 8.48.

Example 19

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] Hydrogensulfate Salt Sulfuric acid (89 mg, 091 mmol) was added to a suspension of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] (9, 400 mg, 091 mmol) in methanol (8 mL). The free flowing solid became sticky and stuck to the sides of the flask. The mixture was refluxed for 15 minutes cooled to room temperature and the solid was scrapped of the sides of the flask. After stirring at rt for 3 h, the white free flowing solid was collected by filtration, rinsed with methanol and dried under vacuum at 20° C. to give the title compound (428 mg)

m.p. 158 dec. Elemental analysis (Robertson Microlit) calculated for $C_{17}H_{21}N_4O_8P H_2SO_4 2H_2O$: C, 35.54; H, 4.74; N, 9.75. Found: C, 35.50; H, 4.73; N, 9.51.

Example 20

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] Hydrochloride Salt A 1 N solution of hydrochloric acid (228 μL, 0.23 mmol) was added to 2(1H)-Pyrimidinone, 4-amino-1-[5-O-[(2R, 4S)-2-oxido-4-(4-pyridinyl)-1,3,2-dioxaphosphorinan-2-yl]-β-D-arabinofuranosyl] (9, 100.6 mg, 0.228 mmol) in a flask. Water (5 mL) and methanol (5 mL) were added to the partially soluble solid and the mixture was sonicated. The clear colorless solution was filtered through a 0.45 μm syringe filter that was rinsed with methanol. The combined filtrates were concentrated under reduced pressure. The residue was azeotroped with acetonitrile (2×10 mL). The residue was dissolved in a mixture of acetonitrile and methanol (1/1, 10 mL) and concentrated to dryness. The white powder was dried under vacuum at 20° C. to give the title compound (78 mg).

m.p. >200° C. Elemental analysis (Robertson Microlit) calculated for $C_{17}H_{21}N_4O_8P.HCl.H_2O$: C, 42.03; H, 4.77; N, 11.53; Cl, 7.30. Found: C, 41.70; H, 4.84; N, 11.68; Cl, 7.45.

Example 21

Synthesis of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] L-Tartrate Salt Same procedure as in Example 20 using a 0.1 N solution of L-tartaric acid in water.

m.p. >200° C. Elemental analysis (Robertson Microlit) calculated for $C_{17}H_{21}N_4O_8P.C_4H_6O_6.H_2O.0.1$ $C_2H_3N$: C=41.57; H=4.82; N=9.38; Found: C=41.32; H=5.03; N=9.69.

Example 22

Synthesis of racemic trans-4-(4-pyridyl)-2-(4-nitrophenoxy)-2-oxo-1,3,2-dioxaphosphorinane A solution of racemic 1-(4-pyridyl)-1,3-propane diol (4 g, 26.1 mmol) and triethylamine (12 mL, 86 mmol) in THF was added to a solution of 4-nitrophenyl-phosphorodichloridate (7.35 g, 28.7 mmol) in THF. After stirring at room temperature overnight, sodium 4-nitrophenoxide (10 g, 71.8 mmol) was added and the reaction mixture was heated at 50° C. for 4 hours. The cooled reaction mixture was quenched with a saturated solution of ammonium chloride and extracted (3×) with ethyl acetate. The combined organic extracts were washed with a saturated sodium chloride and dried over sodium sulfate. The filtered solution was concentrated under reduced pressure and the resulting residue was purified by column chromatography (silica gel, dichloromethane/ethanol 95/5)

$^1$H NMR (CDCl$_3$, Varian Gemini 200 MHz): C'-proton: cis-isomer 5.6-5.8 (m, 1H); trans-isomer 5.5-5.6 9 (m, 1H).

TLC conditions: Uniplate silica gel, 250 microns; mobile phase=3/2 acetone/hexanes; diol: rf=0.2, trans-phosphate: rf=0.6, cis-phosphate: rf=0.5.

HPLC conditions for cis/trans-isomerization: Column=Zorbax Rx-C18 (4.6×250 mm); mobile phase=35% Acetonitrile/65% 20 mM phosphate buffer pH 7.95; flow rate=0.5 mL/min; detection=UV @ 250 nm; retention times: cis-isomer=9.39 mm, trans-isomer =10.11 min.

Example 23

Synthesis of 2(1H)-Pyrimidinone, 4-amino-1-[5-O-cis-[2-oxido-4-(4-pyridinyl)-1,3,2-dioxaphosphorinan-2-yl]-β-D-arabinofuranosyl]

23.1. Phosphorylation Step
Same as Example 16.1. using racemic trans-4-(4-pyridyl)-2-(4-nitrophenoxy)-2-oxo-1,3,2-dioxaphosphorinane.

TLC conditions: Uniplate silica gel 250 microns; mobile phase=acetone, trans-phosphate: rf=0.6, protected ara-C: rf=0.2.

23.2. Deprotection Step
Same as Example 16.2:
TLC conditions: Uniplate silica gel, 250 microns; mobile phase=acetone-methanol (1:1), protected ara-C: rf=0.7, product: rf=0.3.

Examples of use of the method of the invention includes the following. It will be understood that these examples are exemplary and that the method of the invention is not limited solely to these examples.

For the purpose of clarity and brevity, 2(1H)-Pyrimidinone, 4-amino-1-[5-O-[(2R,4S)-2-oxido-4-(4-pyridinyl)-1,3,2-dioxphosphorinan-2-yl] (9) is referred to as Compound A, 2(1H)-Pyrimidinone, 4-amino-1-[5-O-[(2R,4R)-2-oxido-4-(4-pyridinyl)-1,3,2-dioxaphosphorinan-2-yl]-β-D-arabinofuranosyl] (13) is referred to as Compound B, and 2(1H)-Pyrimidinone, 4-amino-1-[5-O-cis-[2-oxido-4-(4-pyridinyl)-1,3,2-dioxaphosphorinan-2-yl]-β-D-arabinofuranosyl] from Example 23 is referred to as Compound C in the following examples.

Biological Examples

Example A

Enzyme Kinetics in Human Liver Microsomes

Activation of Compound A and Compound B to araCMP by human liver microsomes was measured to compare activation in human liver tissue. CYP3A4 specificity was evaluated using pharmacologic inhibitors.

Methods:
Compound A and Compound B were incubated for 5 minutes with mixtures containing 2 mg/mL of human liver microsomes (In Vitro Technologies (IVT), catalog # X00821, lot # RQX, a mixed-sex pool of 50 donors), 100 mM potassium phosphate buffer (Sigma, catalog # P3786, lot # 62H0619), pH 7.4, and 1 mM NADPH (Calbiochem, catalog # 481973, lot # B38806). Reaction mixtures were preincubated for 2 minutes at 37° C. in an Eppendorf Thermal Mixer 5436 at 700 rpm in the absence of NADPH and then initiated by the addition of NADPH at 1 mM final concentration. The reactions were quenched with 112.5 μL of methanol 5 minutes later, samples were centrifuged for 10 minutes at 14,000 rpm in an Eppendorf microfuge, and 150 μL of supernatant evaporated to dryness with medium heat. Samples were resuspended in 60 μL of ion pair buffer (10 mM potassium phosphate, Fisher, catalog # P286-1, lot # 9152328A, 50 mM tetrabutyl ammonium hydroxide, Aldrich, catalog # 17,878-0, lot # 07030KO, pH adjusted to 4.5 with ~3.3 mL/L of phosphoric acid, 85% in water, Chempure, catalog #831-621, lot # M224 KBRR), vortexed, sonicated for ~30 seconds, and spun at 14,000 rpm for ~10 seconds.

To quantitate activation to araCMP, samples were analyzed by reverse phase HPLC (Hewlett Packard 1100). Fifty μL of each sample was injected onto an Agilent C18 Zorbax SB-AQ reverse-phase column (catalog # 883975-914, 5 μm, 4.6 mm×150 mm) with an Alltech C-18 EPS guard column (catalog # 32607, 7.5 mm×4.6 mm). Samples were loaded with ion pair buffer (see above) at a flow rate of 1 mL/min, a column temperature of 40° C., and a sample temperature of 4° C. AraCMP was eluted isocratically at ~7 minutes followed by a 70% methanol wash for 2 minutes. The efflux was monitored by UV absorbance at 272 nm.

Inhibition studies were conducted by preincubation with 0.1 μM to 100 μM troleandomycin (TAO; Sigma T-6514, lot #81K1655) or 0.01 μM to 10 μM ketoconazole (KTZ; Research Biochemicals International, catalog # K105, lot #

SJG-597A). Both TAO and KTZ were dissolved in methanol, hence all samples including controls contained a final concentration of 1% (v/v) methanol. For inhibition studies with TAO, the microsomes were preincubated with TAO for 30 minutes at 37° C. in the absence of substrate. Reactions (100 μL volume) were initiated by addition of substrate: 1000 μM Compound A or 1000 μM Compound B and a fresh aliquot of 1 mM NADPH. Ketoconazole did not require this preincubation procedure, so reactions were performed as described above with the addition of ketoconazole to the reaction mixture at the time of substrate addition.

Kinetic parameters are reported as mean±standard deviation (n=2 or 3 independent experiments). The Michaelis-Menten equation, Velocity=$V_{max}$[S]/[S]+$K_m$, was used to calculate $V_{max}$ and $K_m$ using Enzyme Kinetics Module v. 1.1 from Sigma Plot (SPSS, Inc.). Intrinsic clearance was obtained by dividing $V_{max}$ by $K_m$. $IC_{50}$ values for inhibition studies were determined by half-maximal interpolation with $IC_{50}$ values expressed as mean±standard deviation (n=2 or 3 independent experiments). $K_i$ was determined by the equation of Cheng and Prusoff, $K_i = IC_{50}/1+$[substrate]$/K_m$.

Results:

Using human liver microsome lot # RQX (Table 1), Compound A had a 2.6-fold higher intrinsic clearance than Compound B.

TABLE 1

Kinetic parameters of activation of Compound A and Compound B in human liver microsomes

|  | Compound A | Compound B |
| --- | --- | --- |
| Concentrations tested, mM | 0.25, 0.5, 0.75, 1 | 0.5, 1, 3, 6 |
| Vmax, nmol/min/mg | 0.11 ± 0.02 | 0.13 ± 0.02 |
| Km, mM | 1.08 ± 0.27 | 3.13 ± 0.51 |
| Clint, μL/min/mg | 0.11 ± 0.02 | 0.042 ± 0.003 |

Activation of Compound A and Compound B was inhibited by TAO with $IC_{50}$ values of 0.9±0.1 μM and 0.7±0.4 μM for Compound A and Compound B, respectively (Table 2). Complete inhibition (99%) of Compound A activation was observed at 100 μM TAO. The highest TAO concentration tested with Compound B was 10 μM, which resulted in 73±2% inhibition. $K_i$ values of TAO were similar for Compound A and Compound B, 0.5±0.1 μM and 0.5±0.3 μM, respectively.

As with TAO, KTZ inhibited Compound A and Compound B activation. $IC_{50}$ values were lower than those for TAO: 0.2±0.1 μM for both Compound A and Compound B (Table 2). Again, at 10 μM KTZ, maximal inhibition of 96±3% and 89±1% was observed for Compound A and Compound B activation, respectively. $K_i$ values were 0.1±0.03 μM for Compound A and 0.1±0.05 μM for Compound B.

Conclusions:

Compound A and Compound B are activated to araCMP by human liver microsomes. Compound A is activated at 2.6-fold greater rate than Compound B. KTZ and TAO inhibited prodrug activation suggesting that it was mediated by CYP3A4.

Example B

Single Dose Liver Levels

Activation of prodrugs in vivo was measured after bolus i.p. administration to mice.

Methods:

Normal non-fasted male Swiss Webster mice (25 to 35 g body weight, Harlan Sprague Dawley, Indianapolis, Ind.) were injected i.p. with Compound A or Compound B at 189 and 192 mg/kg, respectively, corresponding to molar equivalents of 100 mg/kg ara-C. At specified times post injection, mice were anesthetized and exsanguinated via cardiac puncture. The whole liver was removed, and snap-frozen in liquid nitrogen, and homogenized using a Polytron homogenizer PT 10/35 (Brinkmann Instruments, Westbury, N.Y.) in 3 volumes of 10% (v/v) perchloric acid (PCA). After a 5 min centrifugation at 2,500×g, 1 mL of supernatant was neutralized using 0.3 mL 3 M KOH/3 M $KHCO_3$ and mixed thoroughly. Samples were then centrifuged for 5 minutes and resulting supernatants were treated with periodate in order to remove endogenous ribonucleotides which otherwise might interfere with araCTP detection. For this, 100 μl tissue extract was incubated with 4 μl 0.5 M sodium periodate (Aldrich Chemical Co., Milwaukee, Wis., lot # 08009 BU) and 10 μl 1.8 M methylamine (Aldrich lot # 04526 DQ), pH 5.5) for 30 minutes at room temperature. The reaction was stopped with the addition of 2 μl 1 M L-Rhamnose (Aldrich lot # 06801 JS). Resulting samples were analyzed by HPLC as described below.

To measure bone marrow araCTP, the bone marrow samples were flushed from the marrow cavities of femurs with 1.2 ml saline into pre-weighed Eppendorf tubes. After centrifugation for 20-30 seconds (Eppendorf microfuge, 14,000 rpm) and removal of the supernatant, 12 volumes of 3% PCA (v/v) were added to the bone marrow cell pellets. Samples were then vortexed until the pellet was well dissolved and centrifuged as above for 10 min. Ninety μL of extracted supernatant was neutralized to pH 7-8 using 30 μL 1 M KOH/1 M $KHCO_3$ and again centrifuged. Resulting supernatants were periodate-treated as above.

Liver and bone marrow araCTP levels were determined by ion exchange phase HPLC (Hewlett Packard 1050) using a Whatman Partisil 5 SAX (5 μm, 4.6×250 mm) column. Samples (50 μL) were injected onto the column in 70% 10

TABLE 2

TAO and KTZ inhibition of activation in human liver microsomes

| COMPOUND | Conc. Tested (μM) | Inhibitor | IC50 (μM) | Ki (μM) | % inhib. at max. conc. of inhib. tested |
| --- | --- | --- | --- | --- | --- |
| Compound A | 1000 | TAO | 0.9 ± 0.1 | 0.5 ± 0.1 | 99% @ 100 μM (94% @ 10 μM) |
| Compound B | 1000 | TAO | 0.7 ± 0.4 | 0.5 ± 0.3 | 73 ± 2% @ 10 μM |
| Compound A | 1000 | KTZ | 0.2 ± 0.1 | 0.1 ± 0.03 | 96 ± 3% @ 10 μM |
| Compound B | 1000 | KTZ | 0.2 ± 0.1 | 0.1 ± 0.05 | 89 ± 1% @ 10 μM | mM ammonium phosphate buffer and 30% 1 M ammonium phosphate buffer, both at pH 3.5 and containing 6% ethanol. Nucleoside triphosphates were eluted from the column using a linear gradient to 80% 1 M ammonium phosphate pH 3.5/ 6% ethanol buffer, at a flow rate of 1.25 mL/min. AraCTP was detected by UV absorbance (280 nm) and usually eluted between 12 and 13 minutes. A standard curve was prepared by adding known amounts of araCTP into PCA extracts from control liver or bone marrow prior to neutralizing, and preparing HPLC samples accordingly.

To obtain plasma, blood was transferred to heparinized micro-collection tubes and centrifuged in an Eppendorf microfuge at 14,000 rpm for 2 minutes. Resulting plasma was collected, placed on dry ice, and subsequently stored at −20° C. On the day of analysis, proteins were precipitated by adding 1 mL acetonitrile to 100 µL of plasma. After 10 min centrifugation (Eppendorf microfuge, 14,000 rpm), the supernatant was removed and dried in a Savant SpeedVac Plus SC110A. Samples were reconstituted with 110 µL of mobile phase buffer (20 mM $KH_2PO_4$, pH 4.5), sonicated for 5 min, and centrifuged for 30 seconds. Supernatants were analyzed by reverse-phase HPLC (Hewlett Packard 1090) equipped with an Alltech C18 column (5 µm, 4.6 mm×250 mm). After injection of 50 µL sample in mobile phase buffer, the acetonitrile concentration was increased to 10% over 10 min. then to 50% over 15 min. Elution times for araC and prodrugs were around 3 and 19 min, respectively. AraC and prodrugs were detected by absorbance at 280 nm and quantitated using standard curves obtained with spiked plasma samples processed as above.

Results are expressed as mean±standard error of the mean. Data were analyzed by repeated measures ANOVA, followed by the Tukey HSD post-hoc test for comparisons at individual time points when appropriate. A p-value of less than 0.05 was considered statistically significant. Dotted lines in figures indicate LOQ (limit of quantitation) using the indicated HPLC method.

Figure 1B:
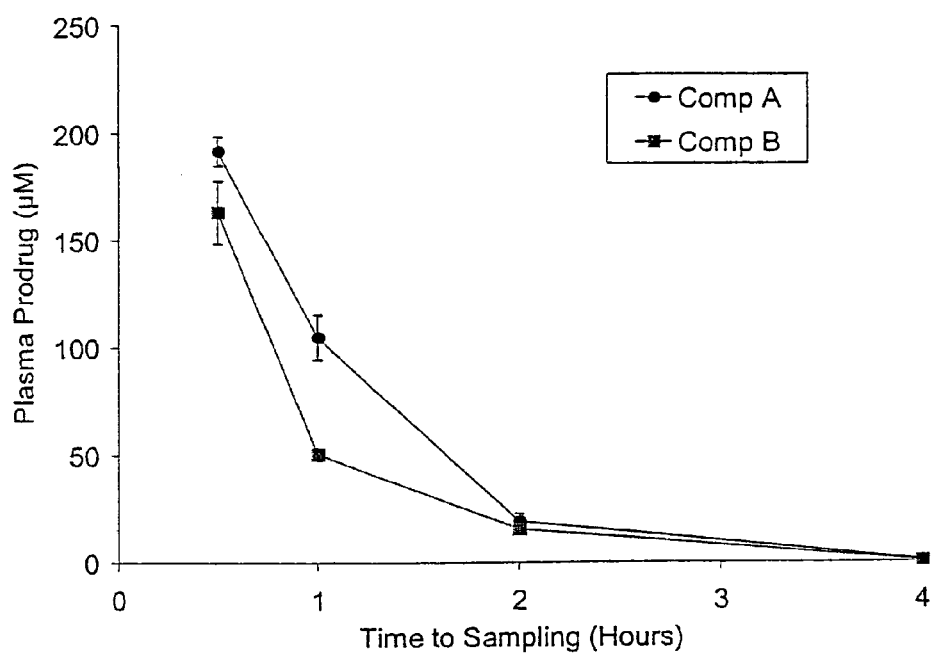
FIG. 1b. Depicts the level of prodrug in plasma when Compound A and Compound B are administered at a dose of 100 mg/kg CE to male NIH Swiss mice by a single i.p. bolus injection at time 0.
Figure 1C:
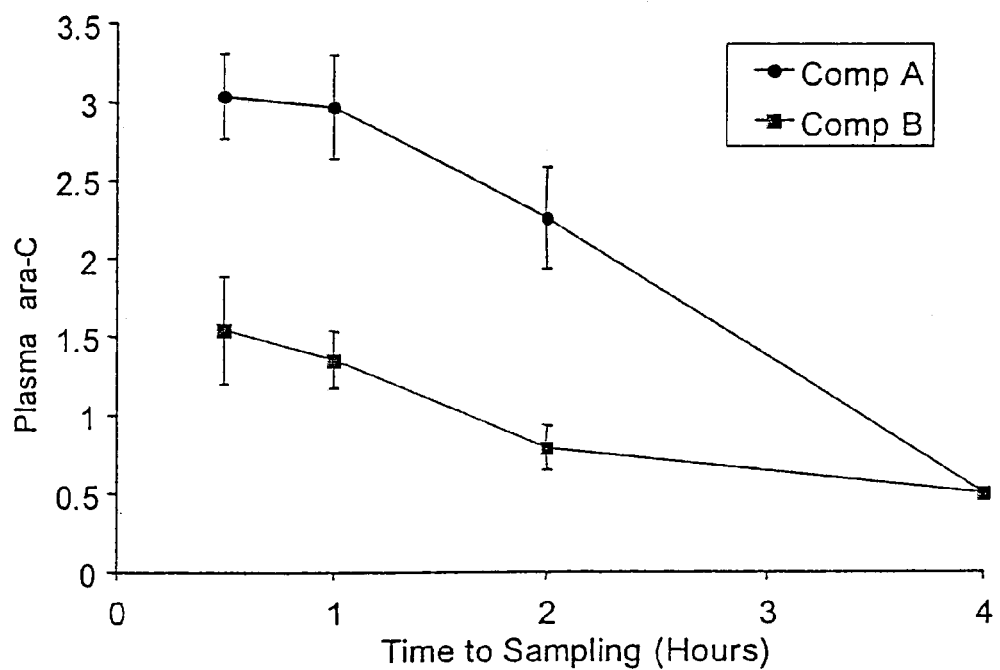
FIG. 1c. Depicts the level of araC in plasma when Compound A and Compound B are administered at a dose of 100 mg/kg CE to male NIH Swiss mice by a single i.p. bolus injection at time 0.

Results:

Compound A and Compound B generated high levels of araCTP in the liver (FIG. 1a.) that peaked at 60 minutes post injection at 69.89±6.37 and 27.00±4.04 nmoles/g for Compound A and Compound B respectively. Compound A produced significantly ($p<0.05$) higher liver araCTP levels than Compound B at all but the 4-hour time-point. Plasma prodrug levels were similar for Compound A and Compound B ($p<0.01$; FIG. 1b.). Plasma araC levels were greater in mice administered Compound A ($p<0.01$ for 0.5, 1 and 2 hrs; FIG. 1c.), correlating more with liver araCTP than plasma prodrug levels. This suggests that the plasma araC may be derived from the liver araCTP rather than degradation of the prodrug in plasma. Bone marrow araCTP was at or below the level of quantitation (3 nmol/g) in all samples suggesting good liver targeting.

Conclusions:

Both Compound A and Compound B result in significant levels of araCTP in the liver when administered by bolus i.p. injection. Compound A results in ~2-fold greater liver araCTP levels than Compound B. AraCTP was not detected in the bone marrow of animals treated with either compound. Plasma prodrug levels were similar for both prodrugs, but plasma araC levels were ~2-fold greater with Compound A. Based in the relative correlation of plasma araC levels to the liver araCTP levels, the plasma araC is presumed to be generated from liver araCTP possibly by dephosphorylation of araCTP to araC and leakage of araC from the liver cells back into the plasma.

Example C

Liver araCTP when Delivered by Continuous i.v. Infusion

Activation of prodrugs to araCTP and maintenance of liver araCTP levels was measured in rats that were instrumented for drug delivery by continuous i.v. infusion.

Methods:

Male Simonsen Albino rats (Sprague Dawley-derived, from Simonsen Laboratories, Inc., Gilroy, Calif.) were anesthetized with a 0.25 ml intraperitoneal injection of an anesthetic mix containing 150 mg Ketamine ("Vetamine", 100 mg/ml, Phoenix Scientific, Inc. St. Joseph, Md.), 10 mg xylazine (100 mg/ml, The Butler Company, Columbus, Ohio) and 5 mg morphine (15 mg/ml, Marsam Pharmaceuticals, Inc., Cherry Hill, N.J.) per 1.93 mls. A saline filled blunt PE-50 tubing catheter (Intramedic, Becton Dickinson, Sparks, Md.) was inserted into the jugular vein, exteriorized between the scapulae and connected to a swivel-tethering constant infusion system (Lomir Biomedical, Inc., Malone, N.Y. and Harvard Apparatus, Inc., South Natick, Mass.). The tubing was filled with heparinized saline and sealed, and the animals allowed to recover for one to seven days. Instrumented animals were entered into the following infusion protocols:

Compound A: Compound A was infused at 200 mg/kg/24 hours araC equivalents (CE) for 2, 4, 8, 16, 24 or 48 hours (n=4-5/group, except in 48 hour group where n=1)

Compound B: Compound B was infused at 200 mg/kg/24 hours CE for 2, 4, 8, 16, 24 or 48 hours (n=3-5/group). In addition, Compound A was infused at the same dose for 4 hours (n=3).

Compound C: Compound C was infused at 200 mg/kg/24 hours CE for 2, 4, 8, 16, 24 or 48 hrs (n=3-5/group).

Dose response: Compound A was infused at 144 and 200 mg/kg/24 hours CE for 4 hours (n=4-5/group). Compound B was infused at 50, 100 and 200 mg/kg/24 hours CE for 24 hours (n=3-5/group).

After the various durations of infusion the animals were anesthetized by intra-catheter injections of the anesthetic mix described above. Blood samples were obtained via cardiac puncture using a 23-gauge needle attached to a heparin coated 3 cc syringe. Liver samples were excised and snap-frozen in liquid nitrogen using a freeze-clamp and processed as described in Example B. Samples were analyzed for liver araCTP as described in Example B. Plasma and bone marrow samples were collected and analyzed for plasma prodrug, plasma araC and bone marrow araCTP levels as described in Example B.

Figure 2A:
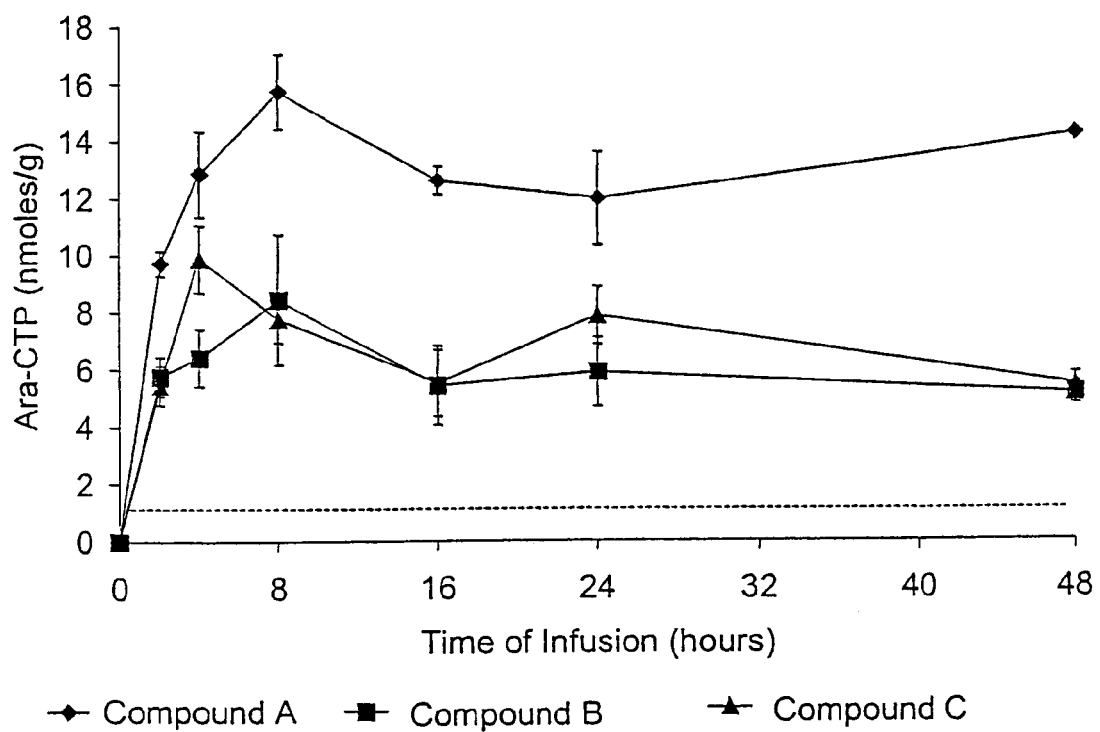
FIG. 2a. Depicts the level of araCTP in the liver after Compound A, Compound B, or Compound C are administrated by continuous i.v. infusion.

Results:

Continuous infusion of Compound A at 200 mg/kg/24 hours resulted in steady state liver araCTP levels by 4 hours (12.84±1.50 nmoles/g) and maintained an average of 13±1 nmoles/g for the remaining 44 hours (FIG. 2a). Plasma prodrug levels were similar for all three compounds ranging from 30-60 µM over the 48 hr treatment. Compound B and Compound C generated less araCTP in the liver than Compound A. These studies were performed independently; hence, to control for potential experimental variation, Compound A was administered to one group of animals in the Compound B study. Liver araCTP levels of those animals, measured after 4 hours of infusion, were similar to those obtained at the same time point in the 48-hour study for Compound A and plasma prodrug levels were identical for the two compounds suggesting differences in liver araCTP levels were not due to slight differences in pharmacokinetics. Bone marrow araCTP was at or below the level of quantitation (3 nmol/g) in all samples.

Figure 2B:
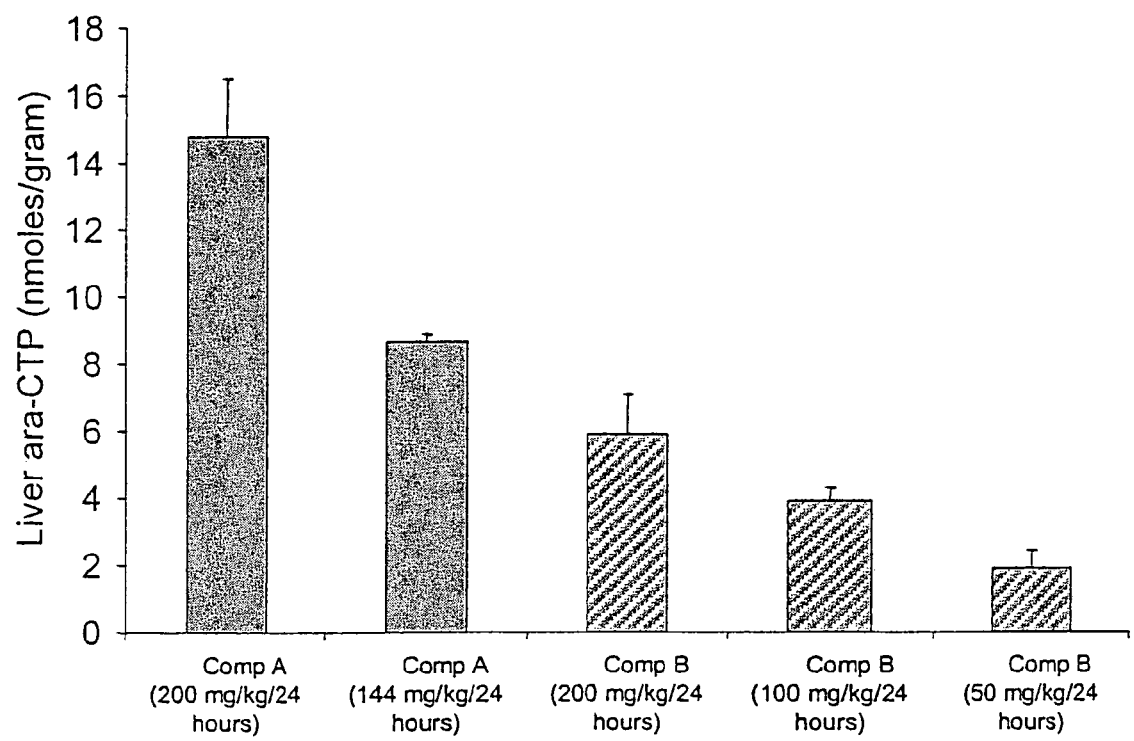
FIG. 2b. Depicts the dose response of liver araCTP after treatment with Compound A or Compound B.

The dose responsiveness of liver araCTP levels was tested by infusing Compound B at 100 or 50 mg/kg/24 hours over a 24-hour period or infusing Compound A at 144 mg/kg/24 hours over a 4-hour period. As shown in FIG. 2b, liver araCTP levels were dose-responsive for both prodrugs.

Conclusions:

Continuous infusion of Compound A, B or C results in significant and maintained araCTP levels in the liver. Administration of Compound A results in more liver araCTP than Compound B or Compound C with similar plasma prodrug levels suggesting differences are due to differences in activation rate rather than pharmacokinetics.

Example D

Liver Targeting

The liver specificity of araCTP delivery by these CYP3A-activated prodrugs was measured in vivo by comparing liver araCTP levels to active metabolite in other organs. In particular, the liver targeting relative to the bone marrow was evaluated because the bone marrow is the target organ of toxicity for cytarabine.

Methods:

Tissue distribution studies were performed in mice and rats as described in Examples B and C. In those studies, liver, plasma and bone marrow samples were obtained at necropsy to evaluate liver targeting. Similar studies were performed with the parent compound, cytarabine, to show utility as a liver targeted agent.

Results are expressed as mean±standard error of the mean. When appropriate, AUC was calculated from time zero to the last time-point of the study. Liver targeting indices (LTIs) were calculated by dividing the liver araCTP AUC by the AUC for plasma araC (plasma LTI) or by the AUC for bone marrow araCTP (bone marrow LTI) for each compound. For the continuous infusion studies, the steady state araCTP levels were divided by the steady state plasma araC levels.

Results:

As described in Example B, high levels of araCTP were detected in the liver when Compound A, Compound B, or Compound C were administered to mice or rats. Table 3 summarizes the peak levels and AUC for the bolus i.p. injection studies. Bone marrow araCTP was at or below the level of quantitation (3 nmol/g) in all studies suggesting good liver targeting. In contrast, high levels (19 nmol/g) of araCTP are detected in the bone marrow if 100 mg/kg cytarabine is administered in a similar fashion. There is no evidence that bone marrow directly activates the compounds to araCMP; any potential araCTP probably derives from activation of araC taken up from the plasma and phosphorylated to araCTP in the bone marrow. AraC is detected in the plasma of these animals and in all studies appears to correlate with liver araCTP levels. As shown in Table 3, plasma araC AUC values range from 3-22 $\mu$M*hr in mice and rats following the i/p/ administration of Compound A or Compound B. Estimating a liver targeting index (LTI) by taking the ratio of liver araCTP to plasma araC exposure over the duration of the experiment suggests a 19.2-27-fold targeting of araCTP to the liver relative to peripheral exposure. These values are 100-fold greater than the LTI for cytarabine. Steady state values can be similarly compared when Compound A, Compound B, or Compound C are delivered by continuous i.v. infusion (Table 4). The LTI ranges from 5->12 in those studies which is 1000-fold greater than the LTI for cytarabine administered at a 10-fold higher dose.

TABLE 3

In vivo mouse liver targeting of 4-pyridyl (Compound A, Compound B) HepDirect prodrugs of cytarabine. Compounds were administered at 100 mg (cytarabine equivalents)/kg using a single IP injection

| Compound | | Liver araCTP Peak @ 1 hr (nmol/g) | Liver araCTP $AUC_{0-4\,hr}$ (nmol/g * hr) | Plasma Prodrug $AUC_{0.5-4\,hr}$ (nmol/g * hr) | Plasma araC $AUC_{0-4\,hr}$ ($\mu$M * hr) | LTI (Liver/plasma) (nmol/g/$\mu$M) |
|---|---|---|---|---|---|---|
| Compound A | Mouse | 96 | 225 | 138 | 8.3 | 27 |
| Compound A | Mouse | 70 | 149 | 156 | 7.6 | 19.5 |
| Compound B | Mouse | 27 | 68 | 102 | 3.5 | 19.6 |
| Compound A | Rat | 267 | 422 | 147.1 | 21.9 | 19.2 |
| AraC | Mouse | 7.6 | <19.2 | N/A | 121.2 | <0.2 |

TABLE 4

Continuous infusion of 4-pyridyl (Compound A, Compound B. or Compound C) HepDirect prodrugs of cytarabine in rats. Prodrugs were administered at doses of 200 mg (cytarabine equivalents)/kg/day by continuous intravenous infusion.

| Compound (study) | Liver araCTP @ 4 hr (nmol/g) | Liver araCTP 24 hr (nmol/g) | Plasma Prodrug steady state ($\mu$M) | Plasma araC steady state ($\mu$M) | LTI @ 24 hrs (Liver/plasma) (nmol/g/$\mu$M) |
|---|---|---|---|---|---|
| Compound A | 12.8 | 12.0 | 40-50 | ~1.6 | 7.5 |
| Compound B | 6.4 | 5.9 | 25-35 | <0.5 | >12 |
| Compound C | 9.9 | 7.8 | 35-60 | ~1.5 | 5 |
| AraC* | 2.3 @ 2 hr | <2.26 | N/A | ~300 | <0.01 |

*AraC was given at 2000 mg/kg/day

Conclusions:

Compound A, Compound B, and Compound C effectively target araCTP to the liver reducing peripheral exposure by ~20-fold when administered intraperitoneally or ~10-fold when administered by continuous intravenous infusion. The targeting represents an improvement of 100-1000-fold over araC.

Example E

Aqueous Stability

The aqueous stabilities of the compounds were measured as a function of pH and buffer concentration.

Methods:

Compound A and Compound B were dissolved in water at 500 µM (0.23 mg/mL) as stock solutions. Diluted solutions (50 µM) were incubated at 37° C. in a Fisher Scientific dry bath incubator (catalog # 11-718-2) with samples collected every 24 hours and stored at −80° C. Plasma samples (100 µL) were quenched with 1 mL of acetonitrile. When all plasma samples were collected, samples were thawed, centrifuged for 10 minutes at 14,000 rpm in an Eppendorf microfuge, and 1 mL of supernatant was removed and evaporated to dryness for 2 or 3 hours with medium heat (~37° C.). Samples were resuspended in 120 µL of mobile phase buffer before HPLC injection.

Samples were analyzed on an HP1090 or HP1100 (Hewlett Packard) HPLC using a C-18 Alltech Econosphere column, 150 mm×4.6 mm (catalog # 70065), with a C-18 Alltech Econosphere guard column, 7.5 mm×4.6 mm (catalog # 96121). Samples were eluted with a methanol gradient: 0% for 5 minutes, then increasing to 10% at 10 minutes, 30% at 20 minutes, and 60% at 25 minutes. The column was allowed to equilibrate in 0% methanol for 10 minutes before the next injection. The flow rate was 1 mL/minute with a column temperature of 40° C. Prodrugs eluted around 19.5 minutes and were monitored by UV absorbance at 280 nm. For prodrugs in aqueous conditions, the same method was employed except the methanol gradient was as follows: 0% for 5 minutes, increasing to 10% at 10 minutes, and 30% at 20 minutes with prodrug eluting around 20 minutes.

Results:

Both Compound A and Compound B were quite stable in aqueous solution with $t_{90}$'s of >6 days in 10 mM potassium phosphate (Pi), pH 7.4, and 10 mM citrate, pH 5.0. Compound A stability was also >6 days in 100 mM Pi, pH 7.4, but the stability of Compound B was slightly less in this buffer, with a $t_{90}$ of 4 days. The stability of both compounds decreased in 100 mM citrate, pH5.0, with calculated $t_{90}$'s of 2 days and 1.7 days for Compound A and Compound B, respectively.

Conclusions:

Stability of the 4-pyridyl prodrugs is quite good, but the compounds are slightly less stable at low pH with high buffer strengths.

Example F

Solubility

The solubilities of Compound A and Compound B were measured under a variety of conditions to identify potential formulations for in vivo administration.

Methods:

The solubility of Compound A and Compound B was evaluated in 0.5 M Pi pH 8.0, 0.5 M citrate pH 7.0 and 0.5 M citrate pH 4.0 buffers. With each of the three buffer systems, saturating solutions of Compound A and Compound B were prepared as follows. A target of 30 mg of Compound A and 150 mg of Compound B were transferred to separate 4 cc clear glass vials and 1.0 mL of buffer was added to each vial. The resultant vials were sealed and equilibrated by tumbling at 25° C. for a minimum of 24 h. At the end of the incubation period, prodrug that was not in solution was removed from the samples by filtration through a 0.45 µm pore size nylon syringe filter. These diluted samples were assayed by the HPLC method of example E.

Results:

Compound A solubility was 2.9 mg/mL in pH 8 buffer, 2.6 mg/mL at pH 7.0 and 45.8 mg/mL at pH 4.0. Compound B solubility was 10.2 mg/mL in pH 8 buffer, 9.0 mg/mL at pH 7.0 and 94.6 mg/mL at pH 4.0.

Conclusions:

Both Compound A and Compound B are relatively soluble in neutral pH solutions with the solubility of Compound B exceeding that of Compound A. The solubility of both compounds increases substantially when prepared at pHs ≦4.

Example G

Plasma Stability

Stability of Compound A, Compound B, and Compound C in plasma was measured over 6 days to test whether the compounds will be stable in vivo.

Methods:

Male- and female-pooled human plasma (Bioreclamation Inc., Hickville, N.Y., catalog # HMPLNAHP, lot # BRH02236) containing heparin as anticoagulant, pH of all plasma aliquots was 8.3. Compound A and Compound B were dissolved in water at 500 µM (0.23 mg/mL) as stock solutions, diluted to 50 µM in plasma samples and incubated at 37° C. in a Fisher Scientific dry bath incubator (catalog # 11-718-2) with samples collected every 24 hours and stored at −80° C. Samples (100 µL) were quenched with 1 mL of acetonitrile. When all samples were collected, samples were thawed, centrifuged for 10 minutes at 14,000 rpm in an Eppendorf microfuge, and 1 mL of supernatant was removed and evaporated to dryness for 2 or 3-hours with medium heat (~37° C.). Samples were resuspended in 120 µL of mobile phase buffer before HPLC analysis. For plasma samples, 40 µL or 50 µL samples were injected onto the column described in Example E with mobile phase buffer, 20 mM potassium phosphate buffer, pH 6.2 (Fisher Scientific, catalog # P261-1, various lots). All other HPLC analysis was performed as described in Example E.

Results:

The t ½'s in human plasma at 37° C. were 6±½ days for all the compounds.

Conclusions:

With half-lives of >1 day in human plasma, Compound A, Compound B, and Compound C are not expected to undergo significant degradation in vivo.

Example H

Rat Acute Toxicity

Tolerability and safety of Compound A at a dose of 2000 mg/kg/24 hrs was evaluated after 24 hrs of continuous i.v. infusion.

Methods:

Male and female Simonsen rats were instrumented for continuous infusion as described in Example C. On the day of treatment, the rats were hooked up to the constant infusion tether and given free access to food and water. Three male and three female rats were treated Compound A at a dose of 2000 mg/kg/24 hrs using a flow rate of 2.08 ml/kg/hr. Compound A was dissolved at 42.5 mg/ml in water and the pH adjusted to 4 with 1M HCl. The osmolarity was adjusted to ~300 mOsm using 5M NaCl. As a control, 2 male rats were infused with pH 4 saline for the same period of time. The appearance and disposition of the rats was monitored regularly and notes about their behavior recorded every 1-3 hrs during the working day.

The animals were anesthetized in a chamber supplied via a Fluotec 3 vaporizer with 5% isoflurane (Abbot Laboratories, NDC 0074-3292-02) in 100% oxygen at a flow rate of 1.5 to 2 liters per minute. Blood samples were obtained during i.v. infusion via cardiac puncture using a 23-gauge needle attached to a heparin-coated 3 cc syringe. The blood from each animal was divided between $K_2$-EDTA-containing microtainer tubes (Becton Dickinson, 36/5974) and microtainer tubes with gel separators for serum (Becton Dickinson, 36/5956) and lithium heparin for plasma collection (Becton Dickinson, 36/5958). If possible, urine was removed from the bladder using a 23-gauge needle attached to a 3 cc syringe. Tissue samples were collected in the following order: liver, kidneys, small intestine, bladder and bone marrow. The small intestine was divided into three equal portions to represent samples from the duodenum, jejunum and ileum; fecal matter was manually removed by gentle sliding pressure using a blunt forceps. From each tissue, a portion was placed in 10% buffered formalin for histology. To measure nucleated bone marrow cells, the bone marrow samples were flushed from the marrow cavities of femurs with 1 ml PBS (w/o $Ca^{++}$ or $Mg^{++}$) and rigorously triturated and vortexed to separate the cells.

For cell counting, 50 mL of EDTA-treated blood or PBS-suspended bone marrow flush was mixed with 450 μL or 950 μL, respectively, nuclear staining solution containing 0.19 mg/mL crystal violet (Sigma # C-1658, lot 112H3660) in 1 M acetic acid, and incubated at room temperature for at least 5 min. After brief vortexing, a 10 μl aliquot of the mixture was placed in a hemocytometer and cells were counted using a Nikon Optiphot-2 microscope. The blood samples were counted under a 40× objective to evaluate the number of mononuclear cells (lymphocytes and monocytes) and polymorphonuclear cells (PMN, including granulocytes of the neutrophil, eosinophil and basophil type). Nucleated bone marrow cells were counted under a 10× objective.

EDTA-treated blood samples were submitted to LabCorp (San Diego, Calif.) for hematology analysis including erythrocyte and platelet numbers, hemoglobin, and hematocrit. Serum chemistry analysis was also performed by LabCorp. Tissue specimens from mice treated were coded and shipped in formalin to Comparative Biosciences (Mountain View, Calif.) for preparation of hematoxylin/eosin-stained tissue sections and histopathology evaluation.

Results:

Compound A was well tolerated at high doses with no significant behavioral differences noted between the drug-treated, vehicle-treated or untreated controls animals. At necropsy, it was noted that the stomachs of all perfused animals were empty, but no other differences were observed. Body weight and food consumption were not measured prior to or during the infusion protocol.

Blood, bone marrow and tissue sections were evaluated for a number of parameters. One concern was the potential for hepatotoxicity after exposure to high levels of Compound A or overt toxicities associated with the formulation. As described above, no overt toxicity was noted in the 24 hr treatment. All serum chemistry and hematology parameters were generally within normal ranges. A few samples gave rise to apparent outliers compared with published literature, but they were either not different than the untreated controls or were not considered toxicologically relevant. Of all the serum parameters evaluated, only the serum triglycerides levels were outside the normal range.

Blood mononuclear cells, PMN's and bone marrow counts were measured to test for potential acute effects on hematology. We were not anticipating significant or noticeable differences at this short time period. Indeed, no differences were detected in blood mononuclear cells or PMN's cells between untreated, vehicle treated or drug treated animals. Nucleated bone marrow cells were also not different between the vehicle treated and drug, treated animals.

Tissue samples from liver, kidney, small intestine (duodenum, jejunum, ileum), and urinary bladder were all evaluated by a pathologist. No significant histopathological findings were noted in any of the samples Conclusions:

Compound A was well tolerated by rats when administered by continuous intravenous infusion at high doses for at least the first 24 hrs.

Example I

Mouse 5-Day Safety Pharmacology

Safety of Compound C relative to that of the parent compound araC was evaluated in a 5-day repeated dose study in normal male mice.

Methods:

AraC was purchased from Sigma Chemical Co. (St. Louis, Mo., catalog # C1768, lot # 39H5962). Compound C and araC were dissolved in sterile physiological saline. Stock solutions were prepared daily from pre-weighed drug. All but the highest concentrations were prepared by diluting the stock solutions using additional sterile saline. Any drug not used immediately was refrigerated and used within 24 hours. All prodrugs were dosed in cytarabine molar equivalents (CE).

Male NIH Swiss Webster mice (25 to 33 g body weight, Harlan Sprague Dawley, Indianapolis, Ind.) were injected i.p. with Compound C, araC or vehicle once a day on days 0-4, approximately 3 to 4 hours following the beginning of the vivarium light cycle. Doses for Compound C were 1000, 300, 100 and 30-mg/kg nucleoside equivalents/day (equal to 1848, 554, 185 and 55.4 mg/kg/day) whereas araC was administered at 100, 30, 10 and 3 mg/kg/day. The vehicle was saline.

Body weights were recorded on days 0-4 immediately prior to compound administration and on day 5 prior to sacrifice. All mice were sacrificed on day 5 (23-25 hours following the last i.p. dose) by exsanguination under halothane anesthesia, and subsequent cervical dislocation. The blood from each animal was analyzed for blood chemistry and hematology parameters as described in Example H. Livers were excised and fixed in neutral-buffered 10% formalin, and bone marrow was flushed from the right femur using 1 ml PBS without calcium or magnesium and nucleated cell counts measured as in Example H.

EDTA-treated blood samples were submitted to LabCorp (LabCorp, San Diego, Calif.) for hematology analysis including erythrocyte and platelet numbers, hemoglobin, and hematocrit. Serum chemistry analysis was also performed by LabCorp. Tissue specimens from mice treated with vehicle or 100 mg/kg araC or 1000 mg/kg CE Compound C were coded and shipped in formalin to Comparative Biosciences (Mountain View, Calif.) for preparation of hematoxylin/eosin-stained tissue sections and histopathology evaluation. Specimen codes for the histopathology studies were: #1-7, Compound C 1000 mg/kg/day; #33-40, araC 100 mg/kg/day; #65-72, Saline vehicle.

Results are expressed as mean±standard error for 5-8 animals per dose group. For selected hematology parameters, data for each animal were also presented as a % of the mean of the vehicle group. Statistical analysis was performed by one-way ANOVA followed by Dunnett's post-hoc test for differences between a control group and multiple dose groups. A p-value of less than 0.05 was considered statistically significant.

Figure 3A:
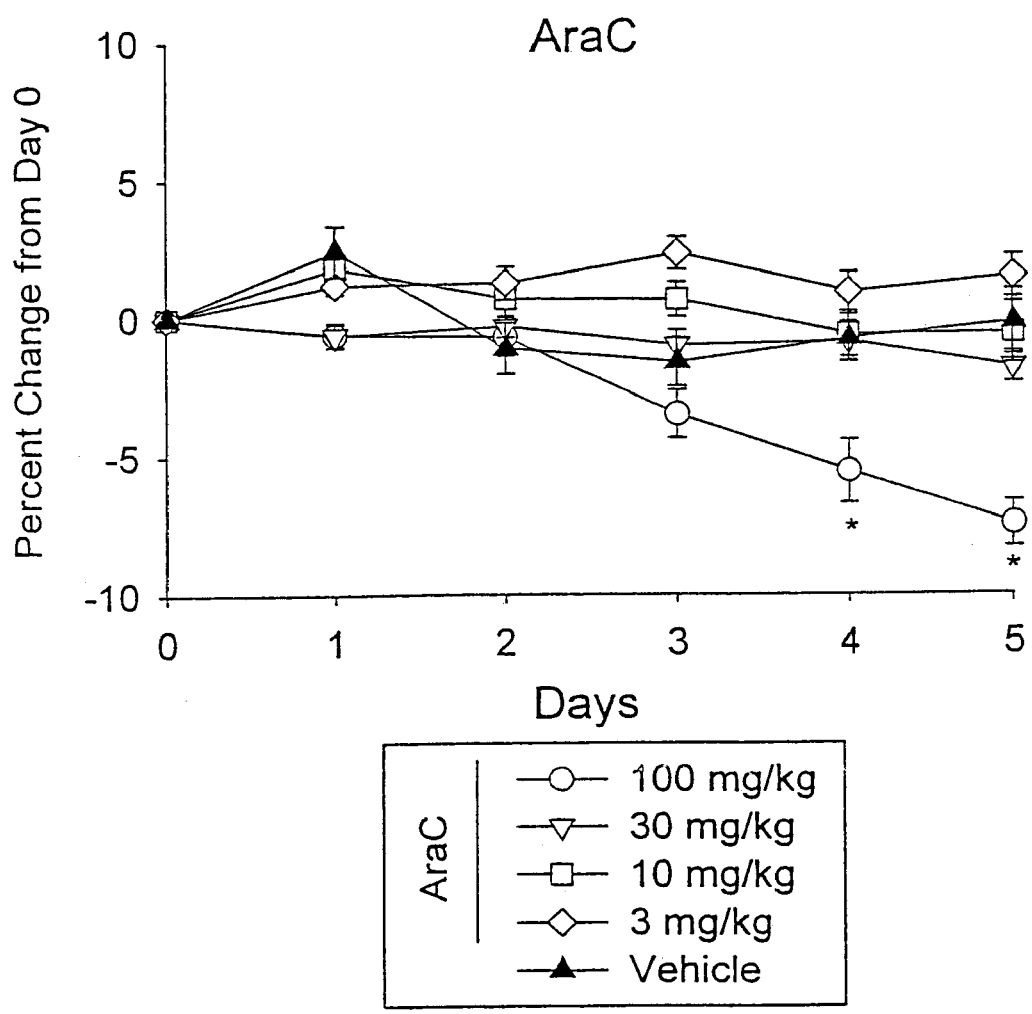
FIG. 3a. Depicts body weight, expressed as a percent of initial weight, as a function of time in mice treated with araC at doses of 30-1000 mg/kg CE for 5 days by daily IP injection.
Figure 3B:
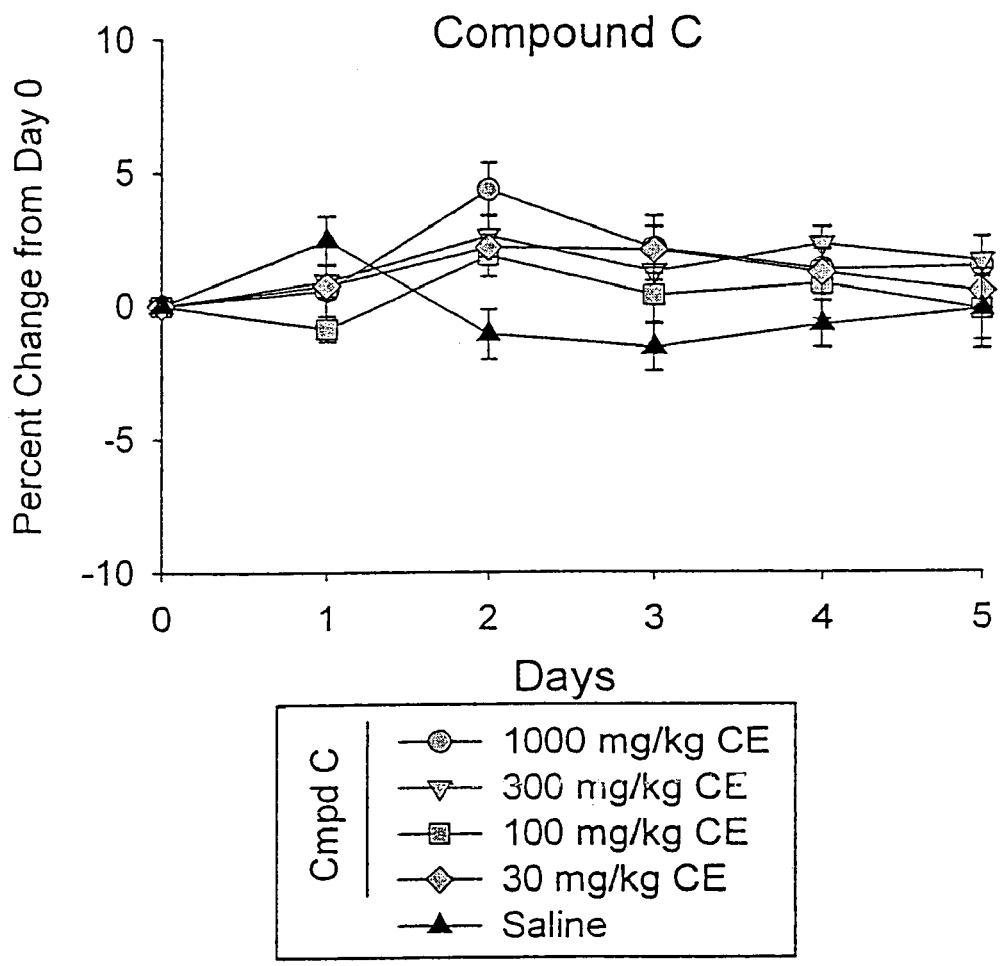
FIG. 3b. Depicts body weight, expressed as a percent of initial weight, as a function of time in mice treated with Compound C at doses of 30-1000 mg/kg CE for 5 days by daily IP injection.
Figure 4A:
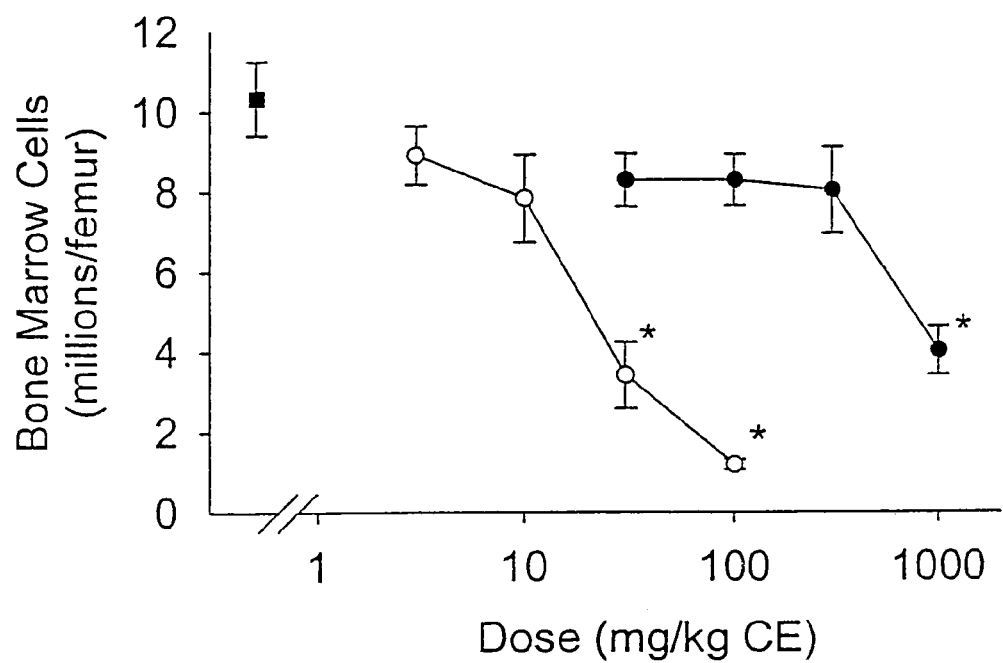
FIG. 4a. Depicts hematology endpoints-after 5-day treatment with araC or Compound C relative to saline vehicle. Nucleated bone marrow cells.
Figure 4B:
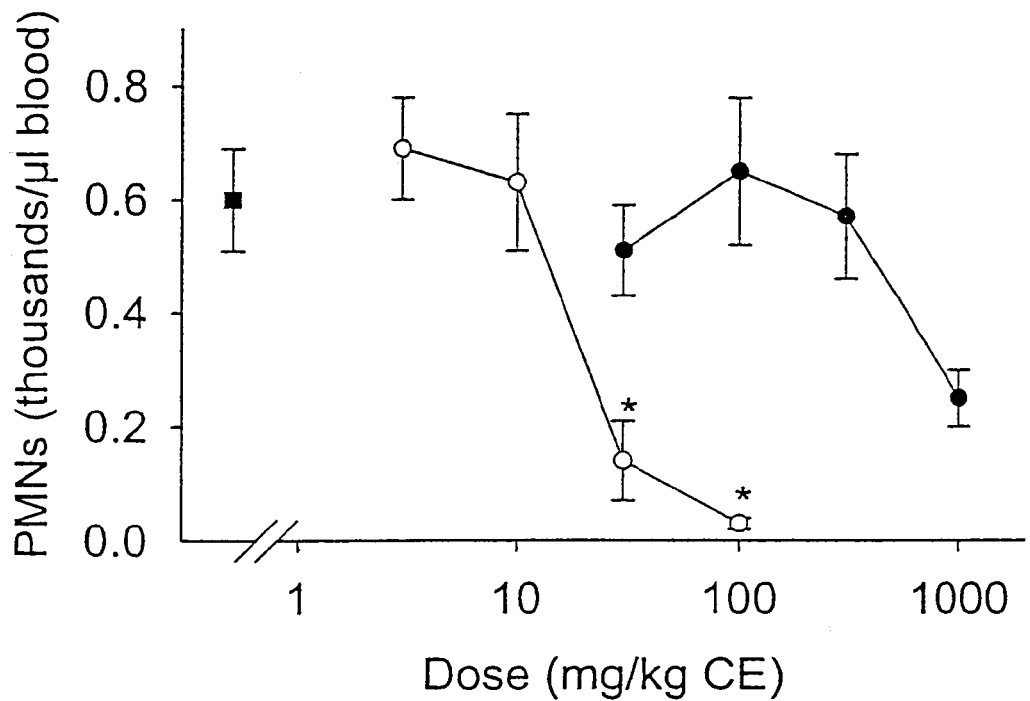
FIG. 4b. Depicts hematology endpoints after 5-day treatment with araC or Compound C relative to saline vehicle. Peripheral blood multinucleated cells (PMN's).
Figure 4C:
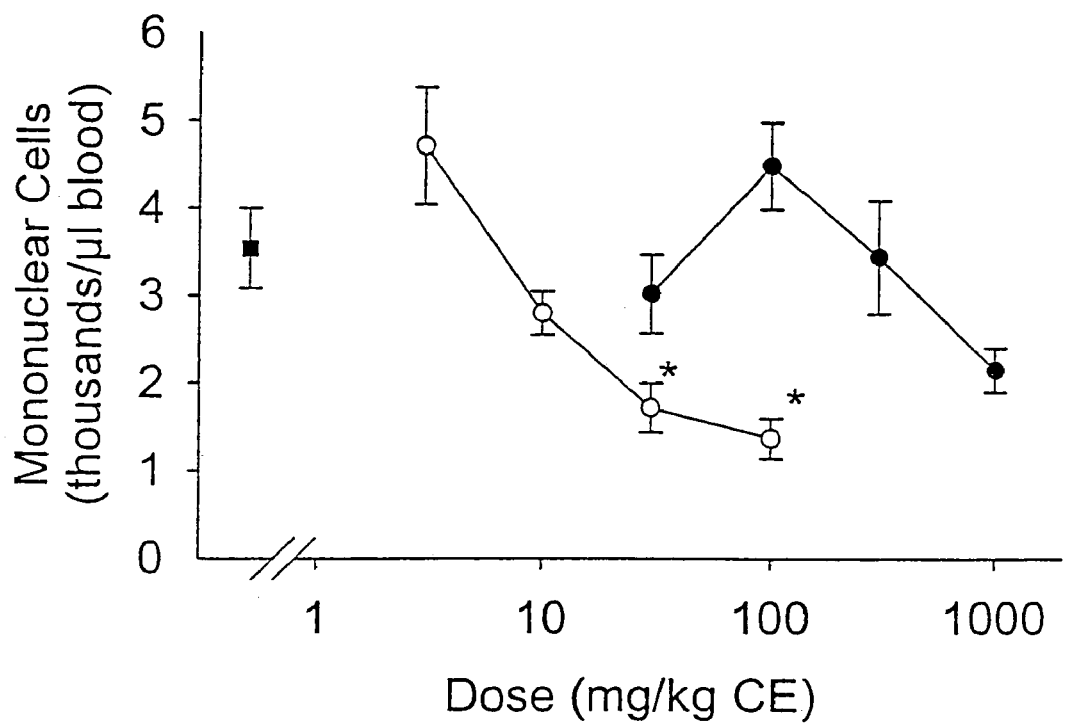
FIG. 4c. Depicts hematology endpoints after 5-day treatment with araC or Compound C relative to saline vehicle. Peripheral blood mononuclear cells.
Figure 4D:
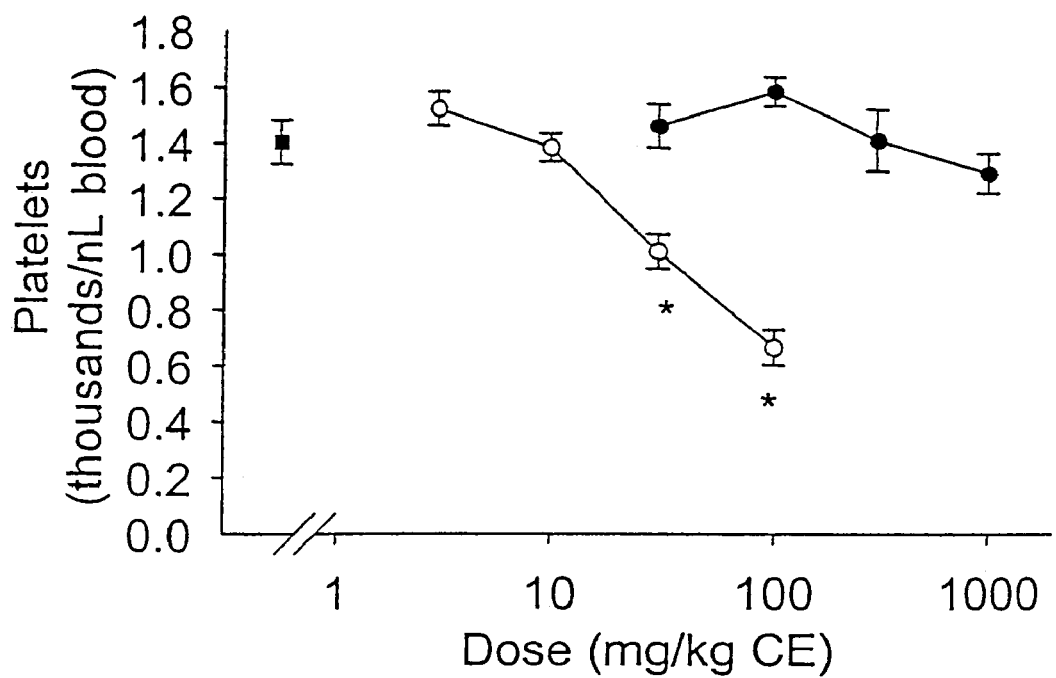
FIG. 4d. Depicts hematology endpoints after 5-day treatment with araC or Compound C relative to saline vehicle. Platelets.

Results:

Mice were injected i.p. with Compound C or araC at various doses for 5 days and sacrificed 24 hours after the final dose. No mice became overtly ill, as judged from behavior and general appearance; Whereas araC induced a progressive and statistically significant drop in body weight at the highest dose (FIG. 3a, 100 mg/kg/day), Compound C had no significant effect, even at the highest dose (1000 mg/kg/day of nucleoside equivalents) (FIG. 3b).

At 30 and 100 mg/kg/day, araC significantly decreased the number of nucleated bone marrow-cells, circulating PMNs, mononuclear cells, and platelets (FIG. 4). At the highest dose of araC, bone-marrow cellularity was reduced to 11% of that in vehicle-treated animals. A 30-fold higher dose of Compound C (1000 mg/kg/day of nucleoside equivalents) was required to reduce the number of nucleated bone marrow cells (FIG. 4a). In contrast to araC, Compound C did not affect PMN, mononuclear cell, or platelet numbers at any dose (FIGS. 4b-d).

AraC and Compound C significantly affected the red blood cell parameters, but at 10-fold different doses. AraC lowered erythrocyte numbers, hematocrit, and hemoglobin significantly at the two highest doses, 30 and 100 mg/kg/day. A slight reduction in hematocrit was also observed with araC at 10 mg/kg/day. Compound C similarly affected these parameters, but at ten-fold higher doses.

Serum chemistry analysis indicated that most analytes were unaffected by either compound. Specifically, the liver function test parameters (bilirubin, AST and ALT) were similar in animals treated with vehicle, araC, or Compound C. Alkaline phosphatase was significantly decreased at the highest dose of araC only. Albumin and BUN remained unchanged for all treatments. Creatinine and glucose were lowered by araC at the highest dose (100 mg/kg/day). Glucose was also lowered by araC at 30 mg/kg/day and by Compound C at 1000 mg/kg/day. The slight but significant effect of Compound C on glucose was the only effect of Compound C observed on any serum chemistry parameter.

A histopathologist at Comparative Biosciences evaluated formalin-fixed liver, kidney and small intestine specimens from mice treated with vehicle or 100 mg/kg araC or 1000 mg/kg CE Compound C and found no toxicologically relevant histopathologic changes in any samples.

Conclusions:

Compound C was ≧30-fold safer than araC in a 5-day repeated dose treatment protocol in terms of hematologic endpoints including nucleated bone marrow cells, peripheral PMN's and mononuclear cells. No hepatotoxicity was observed for either Compound C or its parent compound, araC.

What is claimed is:

1. A pharmaceutical composition comprising a pharmaceutically effective amount of a compound of Formula III:

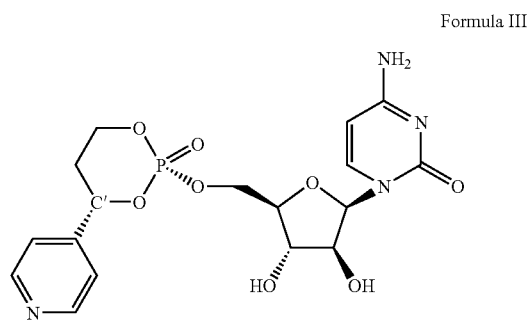

Formula III or a pharmaceutically acceptable salt thereof.

2. The pharmaceutical composition of claim 1, wherein said composition is suitable for oral administration, parenteral administration, administration by inhalation spray, topical administration, or rectal administration.

3. The pharmaceutical composition of claim 2, wherein said composition is suitable for parenteral administration.

4. The pharmaceutical composition of claim 1, wherein said composition is selected from the group consisting of aqueous isotonic sterile injection solutions, non-aqueous isotonic sterile injection solutions, aqueous sterile suspensions, and non-aqueous sterile suspensions.

5. The pharmaceutical composition of claim 1, wherein said composition is in a form selected from the group consisting of tablets, troches, lozenges, aqueous suspensions, oil suspensions, dispersible powders and granules, oil-in-water emulsions, hard and soft capsules, syrups and elixirs, and sterile injectable preparations.

6. The pharmaceutical composition of claim 5, wherein said composition is in the form of dispersible powders or granules.

7. The pharmaceutical composition of claim 5, wherein said composition is in the form of a sterile injectable preparation.

8. The pharmaceutical composition of claim 7, wherein said sterile injectable preparation is a sterile injectable solution or suspension.

9. The pharmaceutical composition of claim 3, wherein said composition is an aqueous sterile solution suitable for intravenous administration.

10. A pharmaceutical composition comprising a pharmaceutically effective amount of a compound of Formula III:

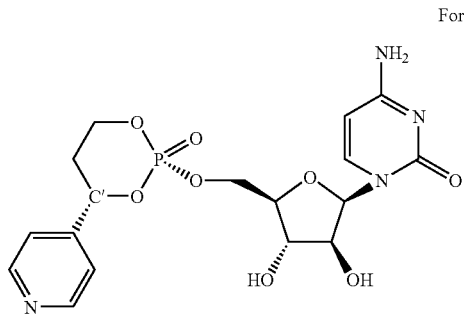

Formula III

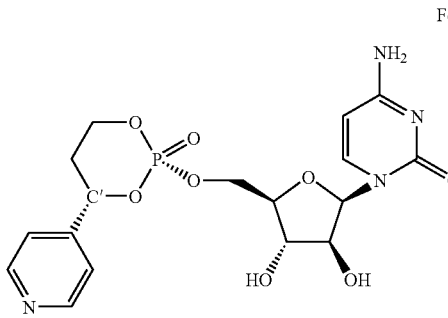

Formula III or a pharmaceutically acceptable salt thereof, and
a pharmaceutically effective amount of an oncolytic agent or salt thereof, wherein said composition is suitable for oral administration, parenteral administration, administration by inhalation spray, topical administration, or rectal administration.

11. The pharmaceutical composition of claim 10, wherein said oncolytic agent is selected from the group consisting of busulfan, carboplatin, cisplatin, miriplatin, temozolomide, thiotepa, melphalan, ifosfamide, cyclophosphamide, chlorambucil, doxorubicin, daunorubicin, epirubicin, idarubicin, plicamycin, valrubicin, dactinomycin, gemcitabine, floxuridine, fluorouracil, thioguanine, methotrexate, mitomycin, etoposide, paclitaxel, docetaxel, irinotecan, topotecan, teniposide, nedaplatin, carmustine, doxifluridine, cladribine, fludarabine, mercaptopurine, azatoxin, camptothecin, lurtotecan, 9-aminocamptothecin, pirarubin, neocarzinostatin, calicheamicin, esperamicin, and luroteca.

12. The pharmaceutical composition of claim 10, wherein said composition is suitable for parenteral administration.

13. The pharmaceutical composition of claim 10, wherein said composition is selected from the group consisting of aqueous isotonic sterile injection solutions, non-aqueous isotonic sterile injection solutions, aqueous sterile suspensions, and non-aqueous sterile suspensions.

14. The pharmaceutical composition of claim 10, wherein said composition is in a form selected from the group consisting of tablets, troches, lozenges, aqueous suspensions, oil suspensions, dispersible powders and granules, oil-in-water emulsions, hard and soft capsules, syrups and elixirs, and sterile injectable preparations.

15. The pharmaceutical composition of claim 14, wherein said composition is in the form of dispersible powders or granules.

16. The pharmaceutical composition of claim 14, wherein said composition is in the form of a sterile injectable preparation.

17. The pharmaceutical composition of claim 16, wherein said sterile injectable preparation is a sterile injectable solution or suspension.

18. The pharmaceutical composition of claim 12, wherein said composition is an aqueous sterile solution suitable for intravenous administration.

19. A pharmaceutical composition comprising a pharmaceutically effective amount of a compound of Formula III:

or a pharmaceutically acceptable salt thereof, and
a pharmaceutically effective amount of an agent that induces P450 activity or salt thereof.

20. The pharmaceutical composition of claim 19, wherein said agent that induces P450 activity is selected from the group consisting of rifampicin, a glucocorticoid, phenobarbital and erythromycin.

21. The pharmaceutical composition of claim 19, wherein said composition further comprises a pharmaceutically acceptable excipient or diluent selected from the group consisting of sweetening agents, flavoring agents, coloring agents, preserving agents, inert diluents, granulating and disintegrating agents, binding agents, lubricating agents, suspending agents, and dispersing or wetting agents.

22. The pharmaceutical composition of claim 19, wherein said composition is suitable for oral administration, parenteral administration, administration by inhalation spray, topical administration, or rectal administration.

23. The pharmaceutical composition of claim 22, wherein said composition is suitable for parenteral administration.

24. The pharmaceutical composition of claim 23, wherein said composition is selected from the group consisting of aqueous isotonic sterile injection solutions, non-aqueous isotonic sterile injection solutions, aqueous sterile suspensions, and non-aqueous sterile suspensions.

25. The pharmaceutical composition of claim 19, wherein said composition is in a form selected from the group consisting of tablets, troches, lozenges, aqueous suspensions, oil suspensions, dispersible powders and granules, oil-in-water emulsions, hard and soft capsules, syrups and elixirs, and sterile injectable preparations.

26. The pharmaceutical composition of claim 25, wherein said composition is in the form of dispersible powders or granules.

27. The pharmaceutical composition of claim 25, wherein said composition is in the form of a sterile injectable preparation.

28. The pharmaceutical composition of claim 27, wherein said sterile injectable preparation is a sterile injectable solution or suspension.

29. The pharmaceutical composition of claim 23, wherein said composition is an aqueous sterile solution suitable for intravenous administration.

* * * * *